(12) United States Patent
Kriesel et al.

(10) Patent No.: US 8,211,059 B2
(45) Date of Patent: *Jul. 3, 2012

(54) FLUID DISPENSER WITH ADDITIVE SUB-SYSTEM

(76) Inventors: Marshall S. Kriesel, St. Paul, MN (US); Joshua W. Kriesel, San Francisco, CA (US); Thomas N. Thompson, Richfield, MN (US)

( * ) Notice: Subject to any disclaimer, the term of this patent is extended or adjusted under 35 U.S.C. 154(b) by 576 days.

This patent is subject to a terminal disclaimer.

(21) Appl. No.: 12/215,933

(22) Filed: Jun. 30, 2008

(65) Prior Publication Data

US 2009/0024083 A1    Jan. 22, 2009

Related U.S. Application Data

(63) Continuation-in-part of application No. 11/823,084, filed on Jun. 25, 2007.

(51) Int. Cl.
*A61M 37/00* (2006.01)
(52) U.S. Cl. ...................................................... 604/132
(58) Field of Classification Search .......... 604/131–151, 604/890.1, 891.1
See application file for complete search history.

(56) References Cited

U.S. PATENT DOCUMENTS

| | | | |
|---|---|---|---|
| 2,236,084 A | 3/1941 | Brown | |
| RE27,155 E | 7/1971 | Hansen | |
| 3,731,681 A | 5/1973 | Blackshear et al. | |
| 4,140,117 A * | 2/1979 | Buckles et al. | 604/132 |
| 4,381,006 A | 4/1983 | Genese | |
| 4,525,165 A | 6/1985 | Fischell | |
| 4,557,728 A | 12/1985 | Sealfon et al. | |
| 4,608,042 A | 8/1986 | Vanderveen et al. | |
| 4,681,566 A | 7/1987 | Fenton, Jr. et al. | |
| 4,755,172 A | 7/1988 | Baldwin | |
| 4,772,263 A | 9/1988 | Dorman et al. | |
| 4,850,807 A | 7/1989 | Frantz | |
| 4,863,429 A | 9/1989 | Baldwin | |
| 5,007,556 A | 4/1991 | Lover | |
| 5,014,750 A | 5/1991 | Winchell et al. | |
| 5,098,377 A | 3/1992 | Borsanyi et al. | |
| 5,100,389 A | 3/1992 | Vaillancourt | |
| 5,176,641 A | 1/1993 | Idriss | |
| 5,205,820 A | 4/1993 | Kriesel | |
| 5,226,551 A | 7/1993 | Robbins, III | |
| 5,236,418 A | 8/1993 | Kriesel | |
| 5,290,259 A | 3/1994 | Fischer | |
| 5,306,257 A | 4/1994 | Zdeb | |
| 5,314,405 A | 5/1994 | Kriesel et al. | |
| 5,333,761 A | 8/1994 | Davis et al. | |
| 5,336,188 A | 8/1994 | Kriesel | |
| 5,346,476 A | 9/1994 | Elson | |
| 5,380,287 A | 1/1995 | Kikuchi et al. | |
| 5,411,480 A | 5/1995 | Kriesel | |
| 5,419,771 A | 5/1995 | Kriesel | |
| 5,484,410 A | 1/1996 | Kriesel et al. | |

(Continued)

*Primary Examiner* — Matthew F Desanto
(74) *Attorney, Agent, or Firm* — James E. Brunton

(57) ABSTRACT

A compact fluid dispenser for use in controllably dispensing fluid medicaments, such as, antibiotics, analgesics, and like medicinal agents from the device reservoir which is provided in the form of a novel collapsible bottle-like assembly. The fluid dispenser includes a unique stored energy mechanism which takes the form of a spring member of novel design that provides the force necessary to continuously and substantially uniformly expel fluid from the device reservoir. The device also includes novel adjustable flow rate control assembly that is disposed intermediate the fluid reservoir outlet and the outlet port of the device for precisely controlling the rate of fluid flow from the outlet port toward the patient.

16 Claims, 65 Drawing Sheets

U.S. PATENT DOCUMENTS

| | | | |
|---|---|---|---|
| 5,499,968 A | 3/1996 | Milijasevic et al. | |
| 5,514,090 A | 5/1996 | Kriesel et al. | |
| 5,545,139 A | 8/1996 | Kriesel | |
| 5,620,420 A | 4/1997 | Kriesel | |
| 5,632,406 A | 5/1997 | Robbins, III | |
| 5,693,018 A | 12/1997 | Kriesel et al. | |
| 5,693,019 A | 12/1997 | Kriesel | |
| 5,720,729 A | 2/1998 | Kriesel | |
| 5,721,382 A | 2/1998 | Kriesel et al. | |
| 5,735,818 A | 4/1998 | Kriesel et al. | |
| 5,741,242 A | 4/1998 | Kriesel | |
| 5,743,879 A | 4/1998 | Kriesel | |
| 5,766,149 A | 6/1998 | Kriesel et al. | |
| 5,779,676 A | 7/1998 | Kriesel et al. | |
| 5,807,323 A | 9/1998 | Kriesel et al. | |
| 5,836,484 A | 11/1998 | Gerber | |
| 5,858,005 A | 1/1999 | Kriesel | |
| 5,885,250 A | 3/1999 | Kriesel et al. | |
| 5,897,530 A | 4/1999 | Jackson | |
| 5,921,962 A | 7/1999 | Kriesel et al. | |
| 5,925,017 A | 7/1999 | Kriesel et al. | |
| 5,957,891 A | 9/1999 | Kriesel et al. | |
| 5,993,425 A | 11/1999 | Kriesel | |
| 6,010,482 A | 1/2000 | Kriesel et al. | |
| 6,027,472 A | 2/2000 | Kriesel et al. | |
| 6,030,363 A | 2/2000 | Kriesel | |
| 6,045,533 A | 4/2000 | Kriesel et al. | |
| 6,050,400 A | 4/2000 | Taskis et al. | |
| 6,063,059 A | 5/2000 | Kriesel | |
| 6,068,613 A | 5/2000 | Kriesel et al. | |
| 6,068,614 A | 5/2000 | Kimber et al. | |
| 6,086,561 A | 7/2000 | Kriesel et al. | |
| 6,090,071 A | 7/2000 | Kriesel | |
| 6,095,491 A | 8/2000 | Kriesel | |
| 6,126,637 A | 10/2000 | Kriesel et al. | |
| 6,126,642 A | 10/2000 | Kriesel et al. | |
| 6,152,898 A | 11/2000 | Olsen | |
| 6,159,180 A | 12/2000 | Kriesel et al. | |
| 6,176,845 B1 | 1/2001 | Kriesel et al. | |
| 6,183,441 B1 | 2/2001 | Kriesel et al. | |
| 6,190,359 B1 | 2/2001 | Heruth | |
| 6,210,368 B1 | 4/2001 | Rogers | |
| 6,236,624 B1 | 5/2001 | Kriesel et al. | |
| 6,245,041 B1 | 6/2001 | Kriesel | |
| 6,258,062 B1 | 7/2001 | Thielen et al. | |
| 6,270,481 B1 | 8/2001 | Mason et al. | |
| 6,273,133 B1 | 8/2001 | Williamson et al. | |
| 6,277,095 B1 | 8/2001 | Kriesel et al. | |
| 6,293,159 B1 | 9/2001 | Kriesel et al. | |
| 6,319,235 B1 | 11/2001 | Yoshino | |
| 6,355,019 B1 | 3/2002 | Kriesel et al. | |
| 6,391,006 B1 | 5/2002 | Kriesel et al. | |
| 6,394,980 B2 | 5/2002 | Kriesel et al. | |
| 6,398,760 B1 | 6/2002 | Danby | |
| 6,485,461 B1 | 11/2002 | Mason et al. | |
| 6,537,249 B2 | 3/2003 | Kriesel et al. | |
| 6,542,350 B1 | 4/2003 | Rogers | |
| 6,558,358 B2 * | 5/2003 | Rosoff et al. | 604/200 |
| 6,569,125 B2 | 5/2003 | Jepson et al. | |
| 6,645,175 B2 | 11/2003 | Kriesel et al. | |
| 6,669,668 B1 | 12/2003 | Kleeman et al. | |
| 6,740,059 B2 * | 5/2004 | Flaherty | 604/67 |
| 7,029,455 B2 | 4/2006 | Flaherty | |
| 7,169,128 B2 | 1/2007 | Kriesel et al. | |
| 7,220,245 B2 * | 5/2007 | Kriesel | 604/134 |
| 7,449,012 B2 | 11/2008 | Young et al. | |

\* cited by examiner

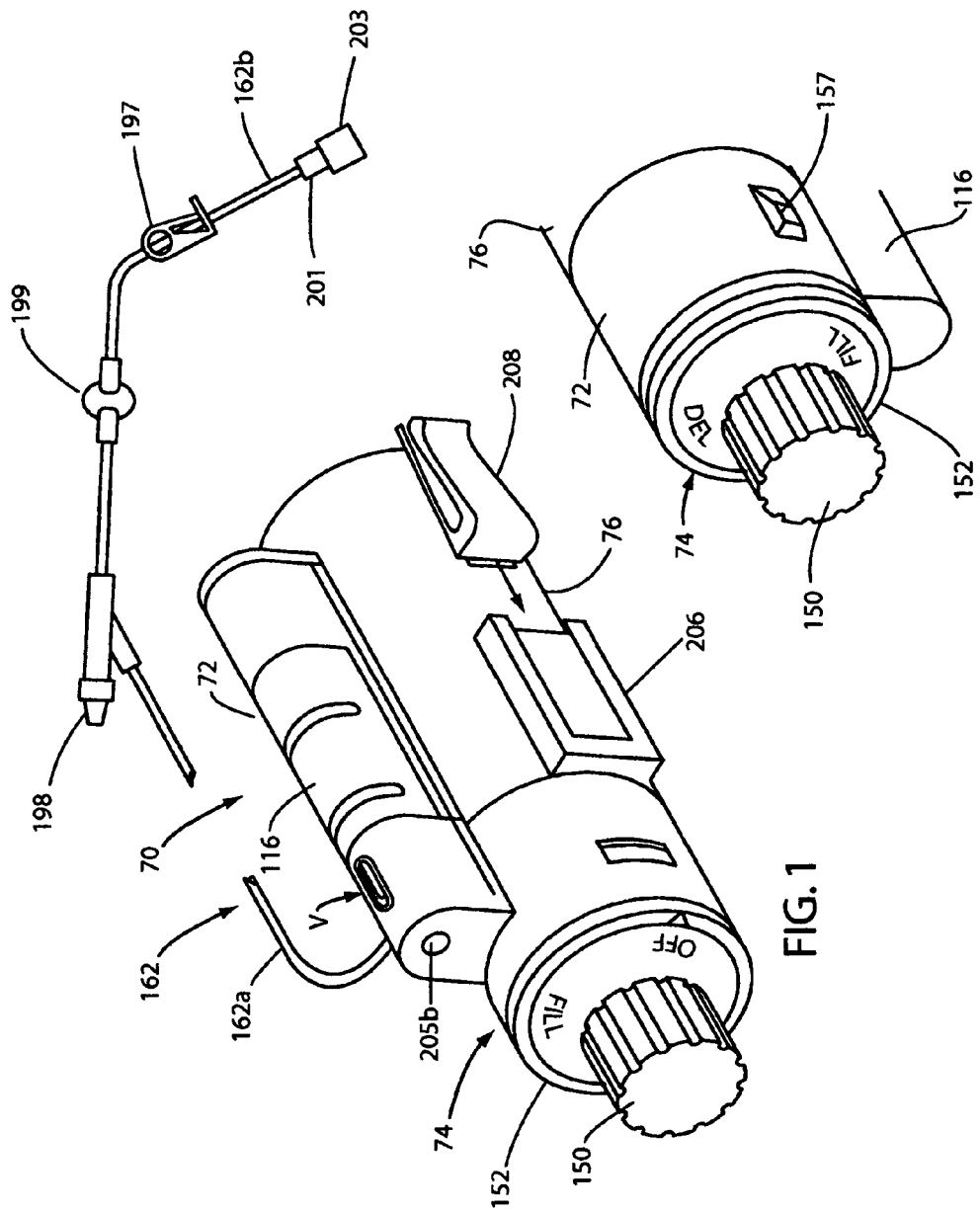

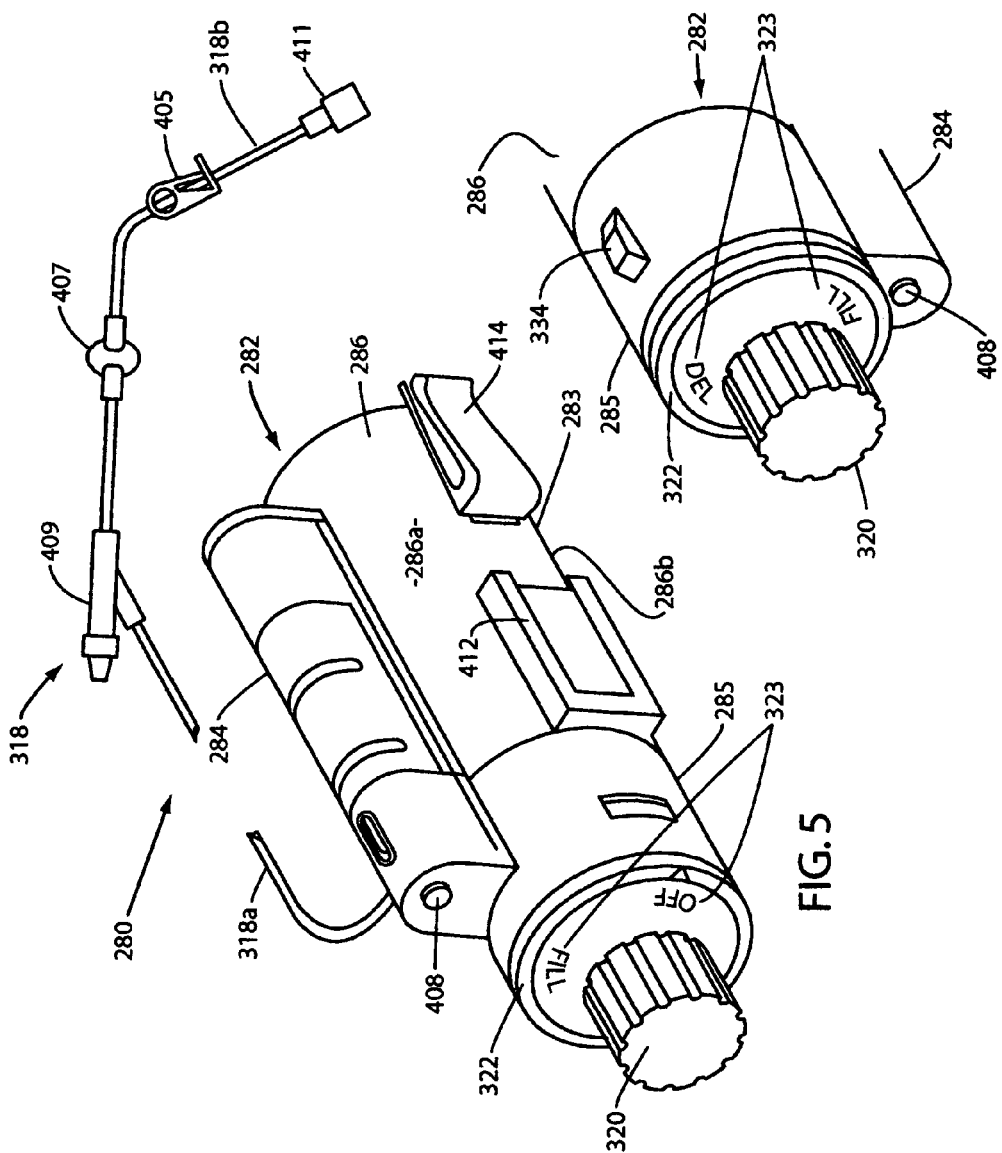

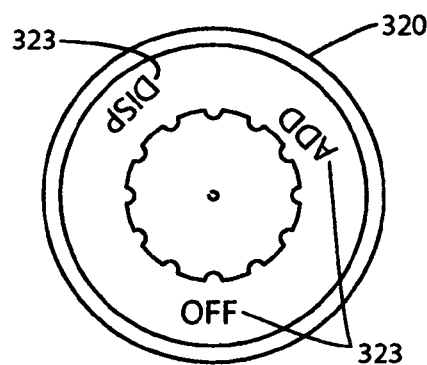
FIG. 20
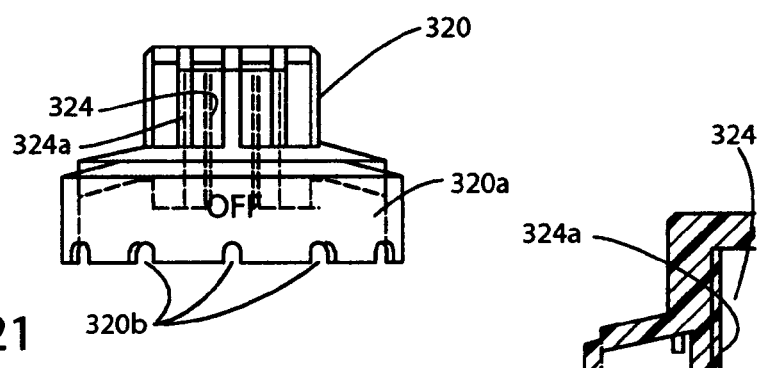
FIG. 21
FIG. 24
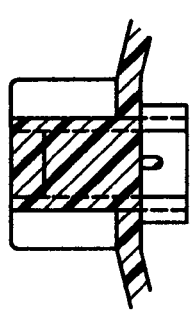
FIG. 23
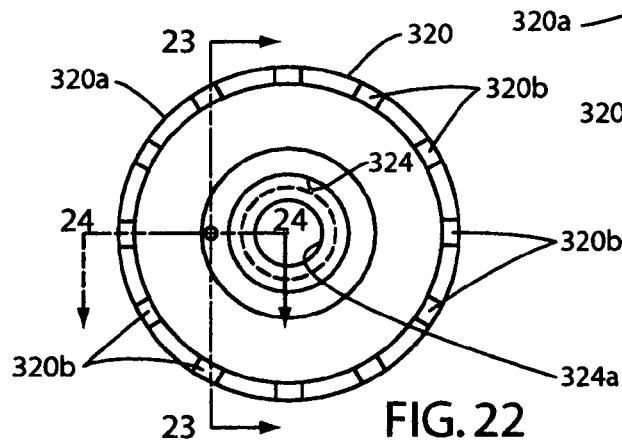
FIG. 22

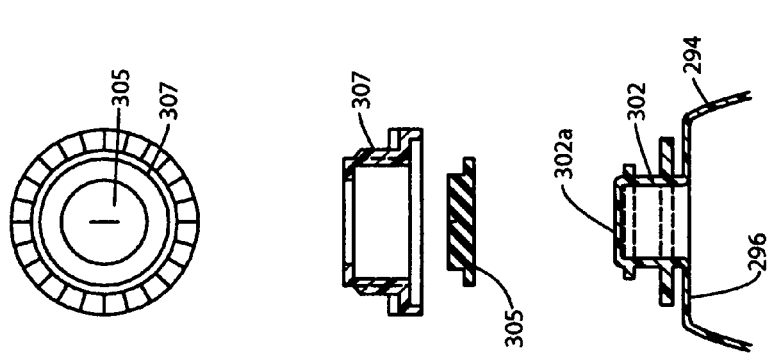
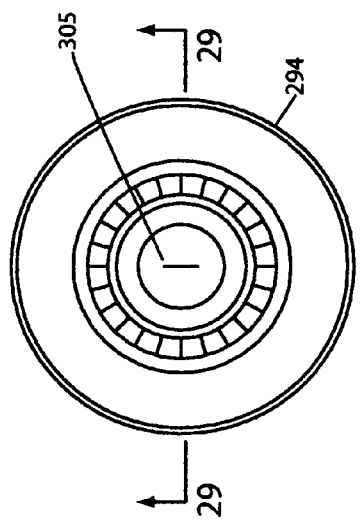
FIG. 28
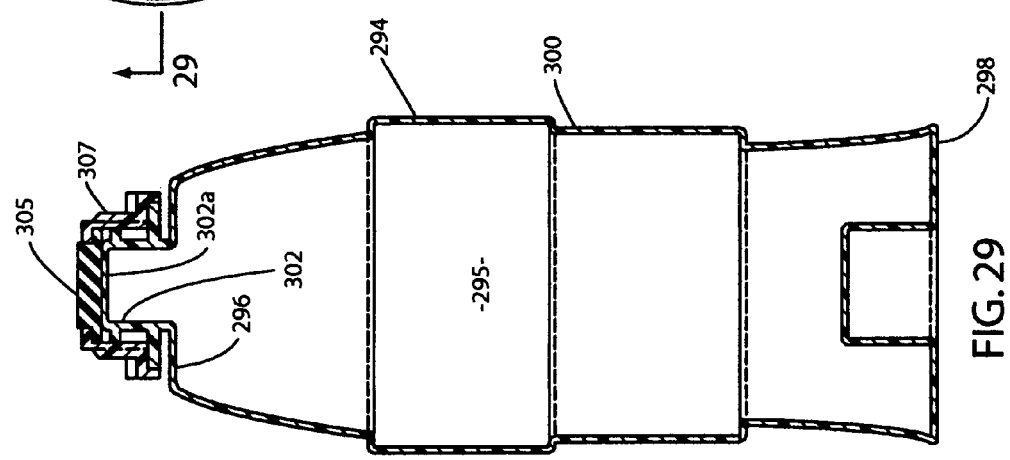

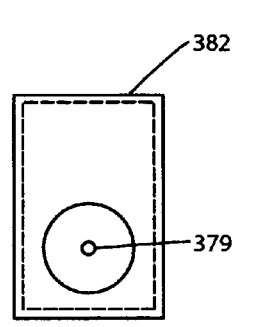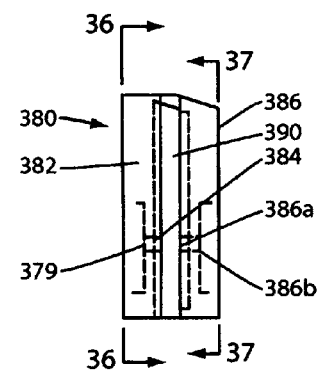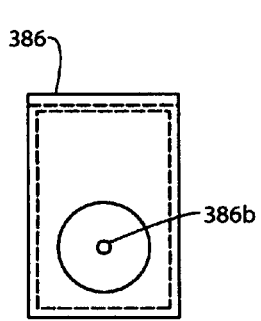
FIG. 36    FIG. 35    FIG. 37
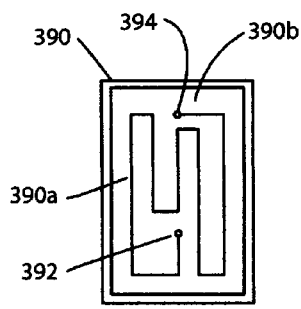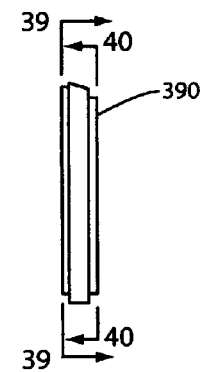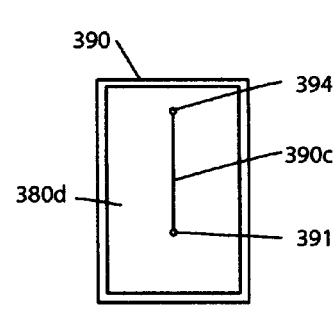
FIG. 39    FIG. 38    FIG. 40

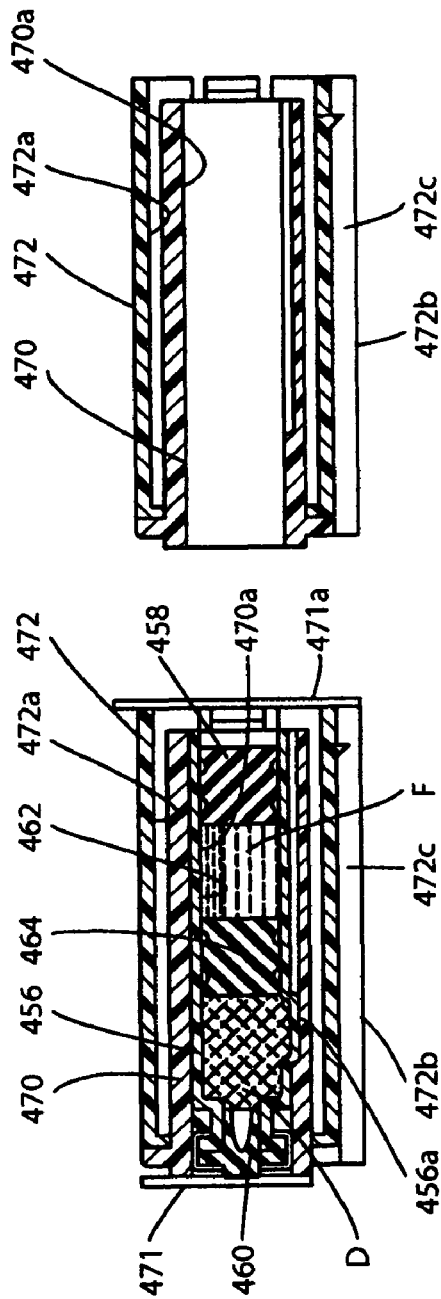
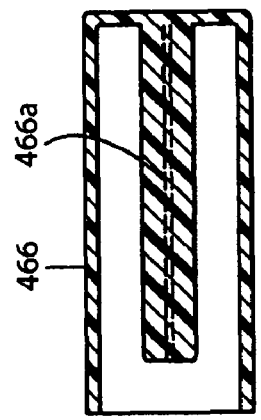
FIG.55
FIG.56

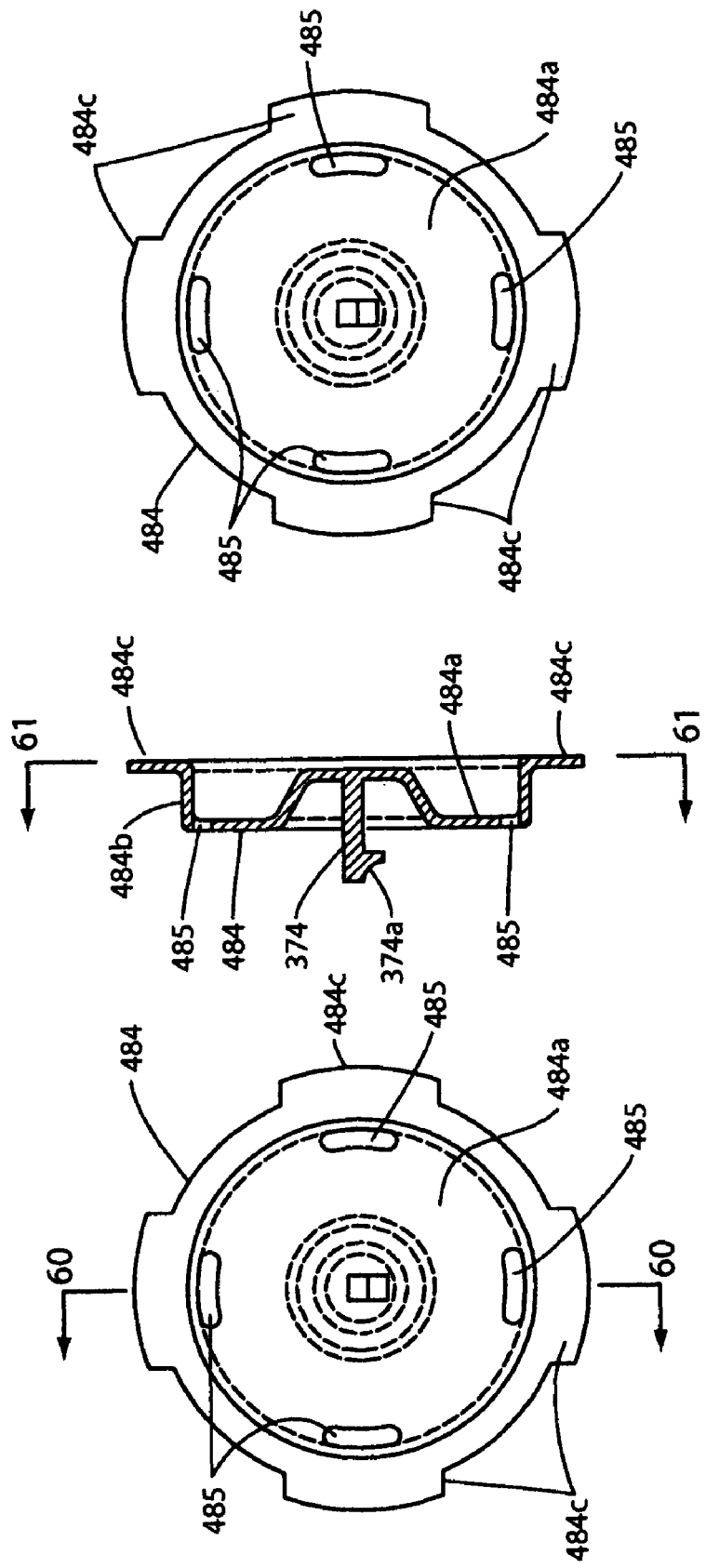

FLUID DISPENSER WITH ADDITIVE SUB-SYSTEM

This is a Continuation-in-Part of co-pending U.S. Ser. No. 11/823,084 filed Jun. 25, 2007.

BACKGROUND OF THE INVENTION

1. Field of the Invention

The present invention relates generally to fluid dispensing devices. More particularly, the invention concerns medicament dispensers for dispensing medicinal fluids to ambulatory patients.

2. Discussion of the Prior Art

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

The prior art gravity flow methods typically involve the use of intravenous administration sets and the familiar flexible solution bag suspended above the patient. Such gravimetric methods are cumbersome, imprecise and require bed confinement of the patient. Periodic monitoring of the apparatus by the nurse or doctor is required to detect malfunctions of the infusion apparatus. Accordingly, the prior art devices are not well suited for use in those instances where the patient must be transported to a remote facility for treatment.

As will be fully appreciated from the discussion that follows, the devices of the present invention are particularly useful in combat situations. The ability to quickly and efficaciously treat wounded soldiers, especially in unpredictable or remote care settings, can significantly improve chances for patient survival and recovery. Accurate intravenous (IV) drug and fluid delivery technologies for controlling pain, preventing infection, and providing a means for IV access for rapid infusions during patient transport are needed to treat almost all serious injuries.

It is imperative that battlefield medics begin administering life saving medications as soon as possible after a casualty occurs. The continuous maintenance of these treatments is vital until higher echelon medical facilities can be reached. A compact, portable and ready-to-use infusion device that could be easily brought into the battlefield would allow medics to begin drug infusions immediately. Additionally, it would free them to attend to other seriously wounded patients who may require more hands-on care in the trauma environment following triage. In most serious trauma situations on the battlefield, IV drug delivery is required to treat fluid resuscitation, as well as both pain and infection. Drug infusion devices currently available can impede the timely administration of IV infusions in remote care settings.

Expensive electronic infusion pumps are not a practical field solution because of their weight and cumbersome size. Moreover, today's procedures for starting IV infusions on the battlefield are often dangerous because the attending medic must complete several time consuming steps. The labor intensive nature of current gravity solution bag modalities can prevent medics from attending to other patients also suffering from life threatening injuries. In some cases, patients themselves have been forced to hold infusion bags elevated in order to receive the medication by gravity drip.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, biopharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

SUMMARY OF THE INVENTION

By way of brief summary, one form of the dispensing device of the present invention for dispensing medicaments to a patient comprises a supporting structure; a carriage assembly interconnected with the supporting structure for movement between a first position and a second position; a semi-rigid collapsible reservoir carried by the carriage assembly, the collapsible reservoir having an outlet port; guide means connected to the supporting structure for guiding travel of the carriage assembly between the first position and said second positions; a stored energy source operably associated with the carriage assembly for moving the carriage assembly between the first and second position; adding means for adding medicaments to the fluid within the fluid reservoir and an administration set including an administration line interconnected with the outlet port of the reservoir.

Another form of the dispensing device of the invention for dispensing medicaments to a patient is similar to that described in the preceding paragraph, but the dispensing device comprises two major cooperating components, namely a dispenser unit and a separate, stand alone additive sub-system.

With the forgoing in mind, it is an object of the present invention to provide a compact fluid dispenser for use in controllably dispensing fluid medicaments, such as, antibiotics, anesthetics, analgesics, and like medicinal agents from a pre-filled dispenser at a uniform rate.

Another object of the invention is to provide a small, compact fluid dispenser of simple construction that can be used in the field with a minimum amount of training.

Another object of the invention is to allow infusion therapy to be initiated quickly, at will, at point of care on the battlefield so that the attending medic or medical professional can more efficiently deal with triage situations in austere environments.

Another object of the invention is to provide a dispenser in which a stored energy source is provided in the form of a compressible, expandable or retractable member of novel construction that provides the force necessary to continuously and uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser of simple construction which includes a novel adding means for adding medicaments to the fluid contained within the fluid reservoir.

Another object of the invention is to provide a fluid dispenser as described in the preceding paragraph which embodies a semi-rigid collapsible container that includes a fluid reservoir that contains the beneficial agents to be delivered to the patient.

Another object of the invention is to provide a fluid dispenser of the class described which is compact and lightweight, is easy for ambulatory patients to use, is fully disposable and is extremely reliable in operation.

Another object of the invention is to provide a small, compact fluid dispenser that includes a housing to which vials can be connected for use in adding medicaments to the fluid within the fluid reservoir of the device.

Another object of the invention is to provide a fluid dispenser as described in the preceding paragraphs that is easy and inexpensive to manufacture in large quantities.

BRIEF DESCRIPTION OF THE DRAWINGS

FIG. 1 is a generally perspective, top view of one form of the fluid dispensing device of the present invention for dispensing medicaments to a patient.

FIG. 2 is a fragmentary, generally perspective bottom view of the front portion of the fluid dispensing device shown in FIG. 1.

FIG. 5 is a generally perspective, top view of an alternate form of the fluid dispensing device of the present invention for dispensing medicaments to a patient.

FIG. 6 is a fragmentary, generally perspective, bottom view of the front portion of the fluid dispensing device shown in FIG. 5.

FIG. 20 is a top view of the rate control knob of the fluid dispenser portion of the device.

FIG. 21 is a side view taken along lines 21-21 of FIG. 20.

FIG. 22 is a bottom view of the rate control knob of the fluid dispensing portion of the device.

FIG. 23 is a cross-sectional view taken along lines 23-23 of FIG. 22.

FIG. 24 is a cross-sectional view taken along lines 24-24 of FIG. 22.

FIG. 28 is a top view of the reservoir of the fluid dispenser portion of one embodiment of the device of the invention.

FIG. 29 is a cross-sectional view taken along lines 29-29 of FIG. 28.

FIG. 30 is an exploded, cross-sectional view of the upper neck portion of the reservoir of the fluid dispenser portion.

FIG. 35 is a front view of the rate control subassembly of the apparatus of this latest form of the invention.

FIG. 36 is a view taken along lines 36-36 of FIG. 35.

FIG. 37 is a view taken along lines 37-37 of FIG. 35.

FIG. 38 is a front view of the rate control plate of the rate control subassembly shown in FIG. 35 of the drawings.

FIG. 39 is a view taken along lines 39-39 of FIG. 38.

FIG. 40 is a view taken along lines 40-40 of FIG. 38.

FIG. 55 is a longitudinal, cross-sectional view of the additive sub-system of the form of the invention shown in FIG. 54.

FIG. 56 is a longitudinal, cross-sectional exploded view of the assemblage illustrated in the left portion of FIG. 55 of the drawings.

FIG. 59 is a bottom plan view of the carriage assembly of the dispenser unit illustrated in FIG. 58 of the drawings.

FIG. 60 is a cross-sectional view taken along lines 60-60 of FIG. 59.

FIG. 61 is a view taken along lines 61-61 of FIG. 60.

DESCRIPTION OF THE INVENTION

Figure 3:
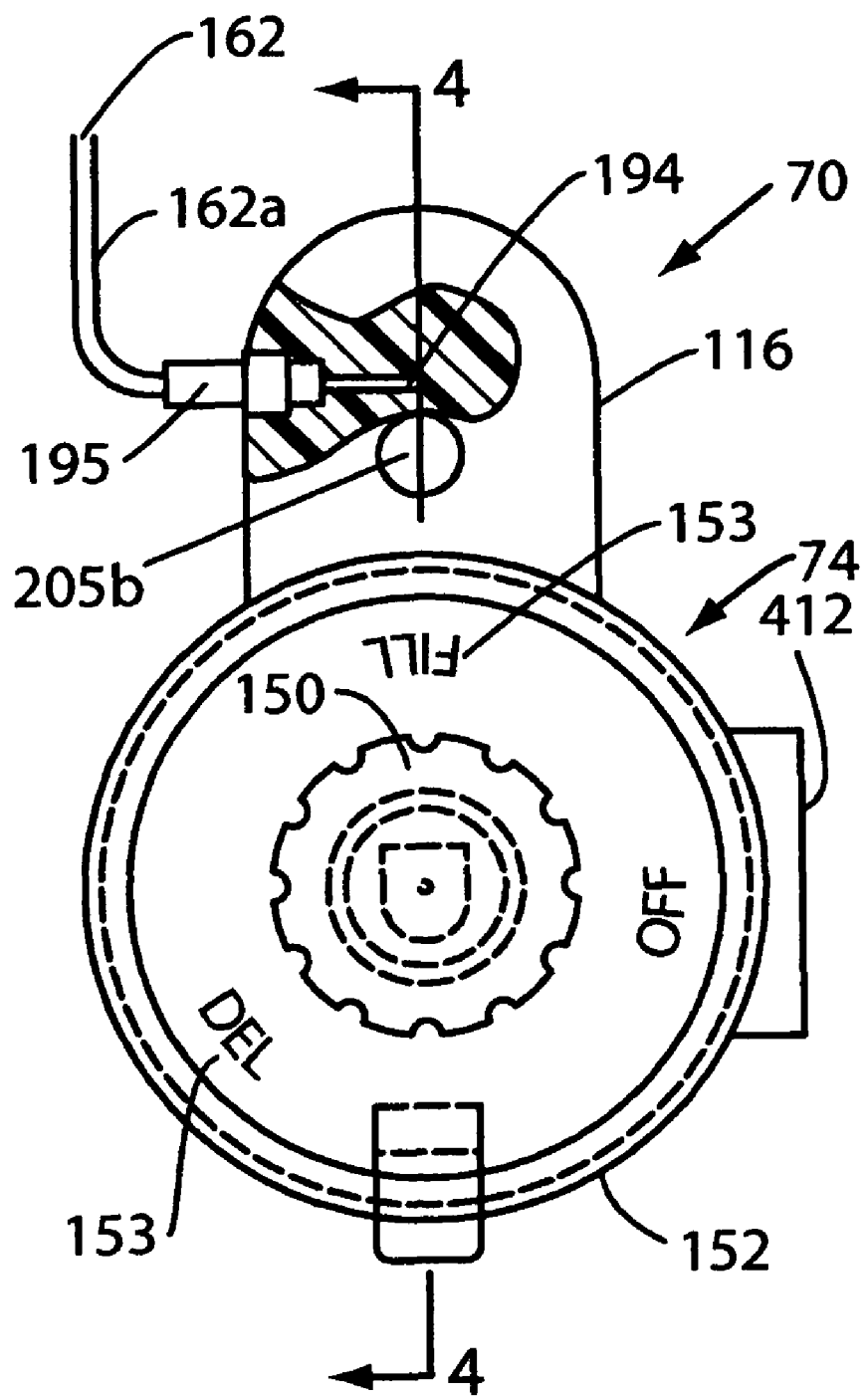
FIG. 3 is an enlarged front view of the fluid dispensing device shown in FIG. 1.

Referring to the drawings and particularly to FIGS. 1 through 4, one form of the dispensing device of the present invention for dispensing medicaments to a patient is there shown and generally designated by the numeral 70. The dispensing device here includes a housing 72, which includes a control portion 74 and a generally cylindrically shaped reservoir housing 76 that is interconnected with the control portion 74 in the manner best seen in FIG. 4 of the drawings. Housing 72 can be constructed from metal, plastic or any suitable material. Reservoir housing 76 includes a generally cylindrically shaped wall portion 76a and a base portion 76b.

Figure 4:
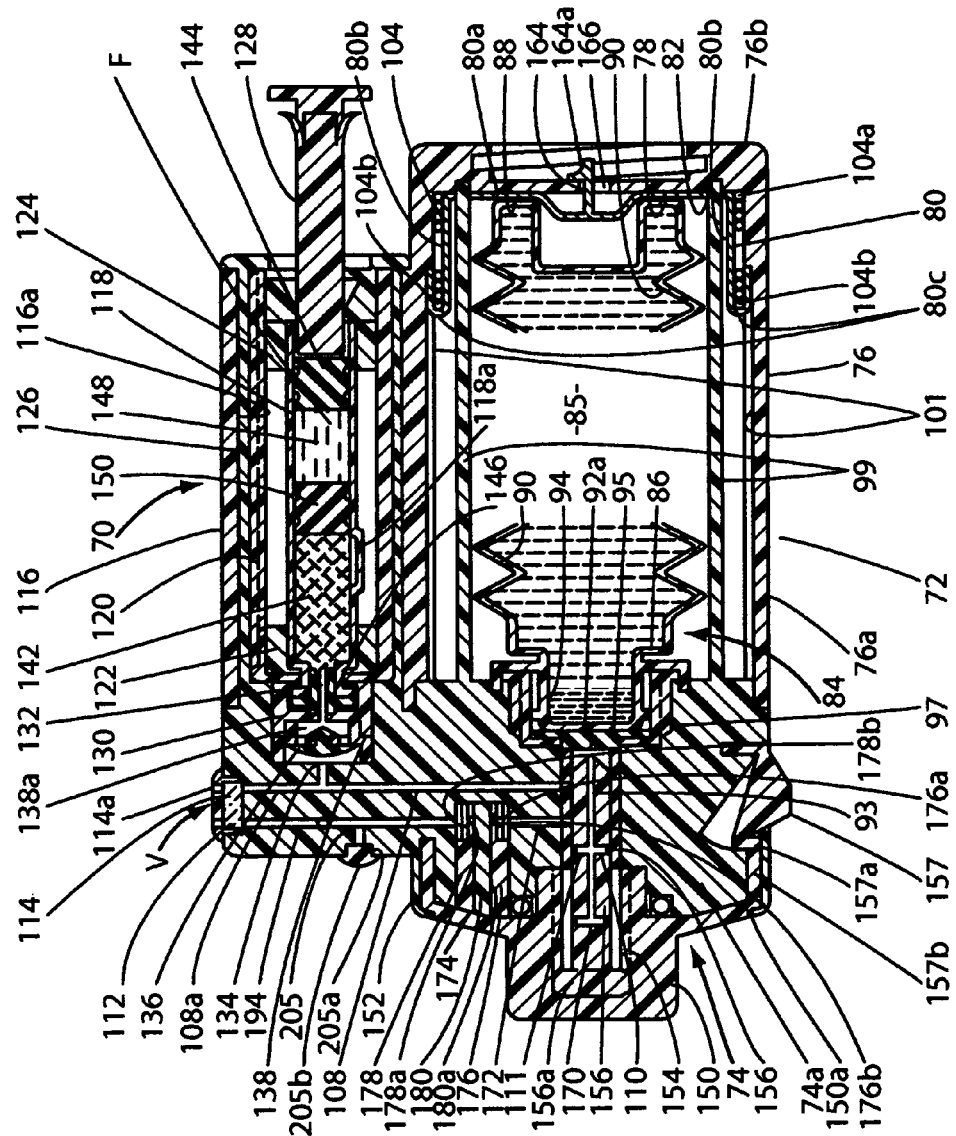
FIG. 4 is a cross-sectional view taken along lines 4-4 of FIG. 3.

Disposed within wall portion 76a is a carriage assembly 78, which is movable between a first position shown in FIG. 4 to a second fluid delivery position. As best seen by referring to FIG. 4, carriage assembly 78 comprises a carriage 80 having a carriage base 80a that is provided with a plurality of circumferentially spaced openings 82 and a generally cylindrically shaped sidewall 80b which terminates in circumferentially spaced, radially outwardly extending flanges 80c. Carriage assembly 78 is releasably locked in its first position by a novel locking means the character of which will presently be described.

Carried by carriage assembly 78 is a semi-rigid reservoir-defining assembly 84 that defines a fluid reservoir 85. As indicated in FIG. 4, reservoir-defining assembly 84 comprises a top wall 86, a bottom wall 88 and an accordion-like sidewall 90. Connected to top wall 86 is a neck portion 94 that is sealed by a closure wall 92a.

In the preferred form of the invention reservoir-defining assembly 84 is formed in accordance with an aseptic blow-fill seal manufacturing technique, which is of a character well understood by those skilled in the art. This technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding the molded container. Further details concerning the technique are available from Rommelag GMBH of Stuttgart, Germany and Weiler Engineering of Elgin, Ill.

In a manner presently to be described, a collapsible container is accessible via a penetrating member 93 that is adapted to pierce closure wall 92a as well as a pierceable membrane 95, which is positioned over closure wall 92a by means of a closure cap 97 which is affixed to the neck portion 94 of container assembly 84. As previously described, the basic container 84 is formed using the earlier described aseptic blow-fill technique and the reservoir portion of the container is sealed by the thin closure wall 92a. The piercable membrane 95 is then positioned over the closure wall and the closure cap 97 is positioned over the piercable septal membrane and secured to neck portion 94 by any suitable means such as adhesive bonding, sonic or heat welding.

An important feature of the invention resides in the provision of novel guide means for guiding travel of carriage assembly 78 between the first position shown in FIG. 4 and the second position. In the present form of the invention this important guide means comprises a plurality of circumferentially spaced guide members 99 which are connected to and extend outwardly from body 74a of control portion 74 (FIG. 4). As indicated in the drawings, guide members 99 are slidably received within openings 82 provided in carriage base 80a so that, as the carriage assembly travels from its first position toward its second position, guide members 99 precisely guide its travel. Also forming a part of the guide means of the apparatus of the present invention are a plurality of circumferentially spaced guide grooves 101 that are formed on the inner wall of outer housing 76 (FIG. 4).

To controllably move the carriage assembly from its first position to its second position, novel stored energy means are provided. This novel stored energy means, which is operably associated with carriage assembly 78, is here provided in the form of a coiled spring 104. As illustrated in FIG. 4, one end 104a of the coil spring 104 is disposed in engagement with the threaded base portion 76b of reservoir housing 76 and the other end 104b thereof is disposed in engagement with radially outwardly extending flange segments 80c of carriage 80. With this construction, following penetration of the reservoir septum, and when the locking means of the invention is manipulated in a manner to unlock the carriage assembly from base portion 76b of the outer housing, spring 104 will move from its retracted position shown in FIG. 4 to its expanded position, and in so doing will controllably move the carriage assembly from its starting position shown in FIG. 4 to its fully deployed or extended position. As will be described more fully in the paragraphs which follow, as the carriage assembly moves toward its deployed position, the accordion-like sidewall 90 of the reservoir-defining container will move into the collapsed configuration and in so doing will cause the medicinal fluid contained within the container to be controllably expelled therefrom.

Forming an important aspect of the apparatus of the present invention is adding means carried by portion 76 of housing 72 for adding injectable medicaments to the fluid within the fluid reservoir 85. The details of construction and operation of this important adding means will presently be discussed. As best seen in FIG. 4, body 74a of control portion 74 includes a fluid passageway 108 that is in communication with the fluid passageway of penetrating member 93 via passageways 110 and 111. Proximate its outer extremity 108a, fluid passageway 108 communicates with a cavity 112 formed within control portion 74 (See FIG. 4). Disposed within cavity 112 is a porous filter 114, which comprises a part of the vent means "V" of this latest form of the invention for venting to atmosphere any gasses that would otherwise be trapped within the fluid passageways of the device during the medicament-adding step. Filter 114, which is of a conventional construction such as a hydrophobic-treated, sintered metal or porous membrane, is held in position by a retainer 114a.

Control portion 74 of housing 72 also includes a vial housing 116 having a chamber 116a for telescopically receiving a medicament-containing reconstitution-type fill-vial 118. An elongated vial housing 120, which is disposed within chamber 116a, along with first and second spacers 122 and 124, function to hold vial 118 in a proper position within chamber 116a. Vial housing 120 is telescopically receivable within a vial tube 126, which in turn carries a pusher member 128, the purpose of which will presently be described. Also carried by control portion 74 in close proximity with vial housing 120 is a needle-holding component 130. As shown in FIG. 4, needle-holding component 130 carries a longitudinally extending, elongated hollow needle 132 having a flow passageway 132a that communicates with fluid passageway 108 via a stub passageway 134 and a conventional check valve 136 which is carried by a check valve housing 138. Vial 118, vial housing 120, vial tube 126, needle-holding component 130 and hollow needle 132 together comprise one form of the adding means of the device of the present invention. The method of operation of this important adding means will presently be described.

Referring particularly to FIG. 4, the medicament-containing fill-vial 118 comprises a container of special design that uniquely contains a lyophilized drug 142. Vial 118 is sealed at one end by a slidable elastomeric plunger 144 and at the other end by a pierceable septum 146. Formed intermediate the ends of the vial is a raised outer wall by-pass portion 118a, which permits the fluid "F" that is contained within a chamber 148 to bypass a barrier stopper 150 as the barrier stopper is urged inwardly of the container by pressure exerted thereon by the fluid, which is being pushed by plunger 144 resulting from force exerted on pusher element member 128 (see FIG. 4).

A continued inward pressure exerted on plunger 144 will cause fluid "F" to flow past barrier member 150 via the internal passageway defined wall portion 118a so as to reconstitute the lyophilized drug 142. A continued pressure exerted on plunger 144 by the pusher member will cause the reconstituted drug formed by the fluid "F" which has been intermixed with drug to flow through hollow needle 132, into a chamber 138a formed in check valve housing 138, past check valve 136, into a stub passageway 134, then into passageway 108 and finally into the device reservoir 85.

Device reservoir 85 and reconstitution medicament-containing fill-vial 118 can be of various volumes ranging from about 5 ml. to about 50 ml.

To control the flow of medicinal fluid from the adding means into the reservoir 85 and then, during the fluid dispensing step, out of reservoir 85 toward the administration set 162 of the invention, novel flow control means are provided. This novel fluid flow control means, which is housed within the control portion 74 of the device, here comprises two cooperating components, namely a rate control means for controlling the rate of fluid flow from the semi-rigid collapsible reservoir toward the administration set and an operating means for controlling fluid flow from the adding means into the reservoir 85 and then, after the reservoir has been filled, out of reservoir 85 toward the rate control means.

Considering first the operating means of the invention, this important means, which first controls fluid flow from the adding means toward the reservoir 85 and subsequently controls fluid flow between collapsible reservoir 85 and the rate control means, here comprises a control knob 150 that is rotatably mounted on body 74a of control portion 74. As best seen in FIG. 4, control knob 150 is held in position on body 74a by a knob retaining ring 152. Control knob 150, which is provided with control indicia 153 (FIG. 3), has an axial bore 154 having threads that threadably receive the head portion 156a of an elongated needle housing 156 that carries penetrating member 93. With this construction, an initial rotation of knob 150 will cause the needle housing 156 to controllably move from the position shown in FIG. 4 to a fill position wherein fluid passageway 111 aligns with fill passageway 108 formed in control body portion 74a. This initial rotation of control knob 150 will also cause penetrating member 93 to pierce both septal membrane 95 as well as closure wall 92a of the reservoir container. This movement of the housing 156 and the penetrating member 93 opens fluid communication between the fill-vial 118 and the fluid reservoir 85 via penetrating needle 132, the opened check valve 136, stub passageway 134, fill passageway 108, stub passageway 111 and the internal fluid flow passageway of penetrating member 93.

In the manner previously discussed, an inward force exerted on pusher member 128 will cause the fluid "F" to flow past barrier member 150 via the internal by-pass passageway defined by wall portion 118a so as to reconstitute the lyophilized drug 142. A continued pressure exerted on plunger 144 by the pusher member will cause the reconstituted drug formed by the fluid "F", which has been intermixed with the drug, to flow through penetrating needle 132 and then on to the fluid reservoir 85. After the reservoir is filled, check valve 136 will return to its initial closed position shown in FIG. 4 blocking reverse fluid flow from collapsible reservoir 85 toward fill-vial 118.

To prevent accidental rotation of control knob 150, indexing means, here provided in the form of an indexing button 157, functions to prevent rotation of the control knob until the indexing button, which is pivotally mounted on the side of the control portion of the device (FIG. 4), is pivoted inwardly. The skirt portion 150a of the control knob is provided with a plurality of circumferentially spaced notches 150b that closely receive a locking tab 157a formed on indexing button 157 when the button is biased toward its outward locking position. To accomplish the initial rotational step, described in the preceding paragraph, the indexing button 157 is pushed inwardly to move the locking tab 157a out of engagement with the notch within which it resides and the control knob is rotated from the "OFF" position (FIG. 3) to the "FILL" position. Release of the indexing button will then cause the outwardly biased locking tab 157a to move into engagement with an appropriate locking notch so as to lock the control knob in the "FILL" position.

After the diluent reservoir-filling step has been completed in the manner previously described, the fluid contained within the field reservoir can be dispensed to the patient by once again pivoting the indexing button 157 inwardly to move the locking tab 157a out of engagement with the notch within which it resides. This done, the control knob can be further rotated to the "DEL" position thereby causing the needle housing 156 to controllably move to the fluid delivery position. In this position fluid passageway 170 aligns with dispensing passageway 172 formed in control body portion 74a so that fluid can flow from reservoir 85 toward the administration set 162 via the flow rate control means of the invention the character of which will presently be described.

To cause the fluid to flow from reservoir 85 toward the flow rate control means, the locking means of the invention must be manipulated in a manner to release the carriage assembly from base wall 76b of reservoir housing 76. In this regard, as best seen in FIG. 4, the carriage locking means includes a locking member 164 having a yieldably deformable locking tab 164a which extends through a strategically shaped opening 166 provided in the base wall 76b of reservoir housing 76. With this construction, an inward force exerted on the locking member will deform the locking tab 164 in a manner to permit it to pass through the opening 166 and in so doing release the carriage from the base wall 76b. Release of the carriage will permit the stored energy means, or coiled spring 104, to move the carriage from a position shown in FIG. 4 into the extended position. As the semi-rigid accordion-like sidewall of the container collapses due to the urging of the coiled spring, the medicinal fluid contained within the container will be controllably expelled therefrom and will flow toward the fluid passageway of penetrating member 93 which has now moved into a downward position. From the fluid passageway of penetrating member 93, fluid will flow into a stub passageway 170 formed in needle housing 156. With the penetrating member 93 in its downward position stub passageway 170 is aligned with a passageway 172, which forms the inlet to the fluid rate control means of the invention.

The important fluid rate control means of the invention comprises a rate control housing 174, which includes a front cover 176 having an inlet 176a and an outlet 176b. Rate control housing 174 also includes a back cover 178 having an inlet 178a and an outlet 178b. Disposed between the front and back cover is a novel rate flow control plate 180 having a uniquely configured, circuitous fluid flow channel formed on one surface thereof and a substantially linear fluid flow channel formed on the second surface thereof.

With the construction described in the preceding paragraphs, as the accordion-like sidewall of the fluid container collapses in a controlled manner, fluid will flow from reservoir 85 into the flow passageway of penetrating member 93, into stub passageway 170 and then into the inlet passageway 172 of the rate control means. From passageway 172, the fluid will flow into the inlet 176a of front cover 176 and then into inlet 182 of flow control plate 180. The fluid will then flow through the circuitous fluid flow channel 180a, out the outlet 184 of the rate control channel and into the inlet of the linear fluid flow channel 180c. Next, the fluid will flow through outlet 188, into inlet 178a of back cover 178, outwardly through outlet 178b thereof and then into an elongated passageway 194 formed in body 74a of control portion 74. From the elongated channel 194 the fluid will flow onward to the administration set 162 and then to the patient. It is apparent that by varying the geometry, including the length, width and depth of the circuitous fluid flow control channel, the rate of fluid flow to the administration set and to the patient can be readily varied.

As best seen in FIG. 3, administration set 162 is sealably connected to the control portion 74 by a connector 195 so that the proximal end 162a of administration line 162 of the administration set is in communication with an outlet fluid passageway 194. Disposed between the proximal end 162a and the distal end 162b of the administration line are a conventional clamp 197, a conventional gas vent and a conventional filter 199 and an injector site 198. Provided at the distal end 162b of the administration line is a luer connector 201 and luer cap 203 of conventional construction (See FIG. 1).

To accomplish residual drug recovery from reservoir 85 as may be required, recovery means are provided. In this regard, as best seen in FIG. 4, a stub passageway 205 formed in body 74a also communicates with fluid passageway 194. Stub passageway 205 also communicates with a cavity 205a formed in body 74a. Sealably mounted within cavity 205a is a non-coring pierceable septum 205b (FIG. 4) which is pierceable by the needle of a conventional syringe which can be used to accomplish residual drug recovery from reservoir 85.

As illustrated in FIG. 1, housing 76 is provided with a belt clip receiving member 206 to which a belt clip 208 can be slidably interconnected. When the belt clip 208 is connected with receiving member 206 the device can be conveniently carried on the user's belt during the medicament dispensing step.

Figure 10:
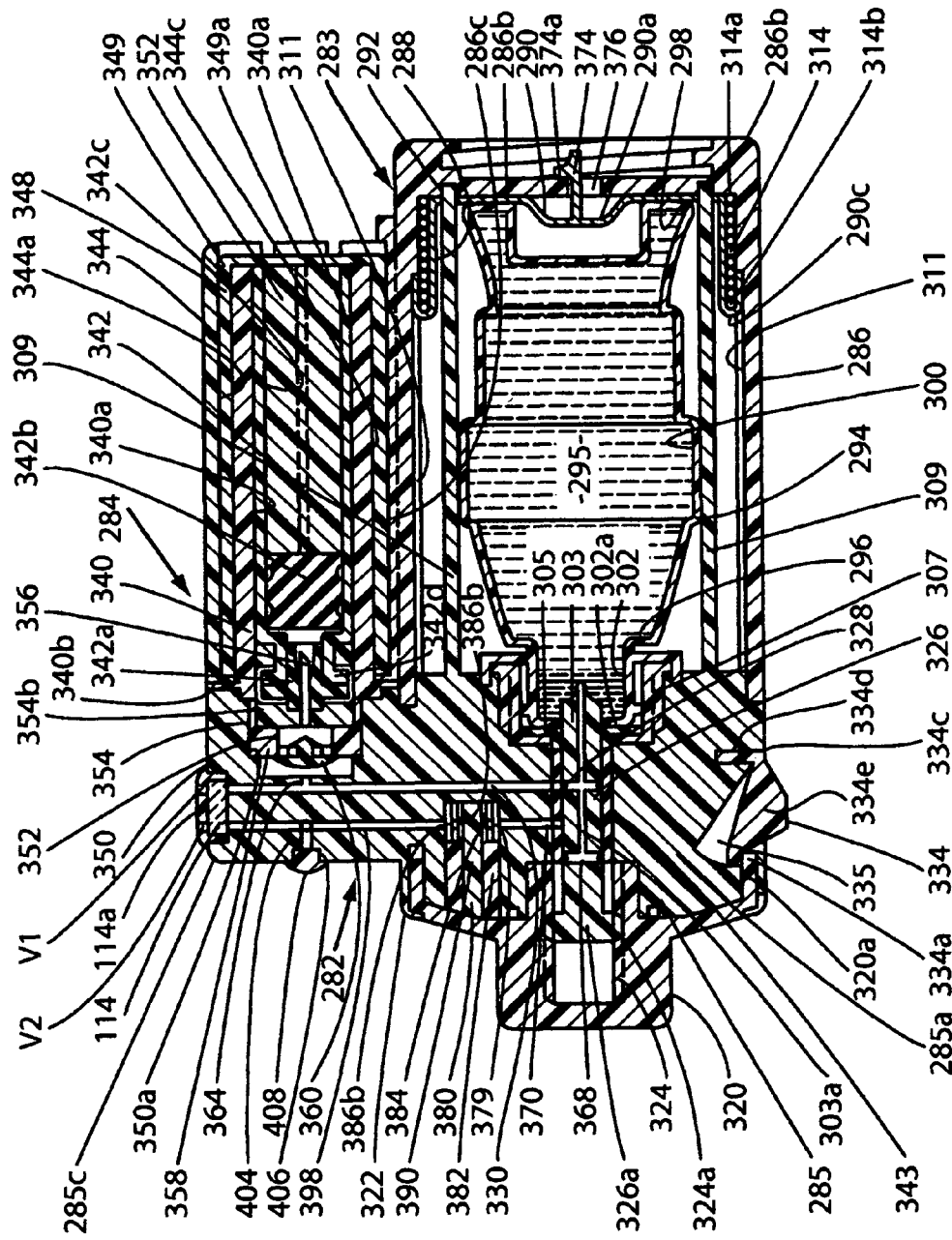
FIG. 10 is a longitudinal, cross-sectional view similar to FIG. 7, but showing the device in the reservoir fill mode with the additive sub-system of the device interconnected with the fluid dispenser.
Figure 11:
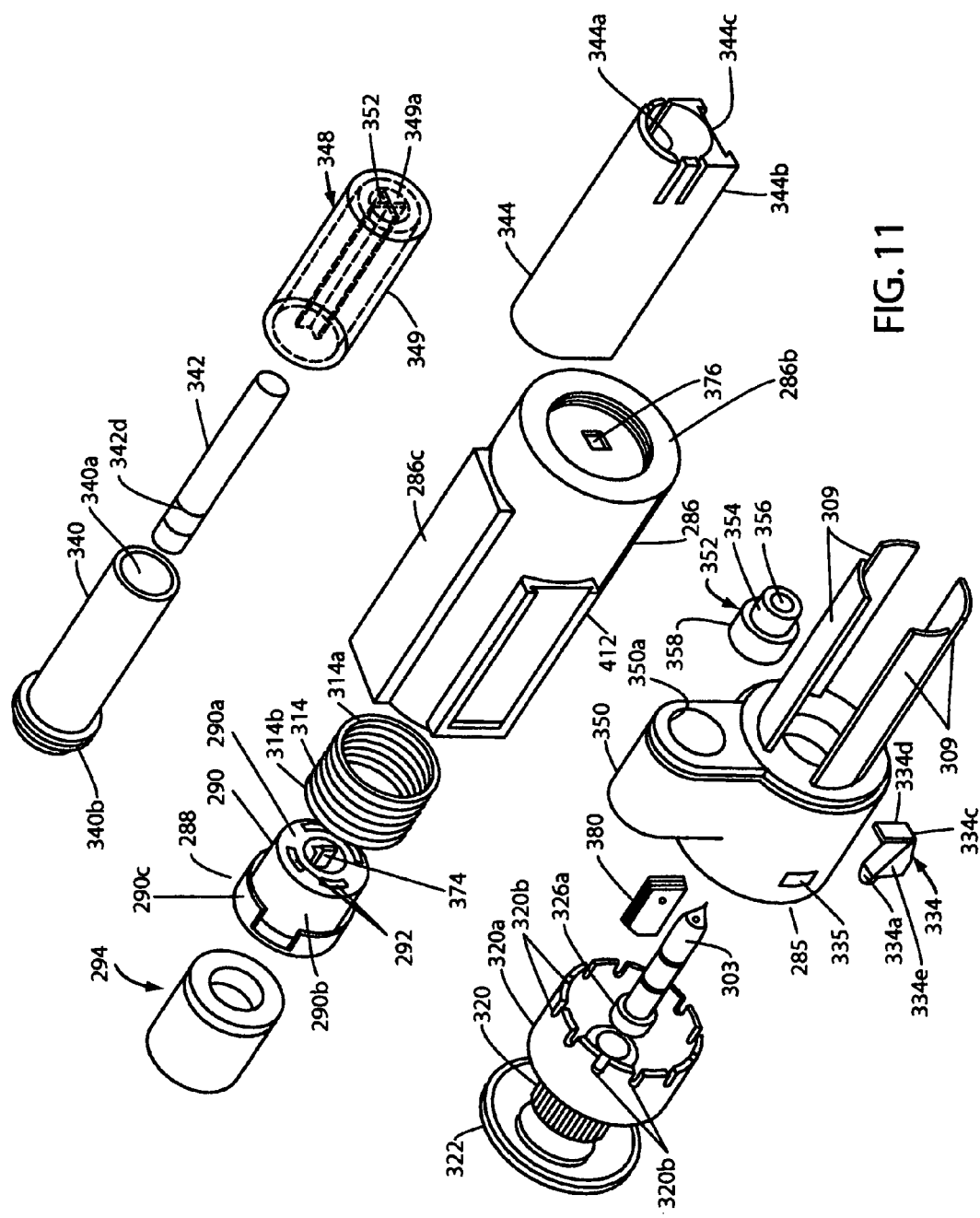
FIG. 11 is a generally perspective, exploded view of the fluid delivery dispenser illustrated in FIG. 7.
Figure 12:
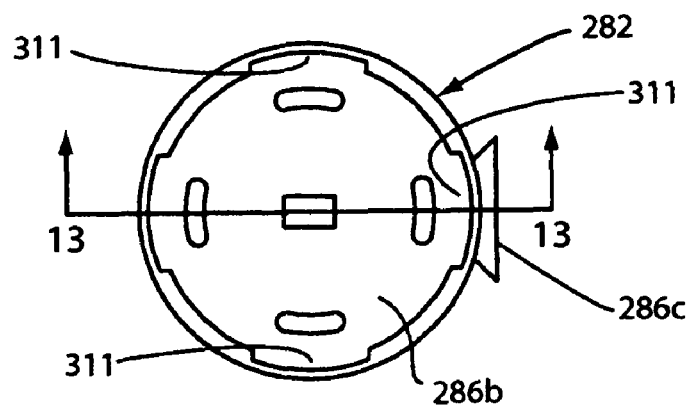
FIG. 12 is a top view of the reservoir housing of the fluid dispenser portion of the device.
Figure 13:
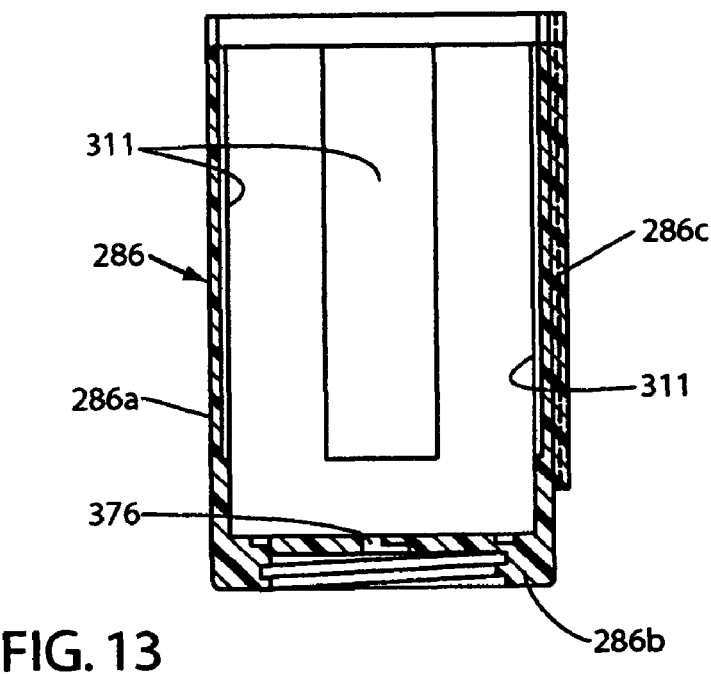
FIG. 13 is a cross-sectional view taken along lines 13-13 of FIG. 12.
Figure 14:
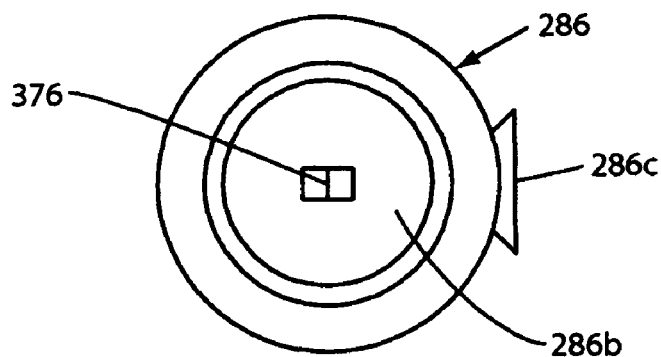
FIG. 14 is a bottom view of the reservoir housing of the fluid dispensing portion of the device.
Figure 15:
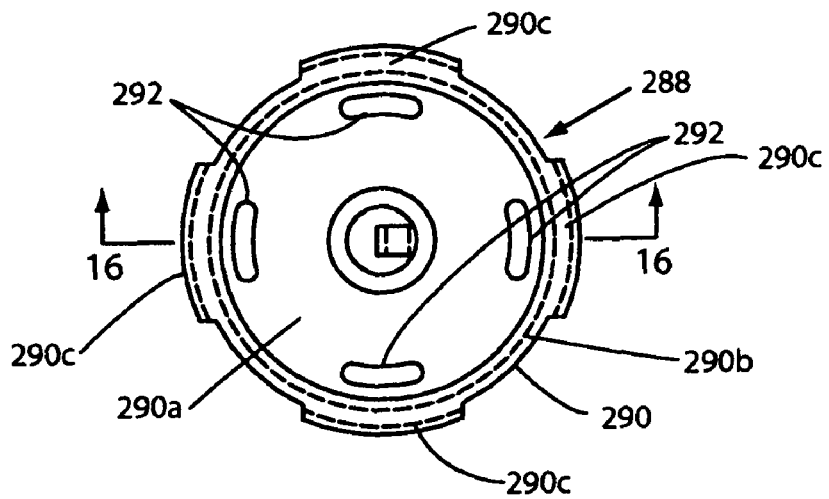
FIG. 15 is a top view of the reservoir carriage of the fluid dispenser portion of the device.

Referring now to FIGS. 5 through 16, an alternate form of the dispensing device of the present invention for dispensing medicaments to a patient is there shown and generally designated by the numeral 280. The apparatus of this latest embodiment is similar to that previously described, but the dispensing device here comprises two major cooperating components, namely a dispenser unit 282 and a separate, stand alone additive sub-system 284. Dispenser unit 282 includes an outer housing 283, which comprises a control portion 285 and a generally cylindrically shaped reservoir housing 286 that is interconnected with the control portion 285 in the manner best seen in FIG. 7 of the drawings. Additive sub-system 284, the details of construction and operation of which will presently be described, is also operably interconnected with the control portion 285 in the manner best seen in FIG. 10. As shown in FIGS. 12, 13 and 14, reservoir housing 286, which can be constructed from metal, plastic or any suitable material, includes a generally cylindrically shaped wall portion 286a and a base portion 286b.

Figure 7:
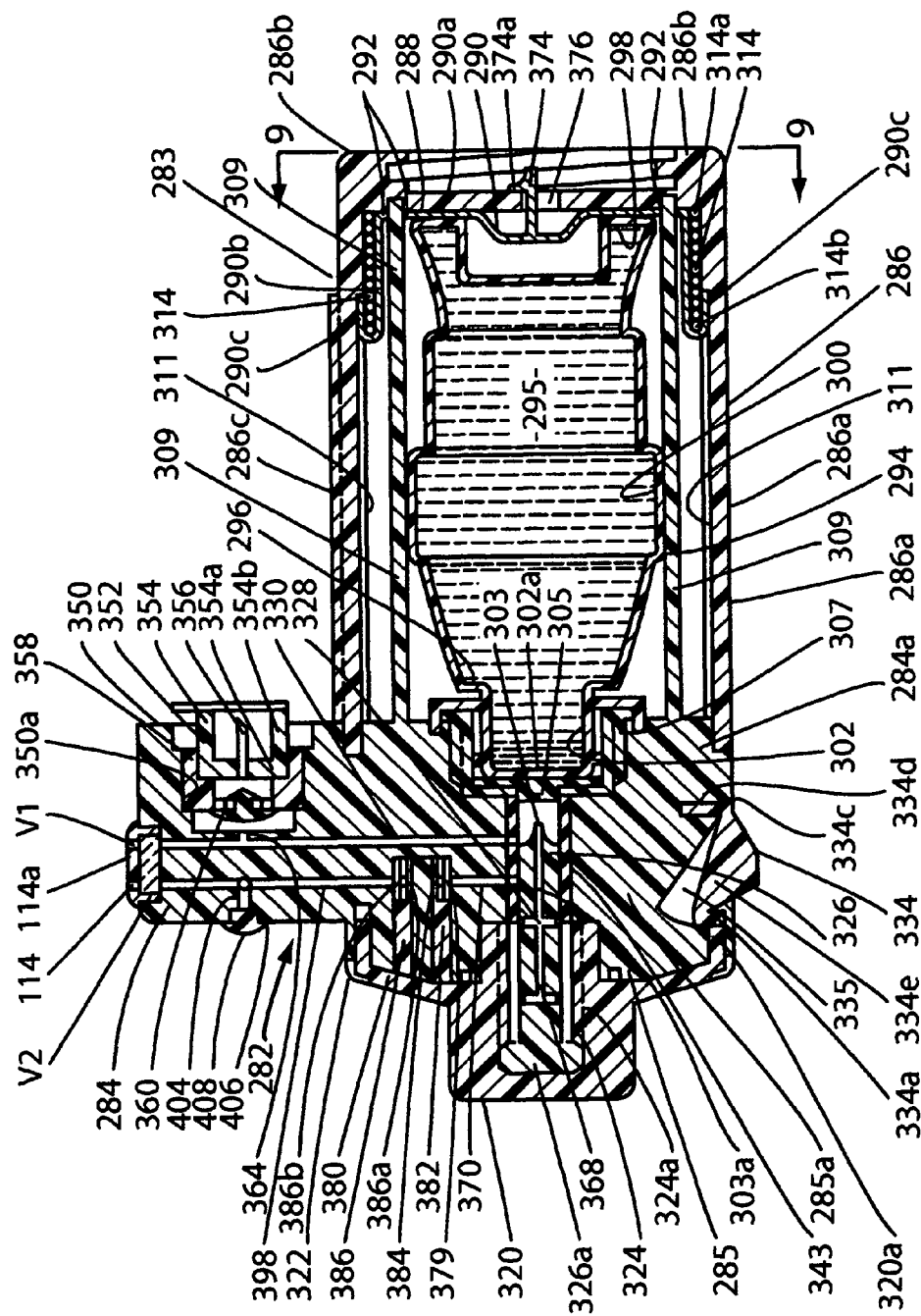
FIG. 7 is longitudinal, cross-sectional view of the fluid dispenser portion of the fluid dispensing device shown in FIG. 5.
Figure 34:
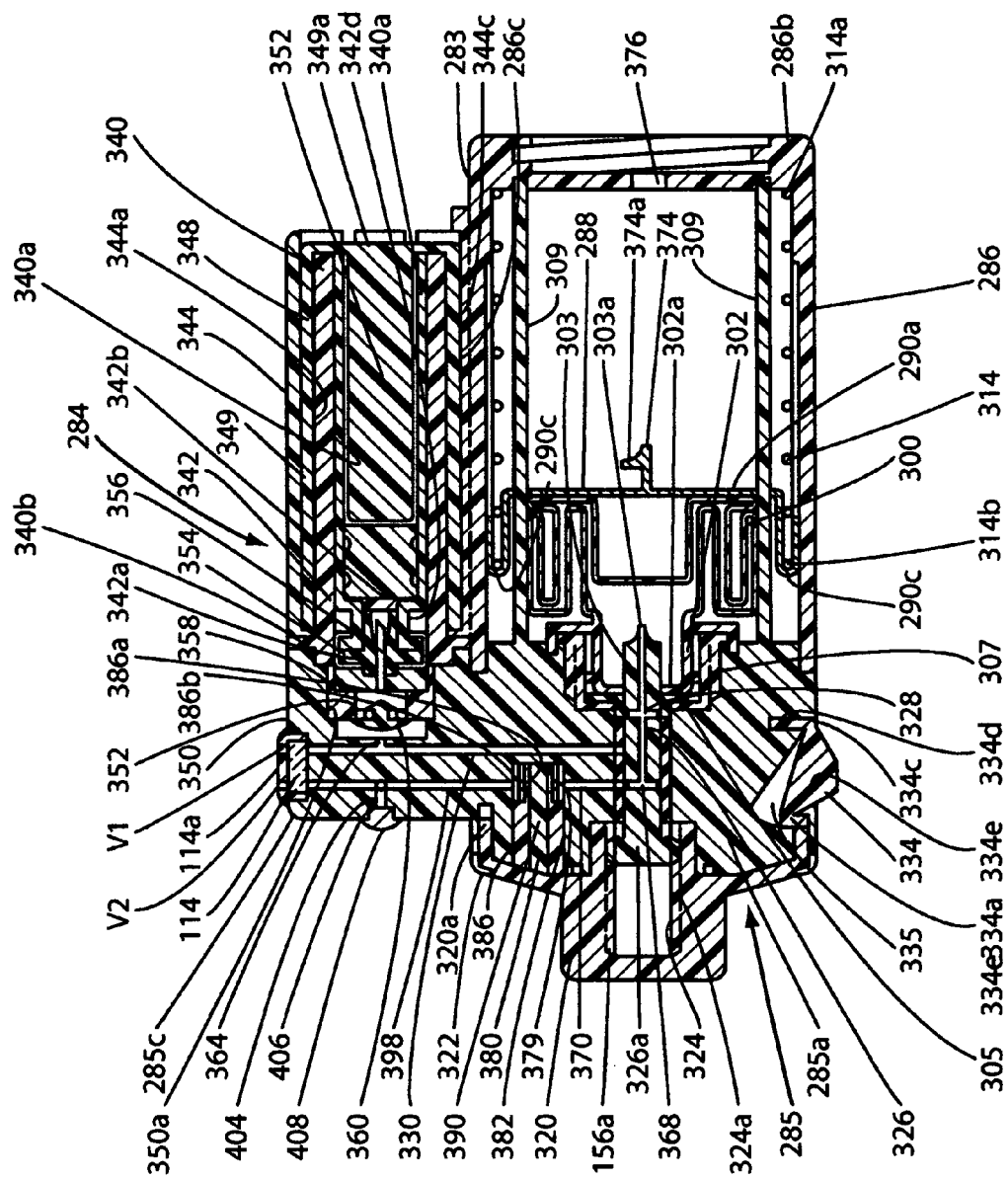
FIG. 34 is a longitudinal, cross-sectional view similar to FIG. 10, but showing the configuration of the dispenser following expelling of the fluid from the fluid reservoir.

Disposed within wall portion 286a is a carriage assembly 288 (FIGS. 7 through 17), which is movable between a first position shown in FIG. 7 and a second position shown in FIG. 34. As best seen by referring to FIGS. 7, 15, 16 and 17, carriage assembly 288 comprises a carriage 290 having a carriage base 290a that is provided with a plurality of circumferentially spaced openings 292 and a generally cylindrically shaped sidewall 290b which terminates in circumferentially spaced, radially outwardly extending flanges 290c. Carriage assembly 288 is releasably locked in its first position by a novel locking means the character of which will presently be described.

Carried by carriage assembly 288 is a reservoir-defining assembly 294 that defines a fluid reservoir 295. As indicated in FIGS. 7, 28, 29 and 30, reservoir-defining assembly 294 comprises a top wall 296, a bottom wall 298 and a telescoping sidewall 300. Connected to top wall 296 is a neck portion 302 that is sealed by a closure wall 302a (FIGS. 7, 29 and 30).

In the preferred form of the invention, reservoir-defining assembly 294 is formed in accordance with an aseptic blow-fill seal technique which is of a character well understood by those skilled in the art.

This technique involves the continuous extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding the molded container.

In a manner presently to be described, the collapsible container is accessible via a penetrating member 303 that is adapted to pierce closure wall 302a as well as a pierceable membrane 305 (FIGS. 29 and 30) which is positioned over closure wall 302a by means of a closure cap 307 which is affixed to the neck portion 302 of container assembly 294 (FIG. 29). As previously described, the basic container 294 is formed using the earlier described aseptic blow-fill technique and the reservoir portion of the container is sealed by the thin closure wall 302a. The piercable membrane 305 is then positioned over the closure wall and the closure cap 307 is positioned over the piercable membrane and secured to neck portion 302 by any suitable means such as adhesive bonding or sonic welding.

Figure 19:
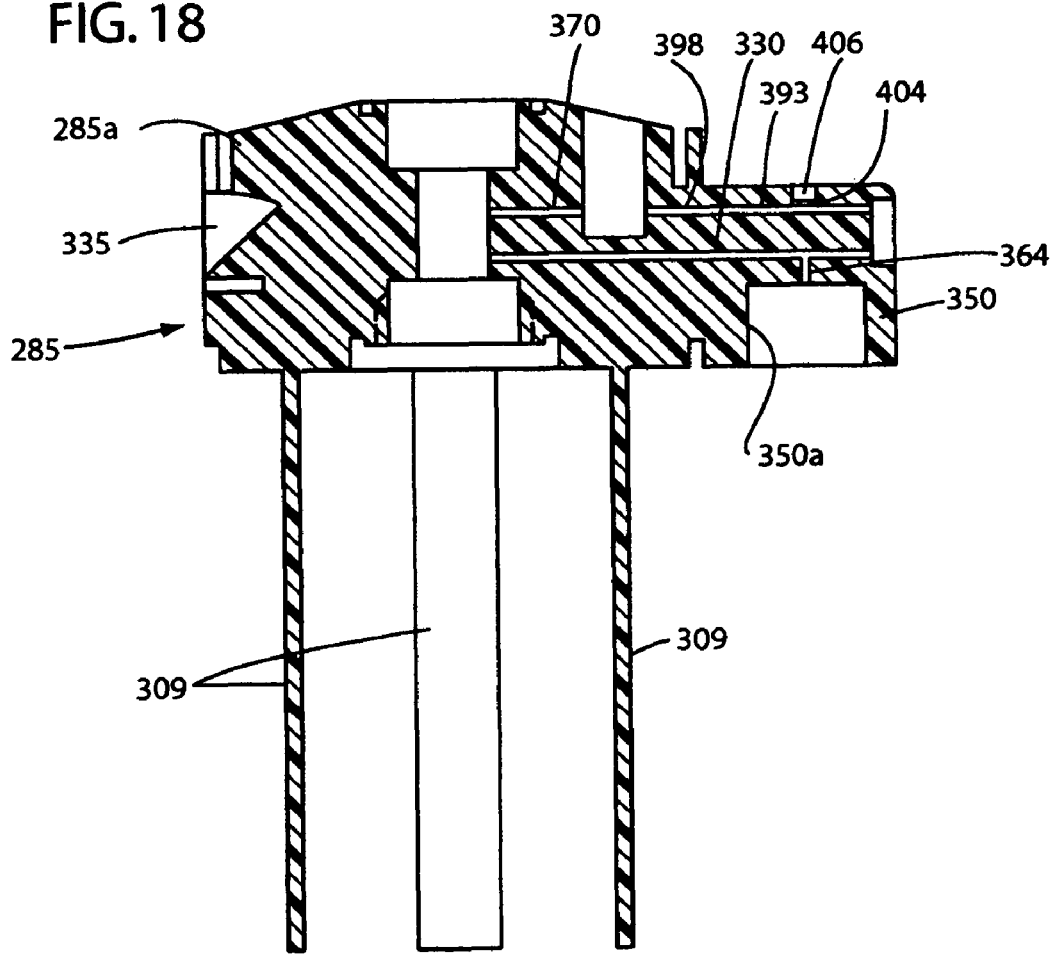
FIG. 19 is a cross-sectional view taken along lines 19-19 of FIG. 18.
Figure 25:
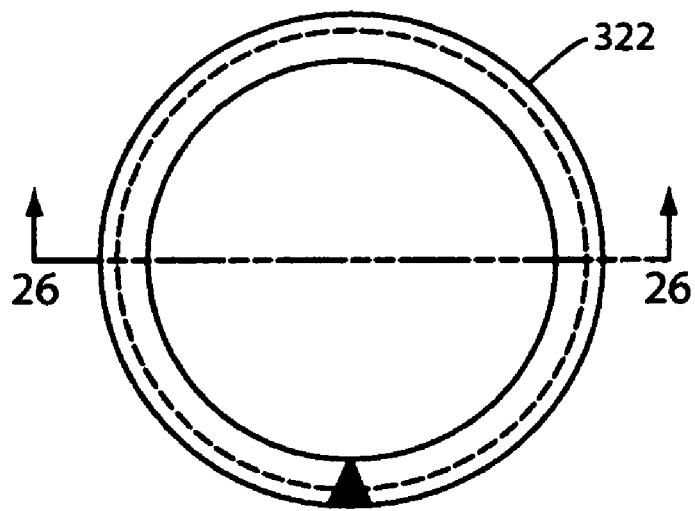
FIG. 25 is a top view of the rate control knob retaining ring of the fluid dispenser portion of the device.
Figure 26:
FIG. 26 is a cross-sectional view taken along lines 26-26 of FIG. 25.
Figure 27:
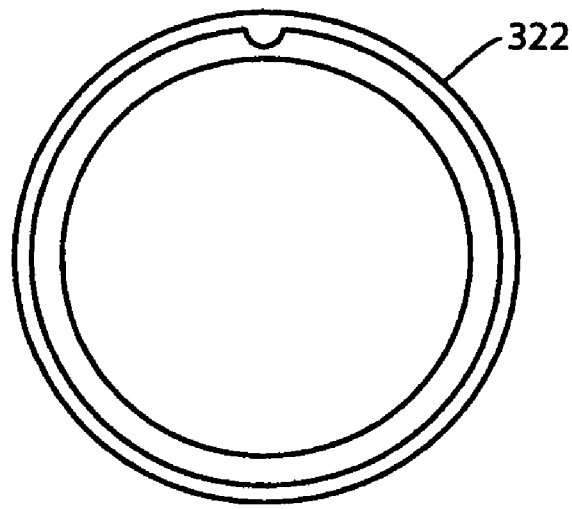
FIG. 27 is a bottom view of the rate control knob retaining ring of the fluid dispensing portion of the device.

An important feature of the invention resides in the provision of novel guide means for guiding travel of carriage assembly 288 between the first position shown in FIG. 7 and the second position shown in FIG. 34. In the present form of the invention this important guide means comprises a plurality of circumferentially spaced guide members 309 which are connected to and extend outwardly from body 285a of control portion 285 (FIGS. 11 and 19). As indicated in the drawings, guide members 309 are slidably received within openings 292 provided in carriage base 290a (FIG. 7) so that as the carriage assembly travels from its first position toward its second position, guide members 309 precisely guide its travel. Also forming a part of the guide means of the apparatus of the present invention are a plurality of circumferentially spaced guide grooves 311 that are formed on the inner wall of outer housing 286 (FIG. 7).

To controllably move the carriage assembly from its first position to its second position, novel stored energy means are provided. This stored energy means, which is operably associated with carriage assembly 288, is here provided in the form of a coiled spring 314. As illustrated in FIGS. 7, 10 and 34, one end 314a of the coil spring 314 is disposed in engagement with the threaded base portion 286b of reservoir housing 286 and the other end 314b thereof is disposed in engagement with radially outwardly extending flange segments 290c of carriage 290. With this construction, when, as will presently be described, the operating means of the invention has been operated in a manner to place the device in the fluid delivery mode and when the locking means of the invention is manipulated in a manner to unlock the carriage assembly from base portion 286b of the outer housing, spring 314 will move from its retracted position shown in FIG. 7 to its expanded position shown in FIG. 34. As the spring moves toward its expanded position it will controllably move the carriage assembly from its starting position shown in FIG. 7 to its fully deployed, or extended position shown in FIG. 34. As will be described more fully in the paragraphs which follow, as the carriage assembly moves toward its deployed position, the telescoping sidewall 300 of the reservoir-defining container will move into the collapsed configuration shown in FIG. 34 and in so doing will cause the medicinal fluid contained within the container to be controllably expelled therefrom.

To control the flow of medicinal fluid from the reservoir 295 toward the administration set 318 of the invention (FIG. 5), novel flow control means are provided. This novel fluid flow control means, which is housed within the control portion 285 of the device, here comprises two cooperating components, namely a rate control means for controlling the rate of fluid flow from the collapsible reservoir toward the administration set and the previously mentioned operating means for controlling fluid flow into and out of the fluid reservoir 295.

Considering first the operating means of the invention, this important means here comprises reservoir-accessing means for accessing the fluid reservoir 295 that includes a control knob 320 (FIGS. 5, 7, 20 and 21) that is rotatably mounted on body 285a of control portion 285 and penetrating means for penetrating both membrane 305 as well as closure wall 302a of the reservoir container. As best seen in FIGS. 5 and 6, the control knob 320 is held in position on body 285a by a knob retaining ring 322. Control knob 320, which is provided with control indicia 323 (FIG. 20), has an axial bore 324 having threads 324a that threadably receive the head portion 326a of an elongated needle housing 326 that carries penetrating member 303 of the previously identified penetrating means of the invention (FIGS. 7, 10 and 34). With this construction, an initial rotation of knob 320 will cause the needle housing 326 to controllably move from the position shown in FIG. 7 to the position shown in FIG. 10, wherein fluid passageway 328 aligns with passageway 330 formed in control body portion 285a.

As indicated in FIG. 10, rotation of control knob 320, will also cause penetrating member 303 to pierce both membrane 305 as well as closure wall 302a of the reservoir container. With the additive sub-system 284 interconnected with the dispenser unit in the manner shown in FIG. 10, this movement of the needle housing 326 and the penetrating member 303 opens fluid communication between the additive sub-system 284 and the fluid reservoir 295 via passageway 303, stub passageway 328 and the internal fluid flow passageway 303a of penetrating member 303.

To prevent accidental rotation of control knob 320, indexing means, here provided in the form of an indexing button 334, functions to prevent rotation of the control knob until the indexing button, which is pivotally mounted on the side of the control portion of the device (FIGS. 6 and 7), is pivoted inwardly of a cavity 335 formed in body 285a of control portion 285 (FIGS. 7 and 19). As illustrated in FIGS. 11, 21 and 22 of the drawings, the skirt portion 320a of the control knob is provided with a plurality of circumferentially spaced notches 320b that closely receive a locking tab 334a (FIG. 11), formed on indexing button 334 when the button is biased toward its outward locking position shown in FIG. 7 by a living hinge 334c that interconnects a finger 334d with the body portion 334e of the indexing button (FIG. 11). To accomplish the initial rotational step, described in the preceding paragraph, the indexing button 334 is pushed inwardly to move the locking tab 334a out of engagement with the notch 320b within which it resides and the control knob is rotated from the "OFF" position (FIG. 20) to the "ADD" position. Release of the indexing button will then cause the outwardly biased locking tab 334a to move into engagement with an appropriate locking notch so as to lock the control knob in the "ADD" position.

Figure 8:
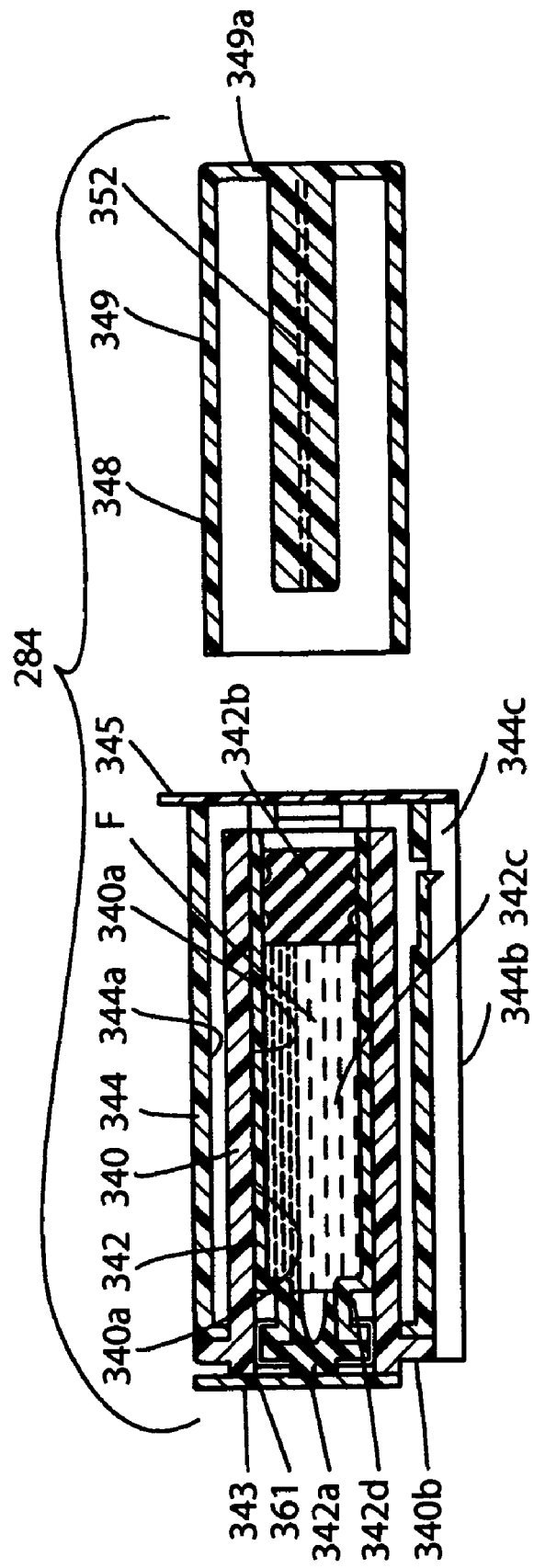
FIG. 8 is a longitudinal, cross-sectional view of the additive sub-system of the fluid dispensing device shown in FIG. 5.

Considering now the details of the construction and operation of the important additive sub-system 284, as best seen in FIG. 8, additive sub-system 284 here comprises a generally tubular-shaped vial housing 340 having a chamber 340a for telescopically receiving a medicament-containing, cartridge-type fill vial assembly 342. Chamber 340a is initially sealed at one end by a seal cover 343 and at the other end by a seal cover 345. In the present form of the invention, dispenser reservoir 295 and medicament-containing vial of the vial assembly 342 can be of various volumes ranging from about 5 ml to about 50 ml.

As shown in FIG. 8, vial housing 340 is carried within a connector housing 344 having an internal chamber 344a. A collar portion 340b formed on vial housing 340 functions to hold vial assembly 342 in a proper position within chamber 344a. Formed in the lower surface 344b of connector housing 344 is a dovetail receiving groove 344c (FIG. 11), the purpose of which will presently be described. Also forming a part of the additive sub-system 284 of the invention is a pusher assembly 348 that includes an elongated outer casing 349 having an end wall 349a and a pusher member 352 that is integrally formed with and extends inwardly from end wall 349a. As will be discussed hereinafter, during the medicament-adding step, and following the removal of sterile cover 345, pusher assembly 348 is telescopically movable inwardly of internal chamber 344a of connector housing 344 in the manner shown in FIG. 10.

Figure 9:
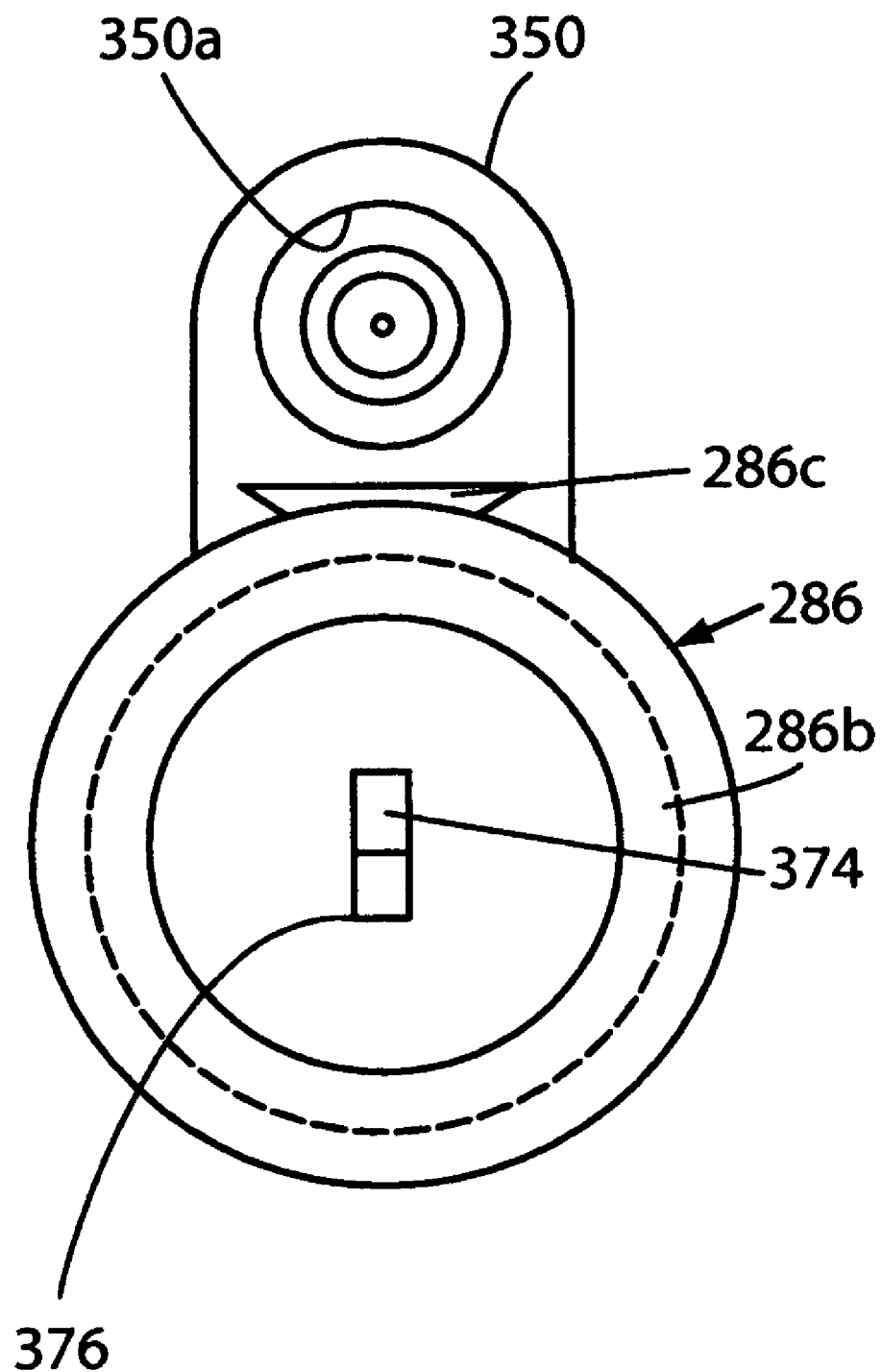
FIG. 9 is a view taken along lines 9-9 of FIG. 7.
Figure 32:
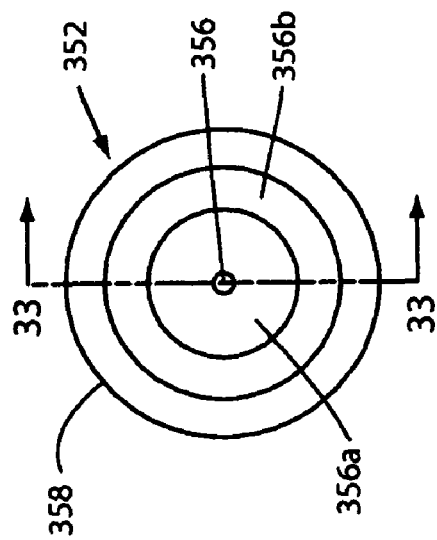
FIG. 32 is a bottom view of the check valve assembly of the fluid dispensing portion of the device.
Figure 33:
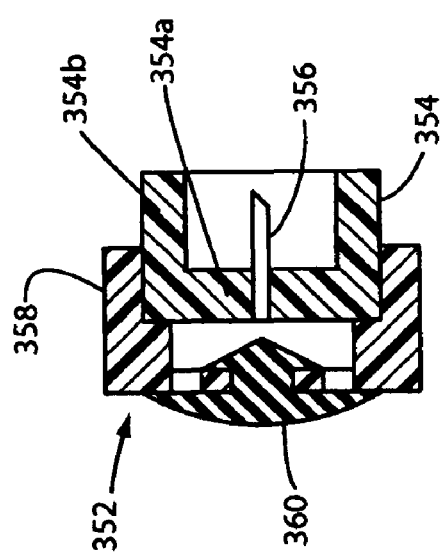
FIG. 33 is a cross-sectional view taken along lines 33-33 of FIG. 32.
Figure 31:
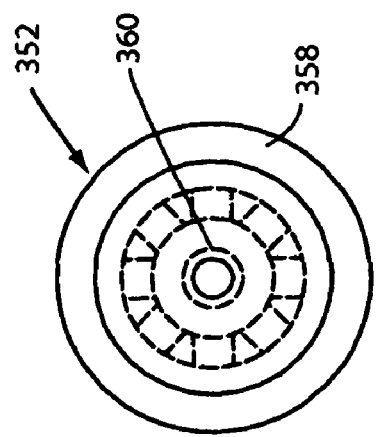
FIG. 31 is a top view of the check valve assembly of the fluid dispenser portion of the device.

Following the removal of sterile cover 343, the additive sub-system 284 of the device can be interconnected with the control portion 285c of the dispenser unit in the manner illustrated in FIG. 10. More particularly, as shown in FIGS. 9 and 11 reservoir housing 286 is provided with a dovetail connector segment 286c that is slidably received within the groove 344c formed in connector housing 344. Additionally, as seen in FIGS. 10 and 19, control portion 285 of the dispenser includes a connector segment 350 that is provided with a check valve cavity 350a. Mounted within cavity 350a is a check valve assembly 352, the construction of which is best seen in FIGS. 31, 32 and 33. Forming a part of assembly 352 is a needle housing 354 having a needle base 354a, a generally cylindrical skirt 354b and a penetrating needle 356 that is connected to and extends outwardly from needle base 354a. Also forming a part of assembly 352 is a check valve housing 358 that carries an elastomeric umbrella-type check valve 360.

As indicated in FIG. 10, when the dovetail connector segment 286c is mated with and urged forwardly of the dovetail receiving groove 344c formed in connector housing 344, skirt 354b will be telescopically received within the inboard end 361 of internal chamber 344a of connector housing 344. Then, as the vial 342 is urged inwardly of chamber 340a of vial housing 340 by the pusher member 352, needle 356 will pierce the pierceable septum 342a of the vial assembly 342 in the manner shown in FIG. 10.

Following the mating of the additive sub-system 284 with the dispenser unit 282, continuous pushing movement of the pusher assembly 348 into chamber 344a will cause pusher 352 to move the elastomeric plunger 342b of the vial assembly inwardly of the fluid chamber 342c in a direction toward the second, or closed end 342d of the vial 342 (see FIG. 10). As the plunger is moved inwardly of the fluid chamber 342c, the fluid "F" contained within the fluid chamber will be expelled therefrom into the hollow needle 356. As best seen in FIG. 10, the fluid will then flow past conventional elastomeric umbrella-type check valve 360, which is mounted within check valve housing 358. Next, the fluid will flow into a stub passageway 364 and thence into passageway 330. Umbrella-type check valve 360 functions in a conventional manner to control fluid flow from the hollow needle 356 toward fluid passageway 330. From passageway 330, the fluid will flow into inlet passageway 328 and then into reservoir 295 of the container via the central passageway 303a of penetrating member 303. During the adding process, any gases trapped within the flow passageways of the device are vented to atmosphere via a vent "V-1" formed in connector segment 350.

Following the completion of the adding process as described in the preceding paragraph wherein the fluid medicament "F" contained within vial 342 is added to the reservoir 295, the operating means is used to control the flow of the fluid mixture from the collapsible reservoir toward the rate control means and then onward toward the administration set. More particularly, to accomplish this fluid dispensing step, the indexing button 334 is once again pushed inwardly of cavity 335 to move the locking tab 334a out of engagement with the notch within which it resides and the control knob is rotated from the "ADD" position (FIG. 20) to the "DISP" position. Release of the indexing button will then cause the outwardly biased locking tab 334a to move into engagement with an appropriate locking notch so as to lock the control knob in the "ADD" position.

Further rotation of control knob 320, will also cause penetrating member 303 to move further inwardly to the position illustrated in FIG. 34, wherein a stub passageway 368 formed in penetrating member 303 aligns with a fluid flow passageway 370 formed in control portion 285a. With the penetrating member 303 in this advanced position fluid communication between the fluid reservoir 295 and the rate control means of the device is established via fluid flow passageway 303a of penetrating member 303.

To cause the fluid to flow from reservoir 295 toward the flow rate control means, the locking means of the invention must be manipulated in a manner to release the carriage assembly from base wall 286b of reservoir housing 286. In this regard, as best seen in FIGS. 7, 9, 10 and 16, the carriage locking means includes a locking member 374 having a yieldably deformable locking tab 374a which extends through a strategically shaped opening 376 provided in the base wall 286b of reservoir housing (see FIGS. 7 and 9). With this construction, an inward force exerted on the locking member will deform the locking tab 374 in a manner to permit it to pass through the opening 376 and in so doing release the carriage from the base wall 286b. Release of the carriage will permit the stored energy means, or coiled spring 314, to move the carriage from a position shown in FIGS. 7 and 10 into the position shown in FIG. 34.

As the telescoping sidewall of the container collapses due to the urging of the coiled spring, the medicinal fluid mixture contained within the reservoir 295 will be controllably expelled therefrom and will flow toward the fluid passageway 303a of penetrating member 303 which has now moved into the position shown in FIG. 10 of the drawings. From the fluid passageway of penetrating member 303 fluid will flow into a stub passageway 368 into passageway 370 and then into the inlet 379 of the fluid rate control means of the invention.

The important fluid rate control means of the invention, which is illustrated in FIGS. 36, 37 and 38 of the drawings, comprises a rate control housing 380, which includes a front cover 382 having the previously identified inlet 379 and an outlet 384. Rate control housing 380 also includes a back cover 386 having an inlet 386a and an outlet 386b. Disposed between the front and back cover is a novel rate control plate 390 having a uniquely configured, circuitous fluid flow channel 390a formed on the first surface 390b thereof and a substantially linear fluid flow channel 390c formed on the second surface 380d thereof (FIG. 40).

With the construction described in the preceding paragraphs, as the sidewall of the fluid container collapses (FIG. 34), fluid will flow from reservoir 295 into the flow passageway of penetrating member 303, into stub passageway 368, then into passageway 370 and then into the inlet passageway 379 of the rate control means. From passageway 379, the fluid will flow into the front cover 382, through the outlet 384 and then into inlet 392 of fluid flow channel 390a. The fluid will then flow through the rate control channel, out the outlet 394 of the rate control channel and into the inlet 386a of back cover 386, outwardly through outlet 386b thereof, into substantially linear fluid flow channel 390c formed on the second surface 380d of rate control plate 390, out through outlet 391 thereof and then into an elongated passageway 398 formed in body 285a of control portion 285. From the elongated channel 398 the fluid will flow onward to the administration set 318 and then to the patient. It is apparent that by varying the geometry, including the length, width and depth of the flow control channels 390a and 390c, the rate of fluid flow to the administration set and to the patient can be readily varied. During the fluid dispensing process, any gases trapped within the fluid delivery passageways of the device are vented to atmosphere via a vent "V-2" formed in connector segment 350.

As indicated in FIG. 5, administration set 318 is sealably connected to the control portion 285 by any suitable means so that the proximal end of the administration line 318a of the administration set is in communication with an outlet fluid passageway in communication with passageway 398 (FIG. 7). Disposed between the proximal end and the distal end of the administration line are a conventional clamp 405, a conventional gas vent and filter 407 and a conventional "Y"-site 409. Provided at the distal end of the administration line is a luer connector 411 of conventional construction.

To accomplish residual drug recovery from reservoir 295 as may be required, recovery means are provided. In this regard, as best seen in FIGS. 7 and 34 a stub passageway 404 formed in body 285a also communicates with fluid passageway 398. Stub passageway 404 also communicates with a cavity 406 formed in body 285a (FIG. 34). Sealably mounted within cavity 406 is a pierceable septum 408 which is pierceable by the needle of a conventional syringe that can be used to accomplish residual drug recovery from reservoir 295.

As illustrated in FIG. 5, housing 286 is provided with a belt clip receiving member 412 to which a belt clip 414 can be slidably interconnected. When the belt clip 414 is connected with receiving member 412 the device can be conveniently carried on the user's belt during the adding and medicament dispensing steps.

Referring to FIGS. 41 through 50, an alternate form of the fluid dispensing device of the present invention for dispensing medicaments to a patient is there shown. This alternate form of dispensing device is similar in most respects to that shown in FIGS. 5 through 40 and like numerals are used in FIGS. 41 through 50 to identify like components. The major difference between this latest embodiment of the invention and that shown in FIGS. 5 through 40 resides in the differently configured additive sub-system.

Figure 41:
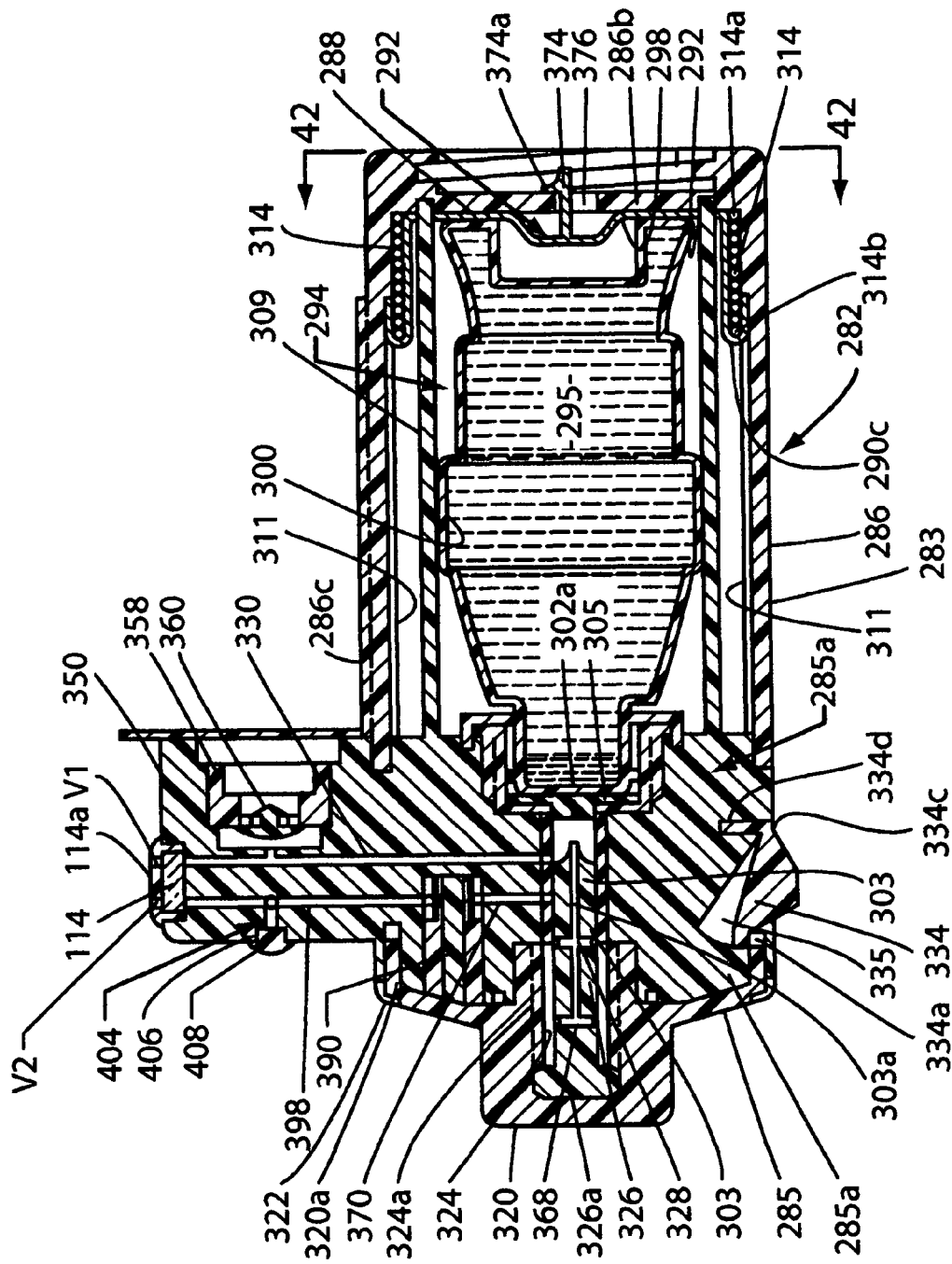
FIG. 41 is a longitudinal, cross-sectional view of the fluid dispenser component of still another form of the apparatus of the invention.
Figure 42:
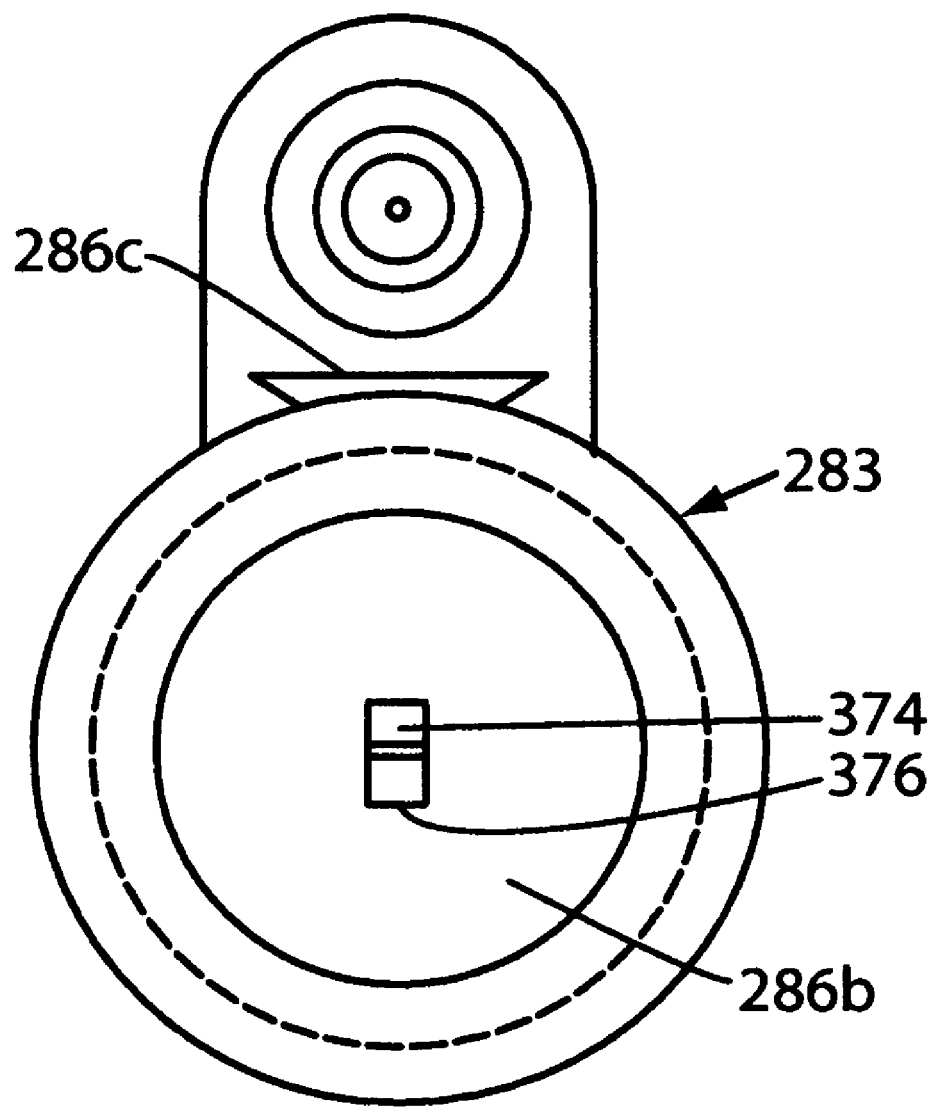
FIG. 42 is a view taken along lines 42-42 of FIG. 41.
Figure 43:
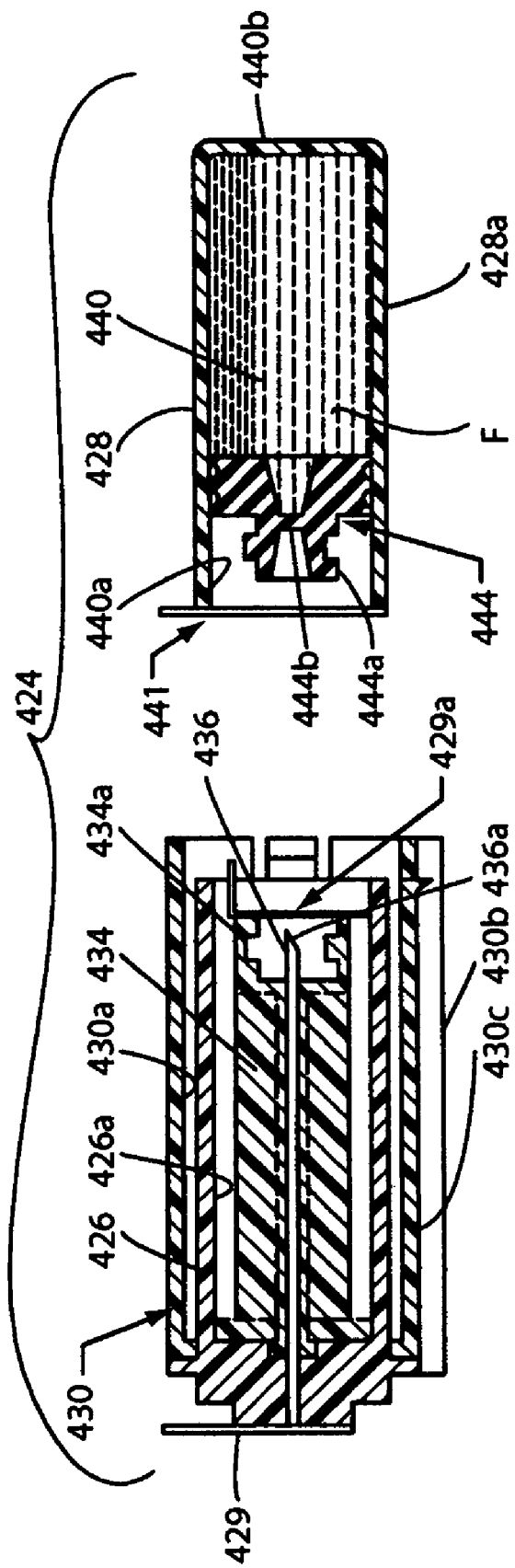
FIG. 43 is an exploded, cross-sectional view of an alternate form of the additive sub-system of the apparatus of the invention that is adapted to mate with the fluid dispenser component illustrated in FIG. 41.
Figure 44:
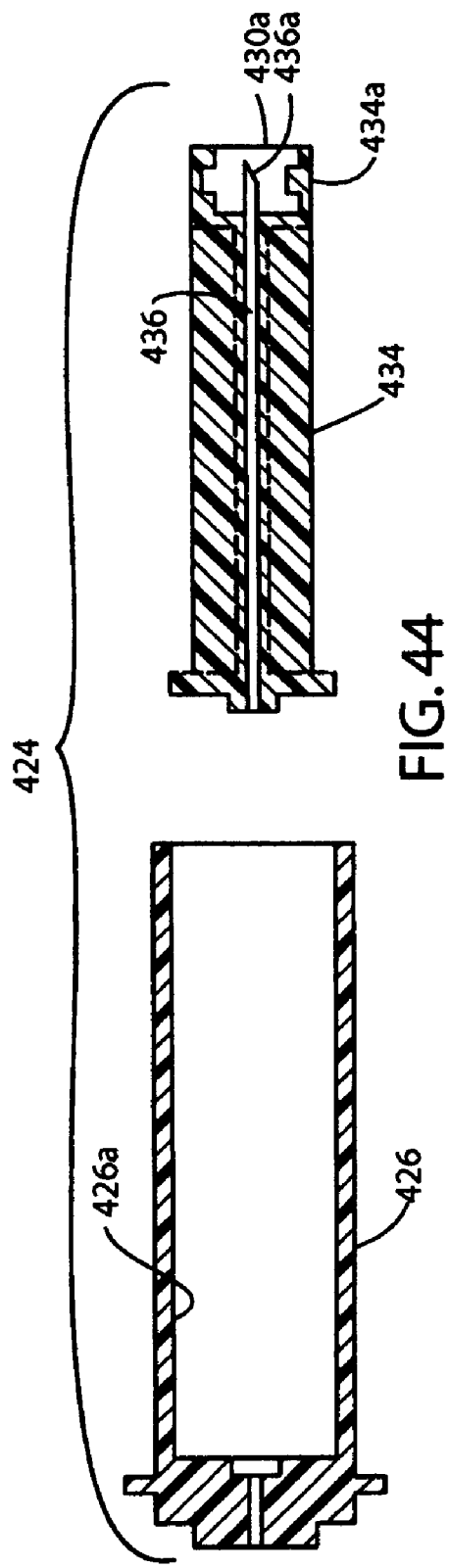
FIG. 44 is an exploded, cross-sectional view of the vial housing and elongated vial support of the alternate form of the additive sub-system of the apparatus shown in FIG. 43.

Referring particularly to FIGS. 41, 42 and 43, it can be seen that, as before, this alternate embodiment of the invention comprises two major cooperating components, namely a dispenser unit 282 and an additive sub-system 424. Dispenser unit 282 is substantially identical in construction and operation to that previously described and includes an outer housing 283, which comprises a control portion 285 and a generally cylindrically shaped reservoir housing 286 that is interconnected with the control portion 285 in the manner best seen in FIG. 41 of the drawings.

However, additive sub-system 424 is of a somewhat different construction to that previously described. More particularly, as illustrated in FIGS. 43 through 47, the additive sub-system here comprises a generally tubular-shaped inner housing 426 having a chamber 426a that is initially sealed at one end by a sterile cover 429 and at the opposite end by a sterile cover 429a. Also forming a part of additive sub-system 424 is a medicament-containing fill vial assembly 428 the character of which will presently be described.

Figure 47:
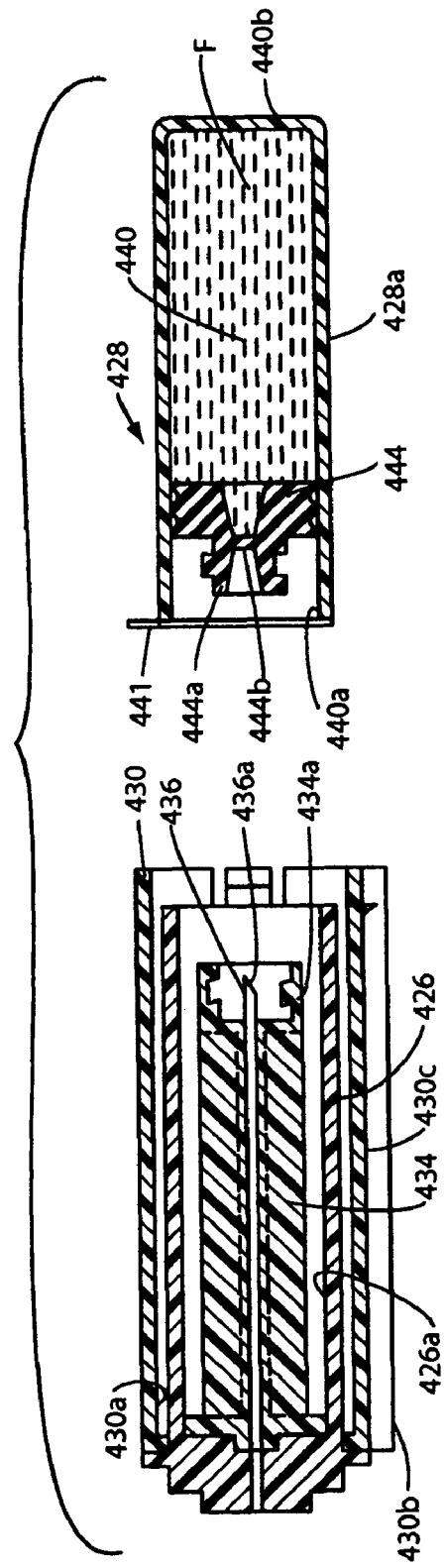
FIG. 47 is an exploded, cross-sectional view of the assemblage comprising the connector housing shown in FIG. 46 mated with the assemblage illustrated in FIG. 45 as the assemblage appears prior to being mated with the vial assembly of the alternate form of additive sub-system of the invention.
Figure 48:
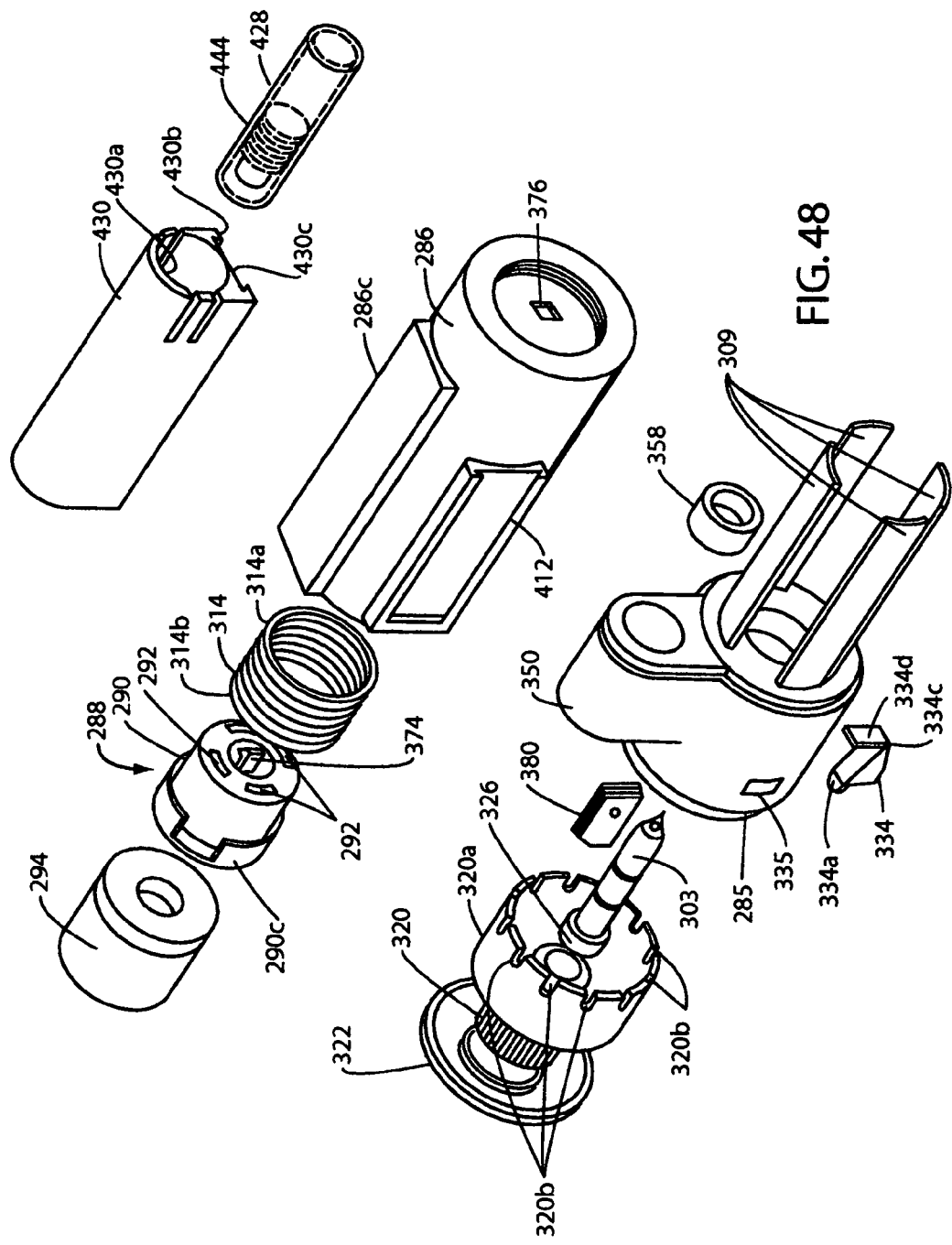
FIG. 48 is a generally perspective, exploded view of this latest alternate form of dispenser unit along with an alternate form of additive sub-system of the invention.

As illustrated in FIGS. 43 and 47, vial housing 426 is mounted within an internal chamber 430a of a connector housing 430. Formed on the lower surface 430b of connector housing 430 is a dovetail receiving groove 430c (FIG. 43), the purpose of which will be described hereinafter.

Figure 45:
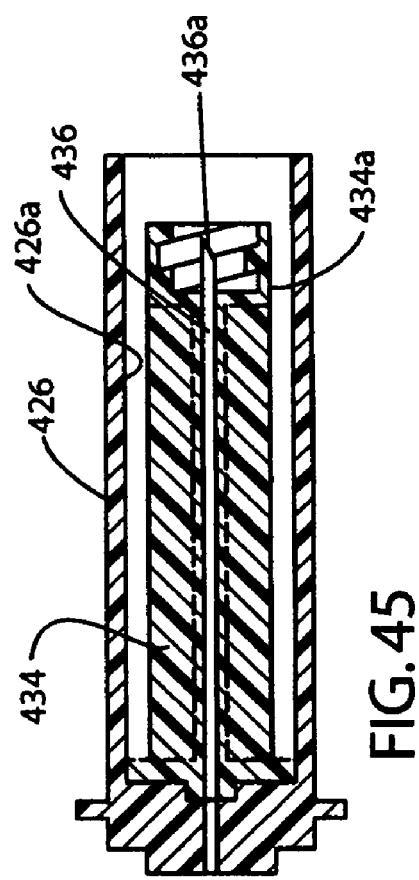
FIG. 45 is a cross-sectional view of the vial housing and elongated vial support shown in FIG. 44 after they have been interconnected together.
Figure 46:
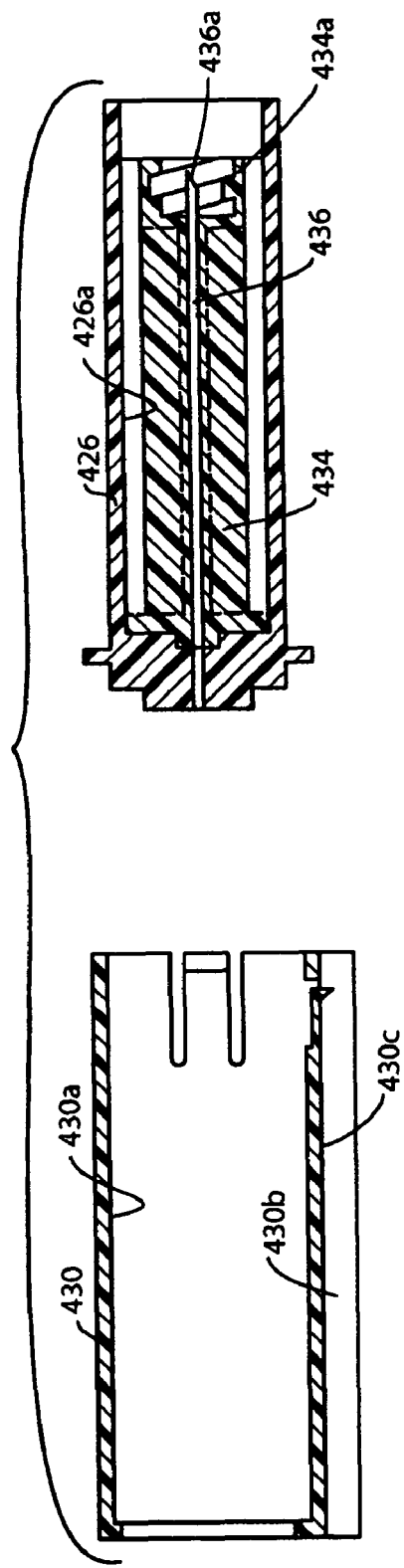
FIG. 46 is an exploded, cross-sectional view of the connector housing of the alternate form of the additive sub-system of the apparatus of the invention in a position to be mated with the assemblage illustrated in FIG. 45 of the drawings.
Figure 49:
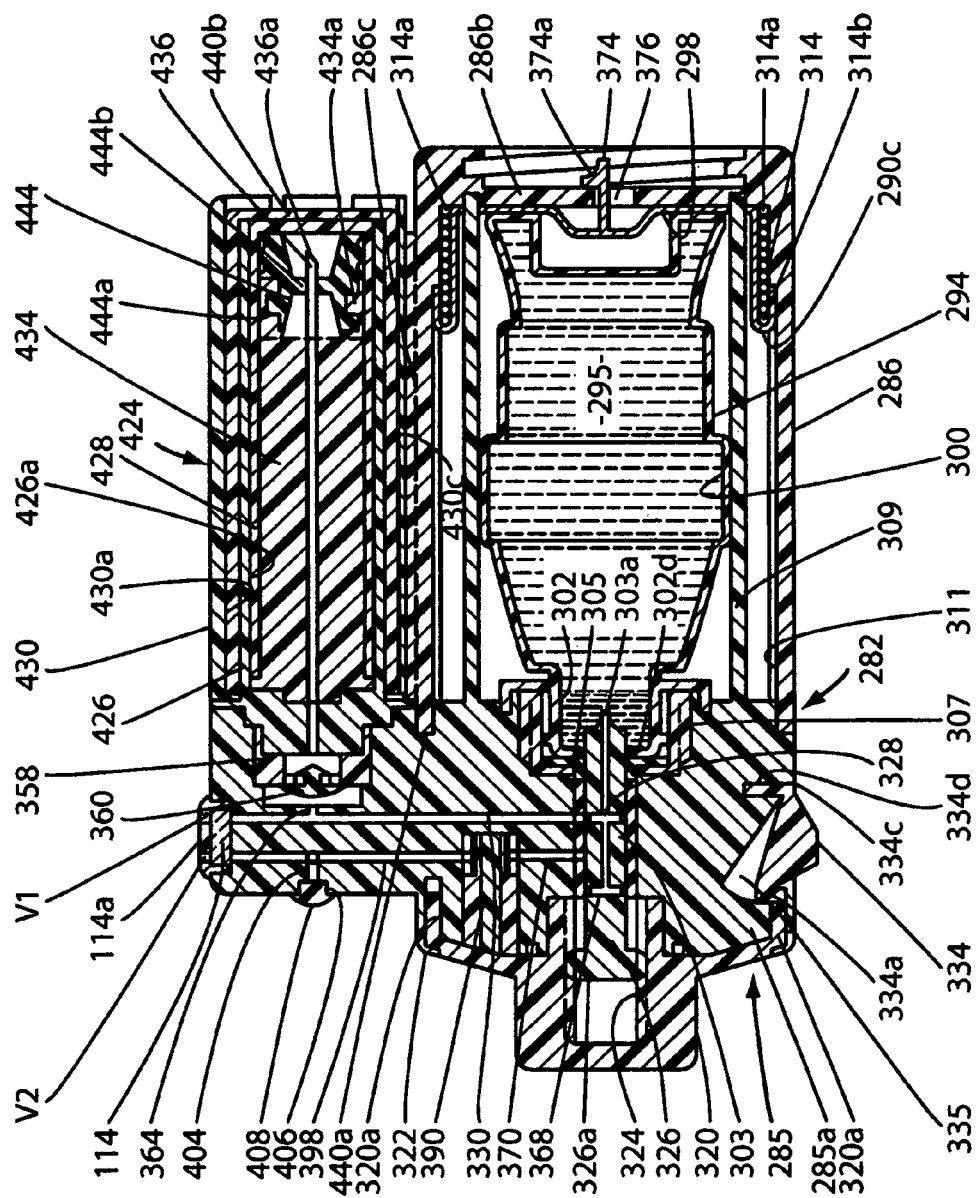
FIG. 49 is a longitudinal, cross-sectional view of the alternate form of fluid dispensing device illustrated in FIG. 48 as it appears after the additive sub-system has been mated with the dispenser unit and after the operating means of the invention has been operated in a manner to place the device and condition for accomplishment of the adding step.
Figure 50:
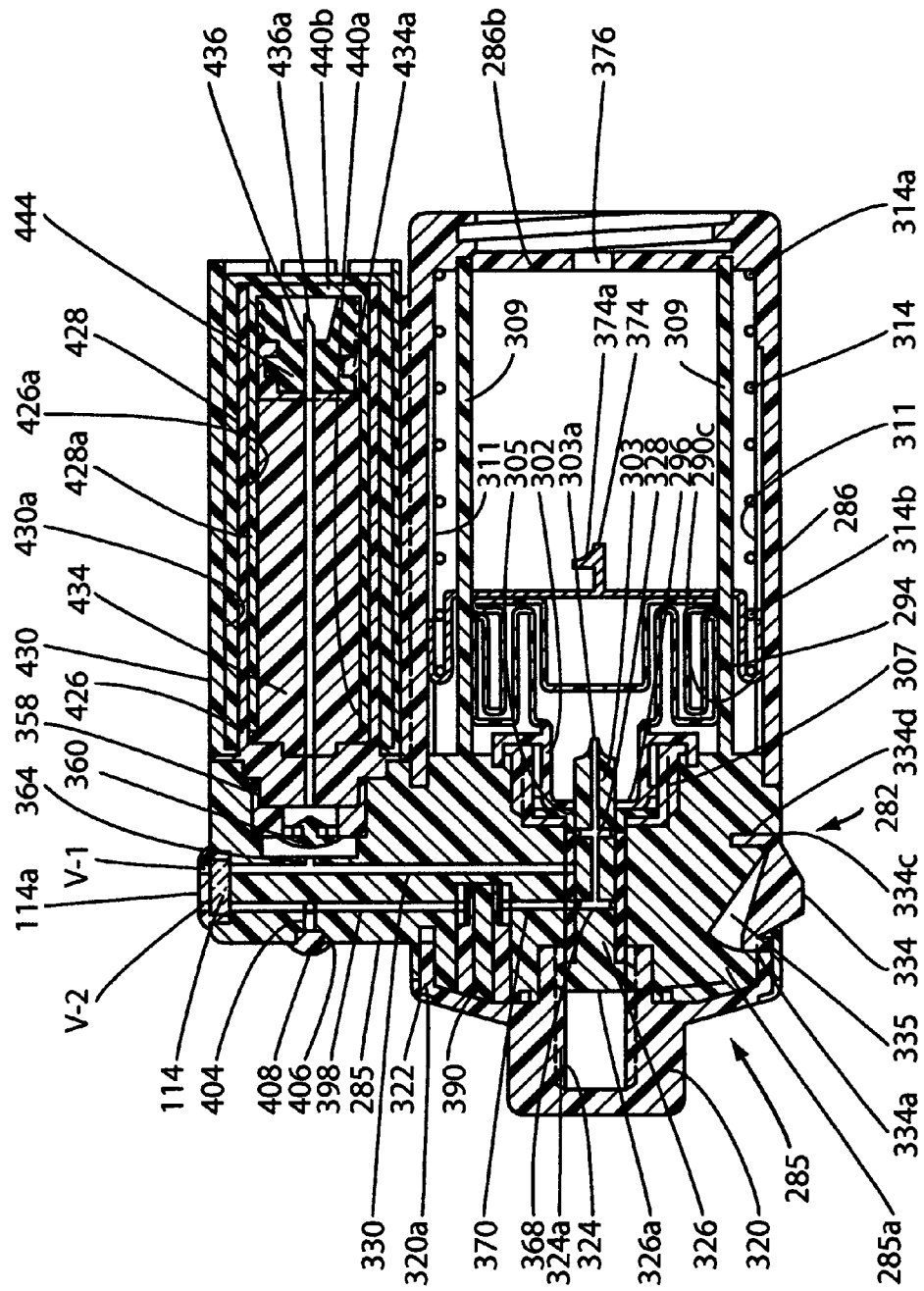
FIG. 50 is a longitudinal, cross-sectional view similar to FIG. 49, but showing the configuration of the device following the fluid delivery step.

Mounted within chamber 426a of vial housing 426 is an elongated support 434 that includes a threaded end portion 434a (FIG. 45). Support 434 carries a longitudinally extending, elongated hollow needle 436 having a flow passageway 436a that, after mating of the additive sub-system with the dispenser unit 282, communicates with check valve housing 358 of the dispenser unit (FIGS. 42 and 49).

Referring particularly to FIGS. 43 and 47, the medicament-containing vial assembly 428 here includes a body portion 428a having a fluid chamber 440 for containing the injectable fluid medicament "F". Chamber 440 is provided with a first open end 440a that is initially closed by a sterile cover 441 and second closed end 440b. Slidably carried within chamber 440 is a closure means that is here provided in the form of an externally threaded elastomeric plunger 444. Plunger 444 is telescopically movable within chamber 440 from a first location where the plunger is disposed proximate first open end 440a to a second device add location where the plunger is disposed proximate second closed end 440b (FIG. 49).

In carrying out the reservoir-adding step, cover 429 is first removed from the connector member 430. This done, the additive sub-system 424 of the device is interconnected with the control portion 285 by mating the dovetail connector segment 286c of the dispenser unit with the groove 430c formed in connector housing 430 and then sliding the additive sub-system forwardly into the position shown in FIG. 49.

Following the mating of the additive sub-system 424 with dispenser vial assembly, the sterile covers 429a and 441 are removed. Next, the vial assembly 428 of the additive sub-system 424 is inserted into chamber 430a of the housing 430 and the threaded end 444a of plunger 444 is threadably interconnected with threaded end 434a of support 434. As the components are thusly interconnected, the sharp end of the elongated needle 436 will pierce the central wall 444b of the elastomeric plunger. A continuous pushing movement of the vial assembly into chamber 430a will then cause the support 434 to move the elastomeric plunger inwardly of the vial chamber in a direction toward the second, or closed end 440b of the vial chamber (see FIG. 49). As the plunger is moved inwardly of the vial, the fluid "F" contained within the vial chamber will be expelled therefrom into the hollow elongated needle 436.

As best seen in FIG. 49, the fluid will then flow past conventional elastomeric umbrella-type check valve 360, which is mounted within check valve housing 358. Next, the fluid will flow into stub passageway 364 and thence into passageway 330. Umbrella-type check valve 360 functions in a conventional manner to control fluid flow from the elongated hollow needle 436 toward fluid passageway 364. From passageway 364, the fluid will flow into inlet passageway 330 and then into reservoir 295 of the container via passageways 328 and 303a.

Following the completion of the adding process as described in the preceding paragraph wherein the fluid medicament "F" contained within the vial assembly 428 is added to the reservoir 295, the operating means of the invention is used in the same manner as previously described to control the flow of the fluid mixture from the collapsible reservoir toward the rate control means and then onward toward the administration set.

Referring to FIGS. 51 through 57, an alternate form of the fluid dispensing device of the present invention for dispensing medicaments to a patient is there shown. This alternate form of dispensing device is similar in most respects to that shown in FIGS. 41 through 50 and like numerals are used in FIGS. 51 through 57 to identify like components. The major difference between this latest embodiment of the invention and that shown in FIGS. 41 through 50 resides in the differently configured additive sub-system.

As before, this latest embodiment of the invention comprises two major cooperating components, namely a dispenser unit 282 and an additive sub-system 454. Dispenser unit 282 is substantially identical in construction and operation to that previously described, save that the carriage assembly is somewhat differently configured. As before, the dispenser unit includes an outer housing 283 which comprises a control portion 285 and a generally cylindrically shaped reservoir housing 286 that is interconnected with the control portion 285 in the manner best seen in FIG. 51 of the drawings.

Figure 52:
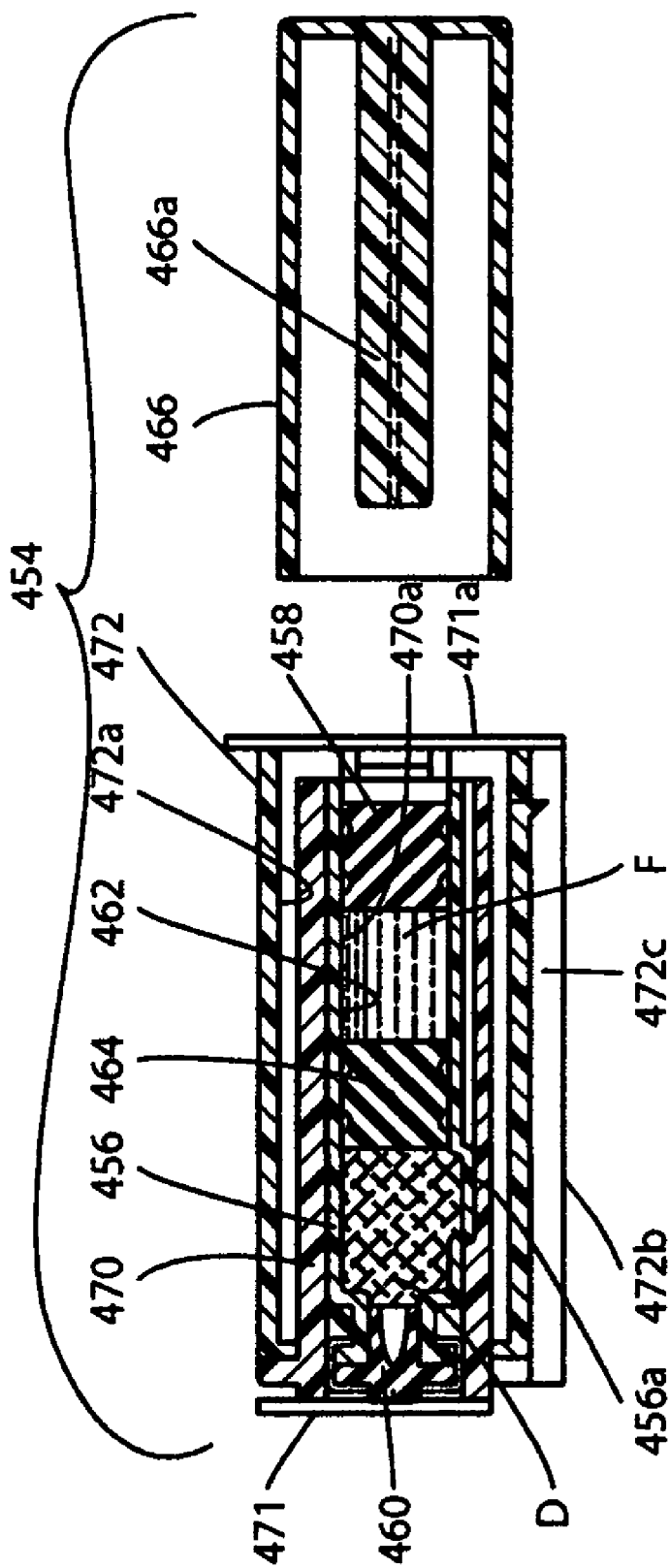
FIG. 52 is an exploded, longitudinal, cross-sectional view of still another form of the vial housing and elongated vial support of additive sub-system of the invention.
Figure 53:
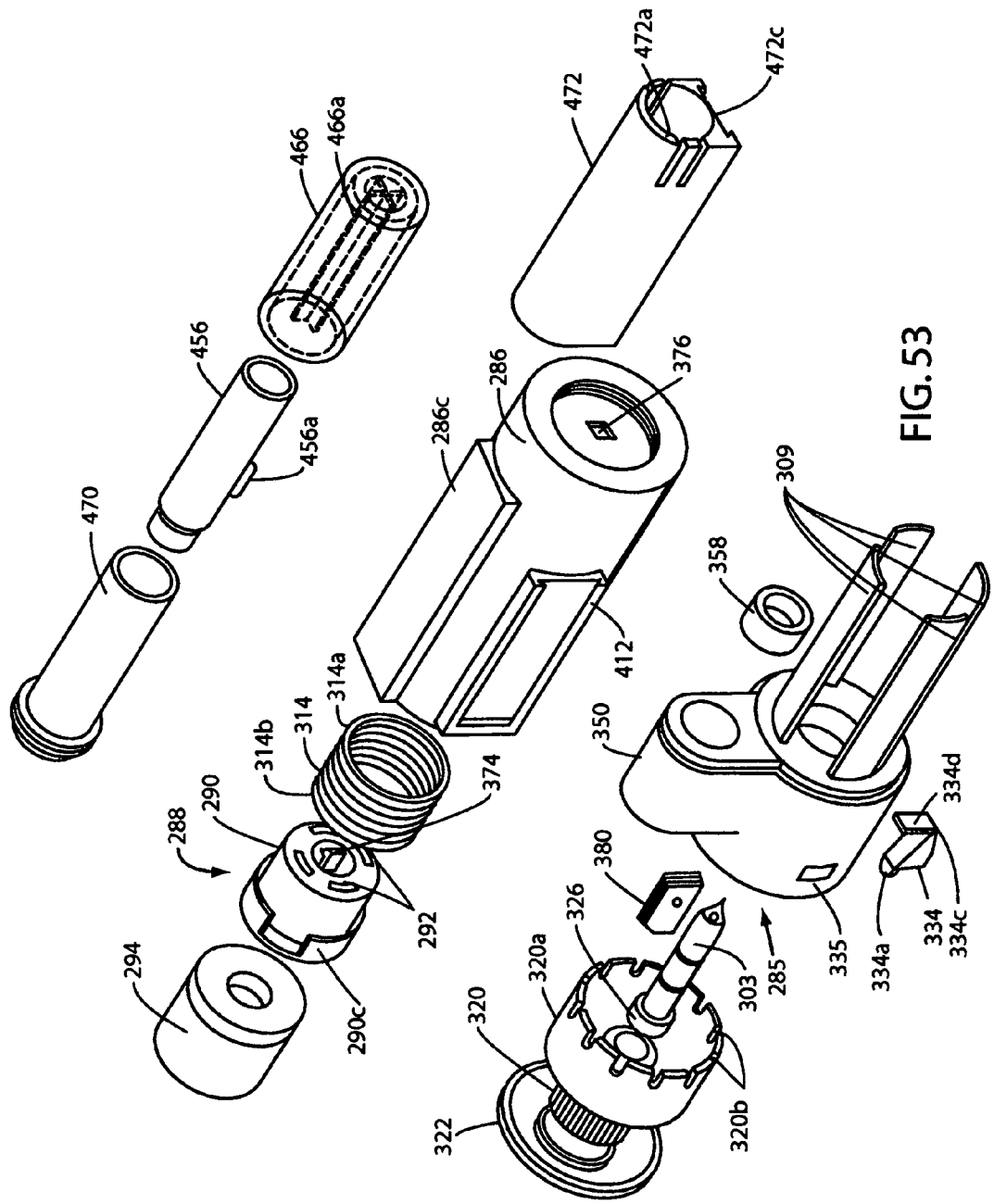
FIG. 53 is a generally perspective, exploded view of the alternate form of dispenser unit and alternate form of additive sub-system of the invention depicted in FIG. 51.

However, additive sub-system 454 is of a somewhat different construction to that previously described. More particularly, as illustrated in FIGS. 52 and 56, the additive sub-system here comprises a vial 456 of special design that uniquely contains a lyophilized drug "D". Vial 456 is sealed at one end by elastomeric plunger 458 and at the other end by a pierceable septum 460. Formed intermediate the ends of the vial is a raised outer wall portion 456a, which permits the fluid "F" that is contained within a chamber 462 to bypass a barrier stopper 464 as the barrier stopper is urged inwardly of the container by pressure exerted thereon by the fluid, which is being pushed by plunger 458 resulting from force exerted on pusher element member 466a of pusher 466 (see FIGS. 52 and 56).

Vial 456 is carried within a generally tubular-shaped inner housing 470 having a chamber 470a that is initially sealed at one end by a sterile cover 471 and at the opposite end by a sterile cover 471a. As illustrated in FIGS. 52 and 55, inner housing 470 is mounted within an internal chamber 472a of a connector housing 472. Formed on the lower surface 472b of connector housing 472 is a dovetail receiving groove 472c.

Figure 51:
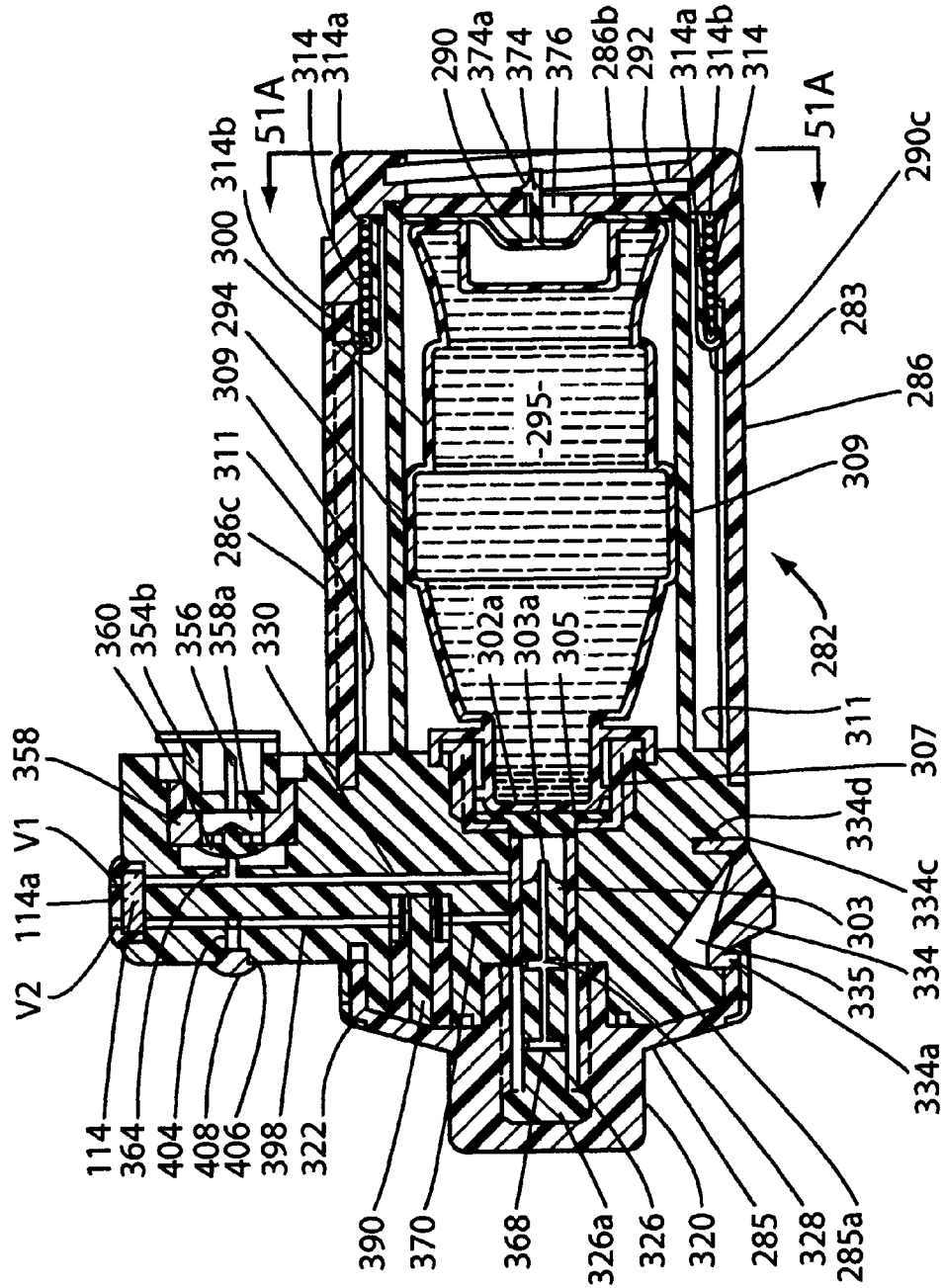
FIG. 51 is a longitudinal, cross-sectional view of still another form of dispenser unit of the invention.
Figure 51A:
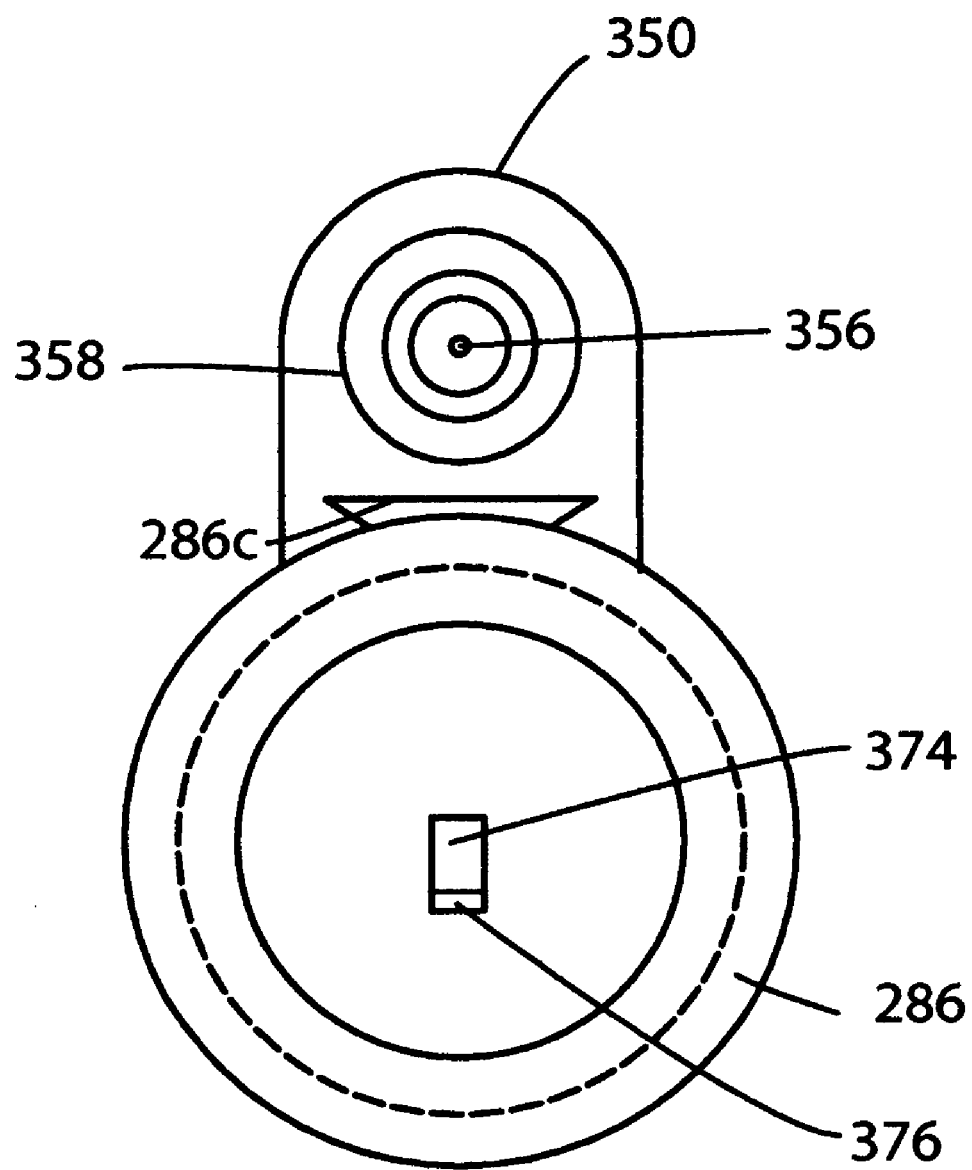
FIG. 51A is a view taken along lines 51A-51A of FIG. 50.
Figure 54:
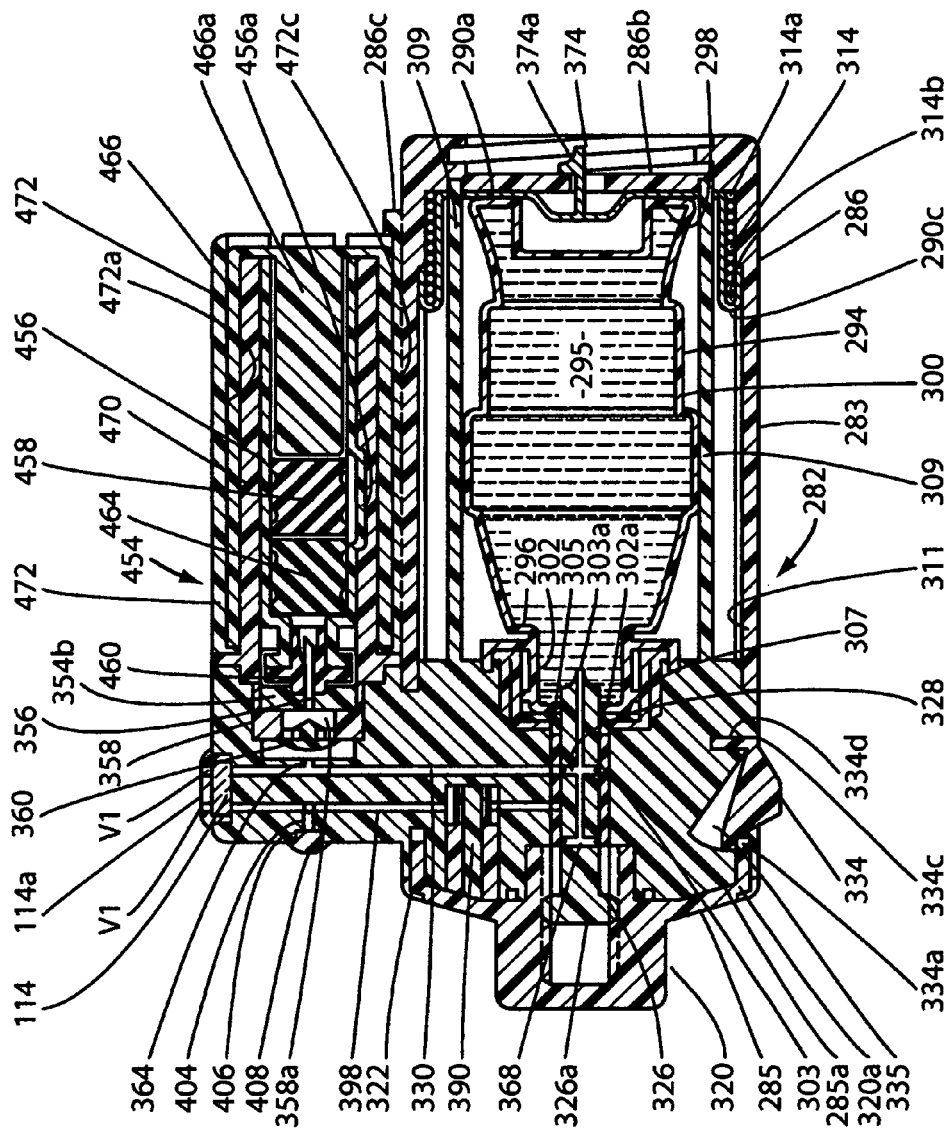
FIG. 54 is a longitudinal, cross-sectional view of the alternate form of fluid dispensing device illustrated in FIG. 53 as it appears after the additive sub-system has been mated with the dispenser unit and after the operating means of the invention has been operated in a manner to place the device and condition for accomplishment of the adding step.
Figure 57:
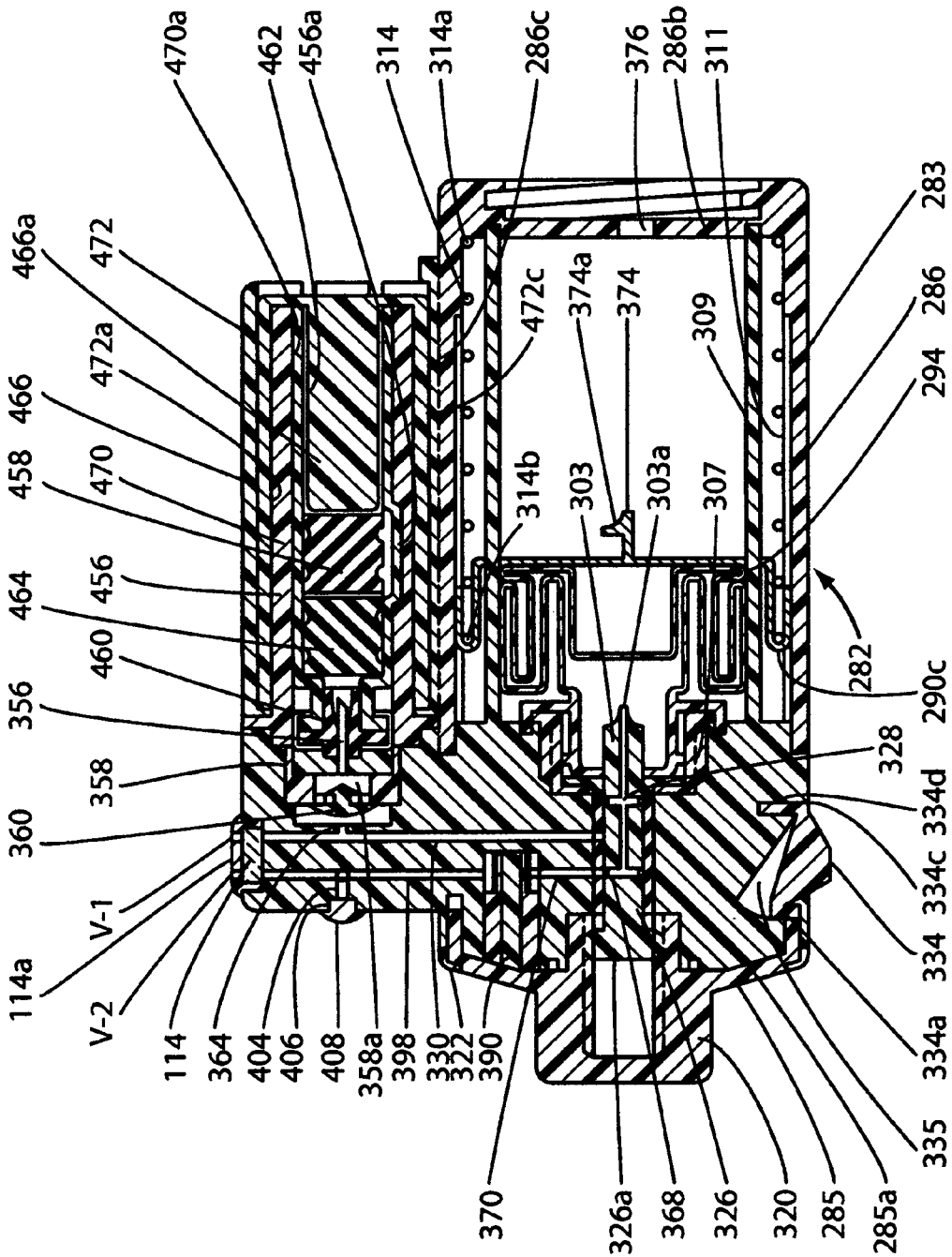
FIG. 57 is a longitudinal cross-sectional view similar to FIG. 54, but showing the configuration of the device following the fluid delivery step.

As indicated in FIGS. 51A and 54, following removal of sterile cover 471, the dovetail connector segment 286c of the dispenser unit can be mated with and urged inwardly of the dovetail receiving groove 472c formed in connector housing 472. As the additive sub-system mates with the dispenser unit, skirt 354b of the dispenser unit will be telescopically received within the inboard end of vial receiving housing 470 and needle 356 of the dispenser unit will pierce the pierceable septum 460 of the vial assembly 456 in the manner shown in FIG. 54.

After mating of the additive sub-system with the dispenser unit, inward movement of the pusher 466 into chamber 472a of connector 472 will cause inward movement of plunger 458. This inward movement of plunger 458 will cause inward movement of plunger or barrier member 464 allowing the fluid "F" to flow past the barrier member via the internal passageway defined by wall portion 456a so as to reconstitute the lyophilized drug "D". A continued pressure exerted on plunger 458 by the pusher member will cause the reconstituted drug formed by the mixture of the drug "D" and the fluid "F" to flow through hollow needle 356, into a chamber 358a formed in check valve housing 358 (FIG. 54), past check valve 360, into a stub passageway 364, then into passageway 330 and finally into the device reservoir 295.

Following the completion of the adding process as described in the preceding paragraph wherein the reconstituted drug formed by the mixture of the drug "D" and the fluid "F" is added to the reservoir 295, the operating means of the invention is used in the same manner as previously described to control the flow of the fluid mixture from the collapsible reservoir toward the rate control means and then onward toward the administration set.

As was described in connection with the embodiment of FIGS. 5 through 40, to accomplish the adding and delivery steps, the dovetail connector segment 286c of the dispenser unit can be mated with and urged inwardly of the dovetail receiving groove 472c formed in connector housing.

Following the completion of the adding process in the manner described in connection with the embodiment of FIGS. 5 through 40, the operating means of the invention is used to control the flow of the fluid mixture from the collapsible reservoir toward the rate control means and then onward toward the administration set of the invention.

Figure 58:
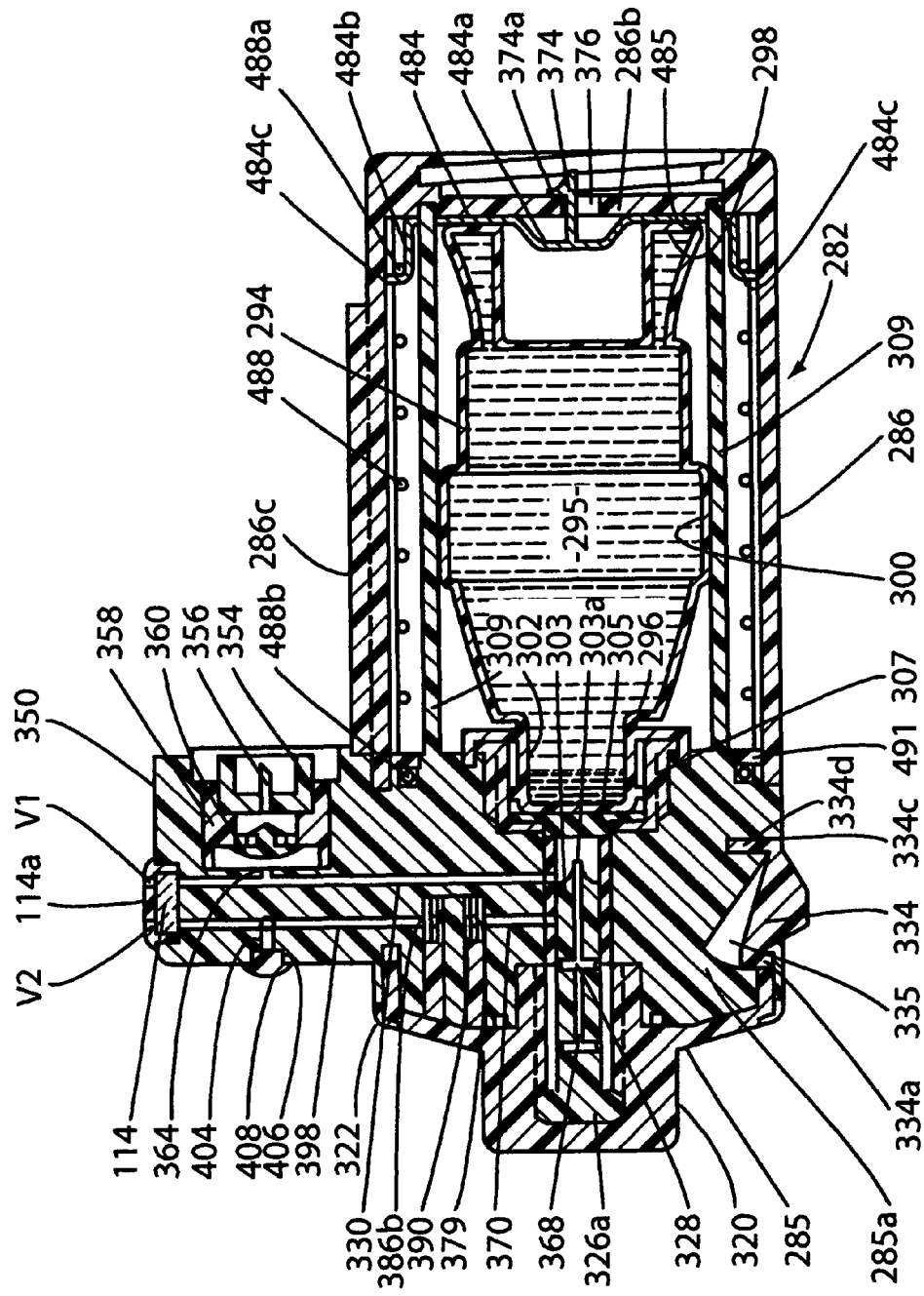
FIG. 58 is a longitudinal, cross-sectional view of the dispenser unit of yet another form of the apparatus of the invention.

Referring next to FIGS. 58, 59 and 60, still another form of the dispensing device of the present invention for dispensing medicaments to a patient is there shown. This alternate form of dispensing apparatus is similar in most respects to that shown in FIGS. 5 and 40 and like numerals are used in FIGS. 58, 59 and 60 to identify like components. The major difference between this latest embodiment of the invention and that shown in FIGS. 5 through 40 resides in the manner in which the differently configured stored energy means of the invention is configured. The dispensing unit is substantially identical in construction and operation to that of the embodiment of the invention shown in FIGS. 5 through 40 save that the carriage assembly is somewhat differently configured to accommodate the differently configured stored energy source. The additive sub-system 284 of this latest form of the invention is also substantially identical in construction and operation to that previously described and comprises a medicament-containing, cartridge-type fill vial assembly 342.

As was described in connection with the embodiment of FIGS. 5 through 40, to accomplish the adding and delivery steps, the dovetail connector segment 286c of the dispenser unit can be mated with and urged inwardly of the dovetail receiving groove 344c formed in connector housing.

Following the completion of the adding process in the manner described in connection with the embodiment of FIGS. 5 through 40, the operating means of the invention is used to control the flow of the fluid mixture from the collapsible reservoir toward the rate control means and then onward toward the administration set of the invention.

As shown in FIG. 58, the reservoir-defining container 294 is substantially identical to that described in connection with the embodiment of FIGS. 5 through 40 and is carried by a carriage 484 which is of a slightly different construction from that previously described. More particularly, as shown in FIGS. 59, 60 and 61, carriage 484 has a carriage base 484a and a foreshortened, generally cylindrically shaped sidewall 484b that terminates in a plurality of circumferentially spaced, radially outwardly extending flanges 484c. As before, base 484a includes a plurality of circumferentially spaced guide apertures 485 that slidably receive the guide members 309 which are connected to and extend outwardly from body 285a of control portion 285 and form a part of the guide means for guiding travel of carriage assembly (FIGS. 11 and 19). Carriage 484 is releasably locked in its first position by a locking means that is substantially identical in construction and operation to that previously described.

Figure 62:
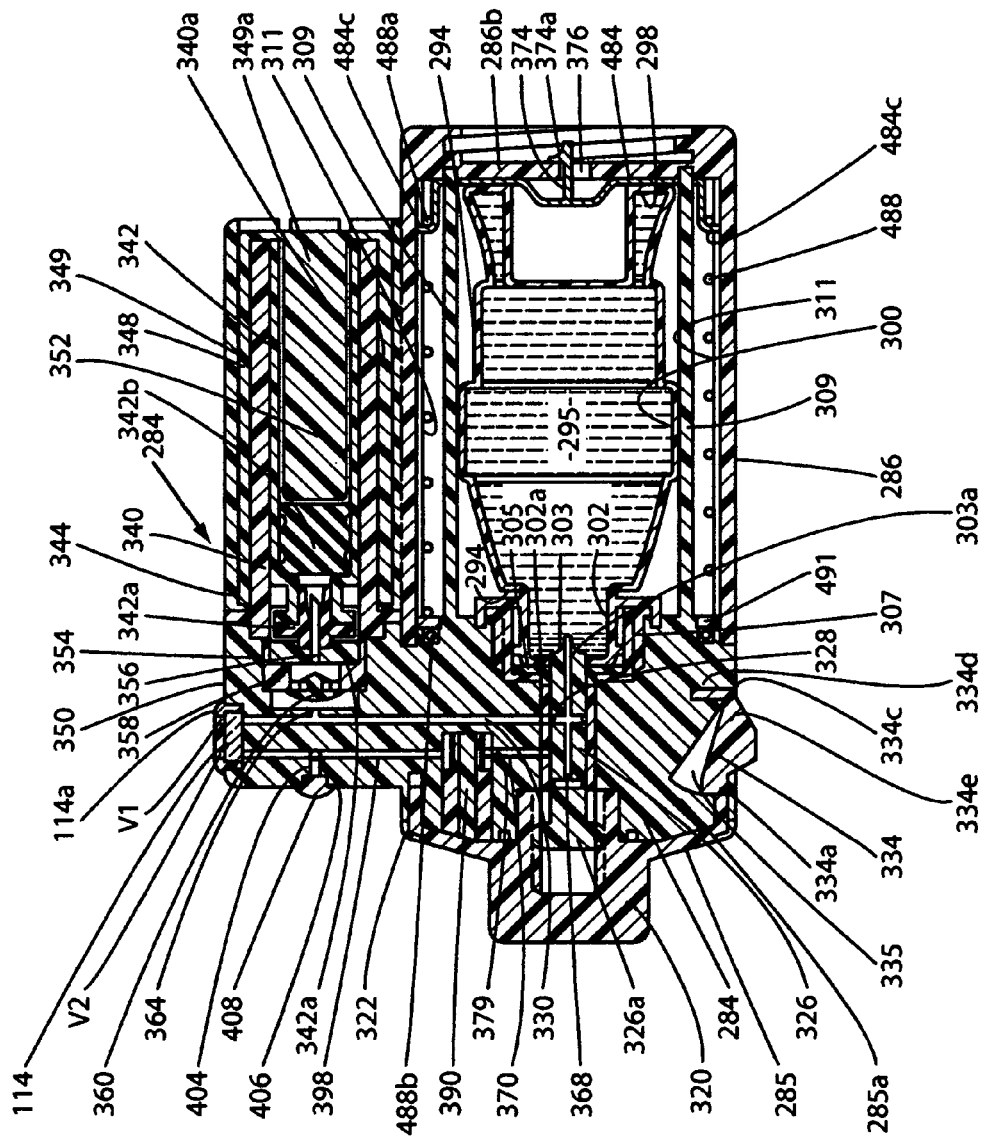
FIG. 62 is a longitudinal, cross-sectional view of the alternate form of dispenser unit illustrated in FIG. 58 of the drawings as it appears when mated with the additive sub-system of the alternate form of the apparatus of the invention and after the operating means has been manipulated to place the device and condition for accomplishment of the adding step.

Following the completion of the adding process as described in connection with the embodiment of FIGS. 5 through 40, wherein the fluid medicament "F" contained within vial 342 is added to the reservoir 295, the operating means is used to control the flow of the fluid mixture from the collapsible reservoir toward the rate control means and then onward toward the administration set (See FIG. 62). More particularly, to accomplish this fluid dispensing step, the indexing button 334 is once again pushed inwardly of cavity 335 to move the locking tab 334a out of engagement with the notch within which it resides and the control knob is rotated from the "ADD" position (FIG. 20) to the "DISP" position. Release of the indexing button will then cause the outwardly biased locking tab 334a to move into engagement with an appropriate locking notch so as to lock the control knob in the "ADD" position.

Further rotation of control knob 320, will also cause penetrating member 303 to move further inwardly to the position illustrated in FIG. 34, wherein a stub passageway 368 formed in penetrating member 303 aligns with a fluid flow passageway 370 formed in control portion 285a. With the penetrating member 303 in this advanced position fluid communication between the fluid reservoir 295 and the rate control means of the device is established via fluid flow passageway 303a of penetrating member 303.

To cause the fluid to flow from reservoir 295 toward the flow rate control means, the locking means of the invention must be manipulated in a manner to release the carriage assembly from base wall 286b of reservoir housing 286. In this regard, as best seen in FIGS. 7, 9, 10 and 16, the carriage locking means includes a locking member 374 having a yieldably deformable locking tab 374a which extends through a strategically shaped opening 376 provided in the base wall 286b of reservoir housing (see FIGS. 56 and 62). With this construction, an inward force exerted on the locking member will deform the locking tab 374 in a manner to permit it to pass through the opening 376 and in so doing release the carriage from the base wall 286b. Release of the carriage will permit the differently configured stored energy means to controllably move the carriage 484 from its first position shown in FIG. 58 to its second position shown in FIG. 63. This stored energy means, which is operably associated with carriage 484, is here provided in the form of a coiled spring 488, which is initially extended and in tension (see FIG. 58). More particularly, as illustrated in FIG. 58, one end 488a of the coil spring resides beneath flanges 484c while the other end 488b thereof is interconnected with portion 285a of the dispensing unit by means of a capture plate 491 (FIG. 58). With this construction, following operation of the reservoir-accessing means, and when the locking means of the invention is manipulated in the manner previously described to unlock the carriage assembly from base portion 286b of the main housing, spring 488, which is in tension, will move from its extended position as shown in FIG. 58 to its retracted position as shown in FIG. 63 and, in so doing, will controllably move the carriage from its starting position to its fully deployed or extended position shown in FIG. 63.

Figure 63:
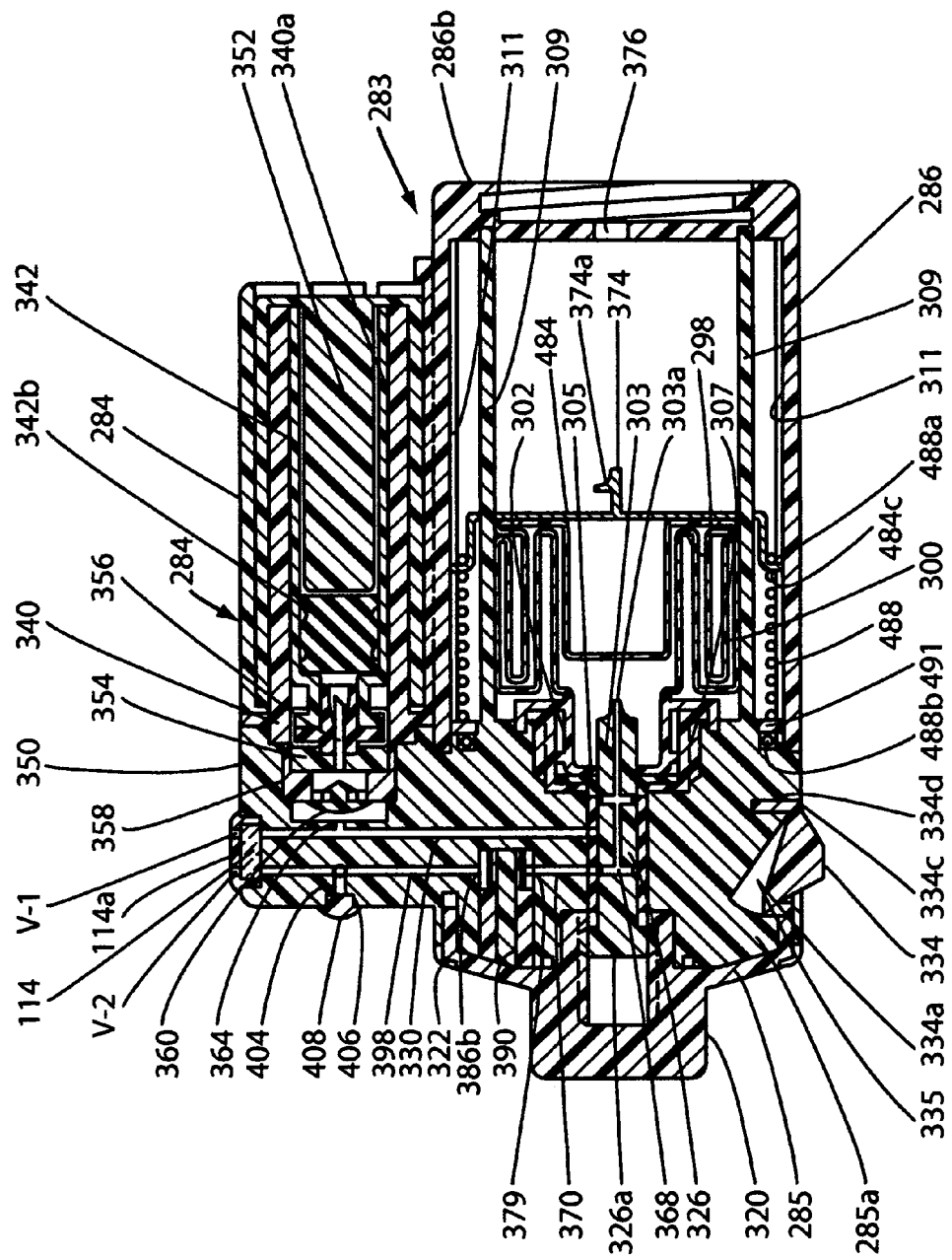
FIG. 63 is a longitudinal, cross-sectional view similar to FIG. 62, but showing the device as it appears after accomplishment of the fluid delivery step.

As the carriage assembly moves toward its deployed position, the collapsible sidewall 300 of the collapsible container 294 will move into the collapsed configuration shown in FIG. 63. As the collapsible container collapses, the medicinal fluid contained within the container will be controllably expelled therefrom.

To further control the flow of medicinal fluid from reservoir toward the administration set 318 of the invention and then on to the patient, flow control means are provided, which fluid flow control means are identical in construction and operation to that described in connection with the embodiment of FIGS. 5 through 40. More particularly, with the penetrating member 303 in its advanced position as shown in FIG. 63 fluid communication between the fluid reservoir 295 and the rate control means of the device is established via fluid flow passageway 303a of penetrating member 303. From the fluid passageway of penetrating member 303, fluid will flow into a stub passageway 368 into passageway 370 and then into the inlet 379 of the fluid rate control means of the invention, which is identical to that previously described. From the rate control means, the fluid will flow into passageway 398 and then onwardly to the administration set at a controlled rate.

Figure 71:
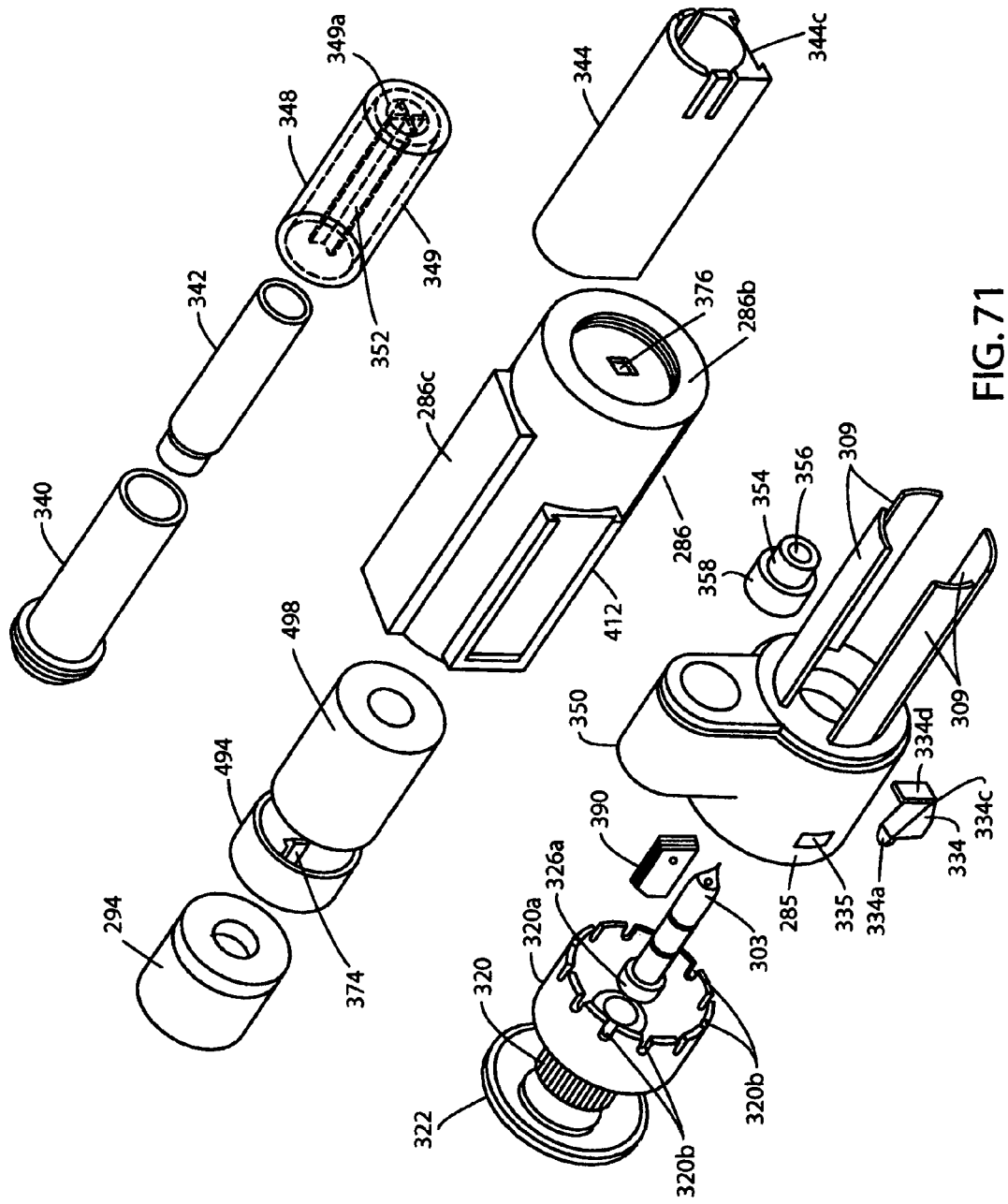
FIG. 71 is a generally perspective, exploded view of the alternate form of dispenser unit and alternate form of additive sub-system of apparatus of this latest form of the invention.
Figure 72:
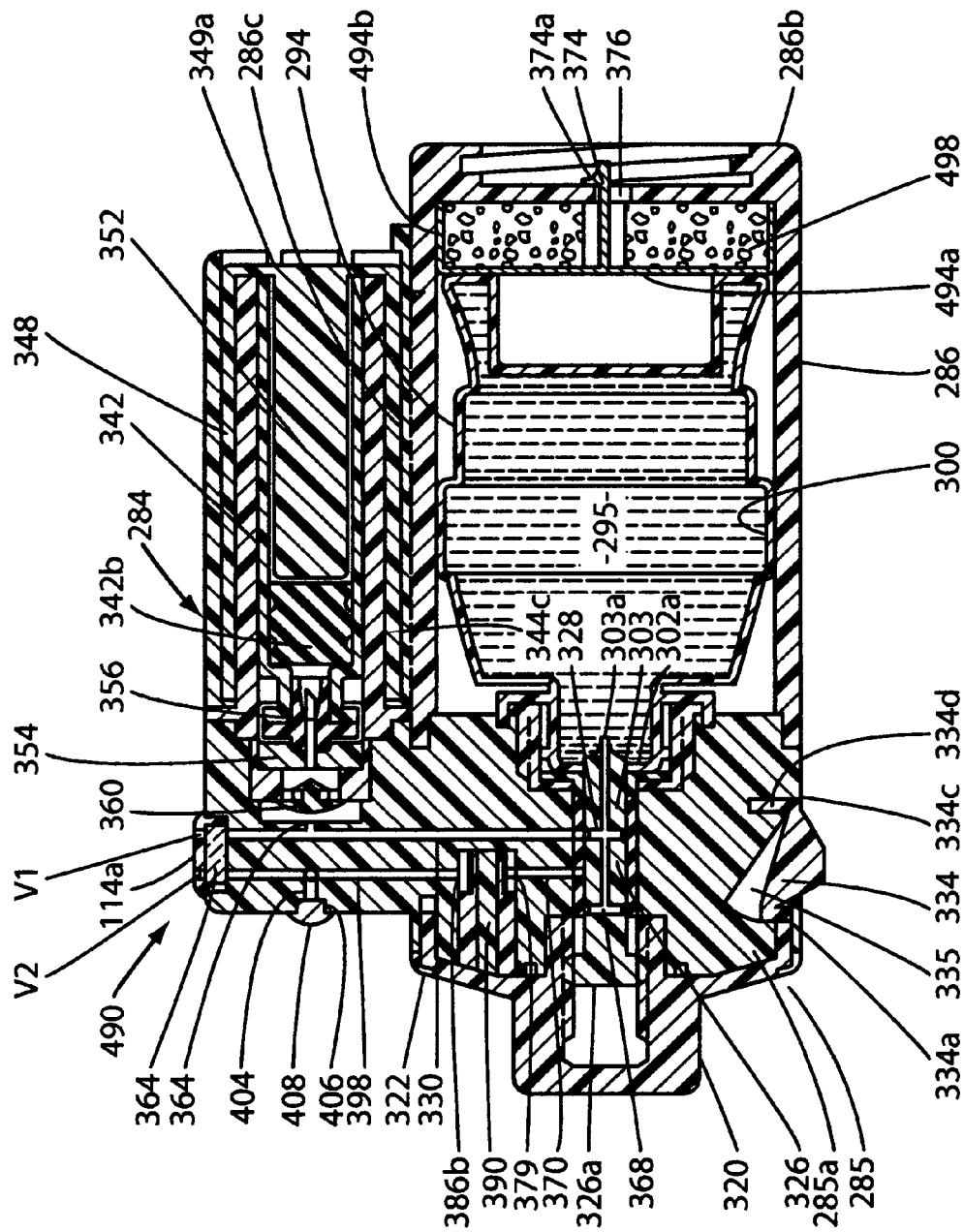
FIG. 72 is a longitudinal, cross-sectional view of the alternate form of dispenser unit illustrated in FIG. 64 of the drawings as it appears when mated with the additive sub-system of the alternate form of the apparatus of the invention and after the operating means has been manipulated to place the device and condition for accomplishment of the adding step.

Referring now to FIGS. 64 through 73, still another form of the dispensing device of the present invention for dispensing medicaments to a patient is there shown and generally designated by the numeral 490 (FIG. 72). This alternate form of dispensing apparatus is also similar in most respects to that shown in FIGS. 5 and 40 and like numerals are used in FIGS. 64 through 73 to identify like components. The major difference between this latest embodiment of the invention and that shown in FIGS. 5 through 40 resides in the totally different stored energy means of the invention. The dispensing unit is substantially identical in construction and operation to that of the embodiment of the invention shown in FIGS. 5 through 40 save that the carriage assembly is somewhat differently configured to accommodate the differently configured stored energy source. The additive sub-system 284 of this latest form of the invention is also substantially identical in construction and operation to that previously described and comprises a medicament-containing, cartridge-type fill vial assembly 342.

As was described in connection with the embodiment of FIGS. 5 through 40, to accomplish the adding and delivery steps, the dovetail connector segment 286c of the dispenser unit can be mated with and urged inwardly of the dovetail receiving groove 344c formed in connector housing (See FIG. 71).

Following the completion of the adding process in the manner described in connection with the embodiment of FIGS. 5 through 40, the operating means of the invention is used to control the flow of the fluid mixture from the collapsible reservoir toward the rate control means and then onward toward the administration set of the invention.

Figure 64:
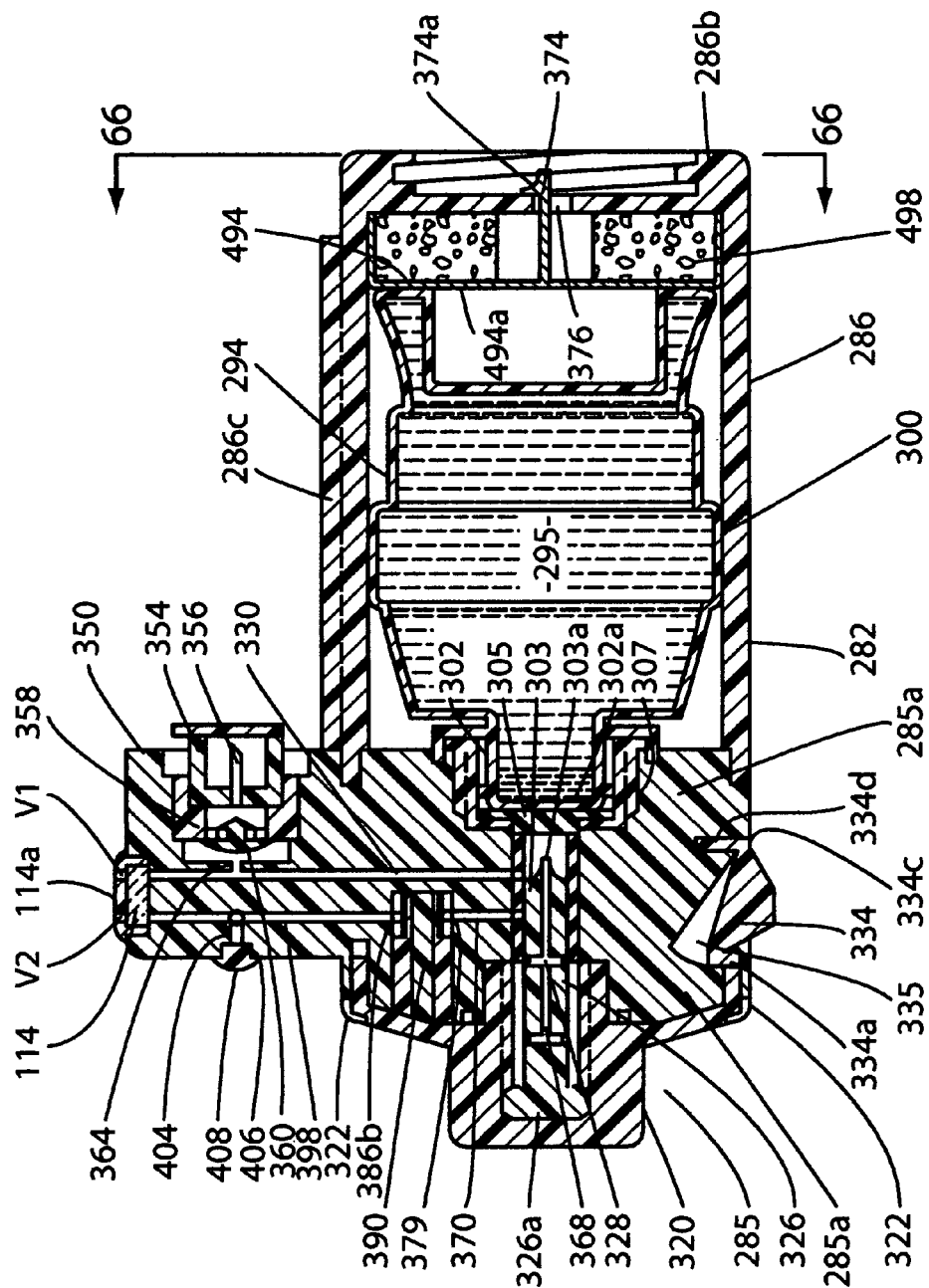
FIG. 64 is a longitudinal, cross-sectional view of still another form of the dispensing unit of the apparatus of the invention.
Figure 65:
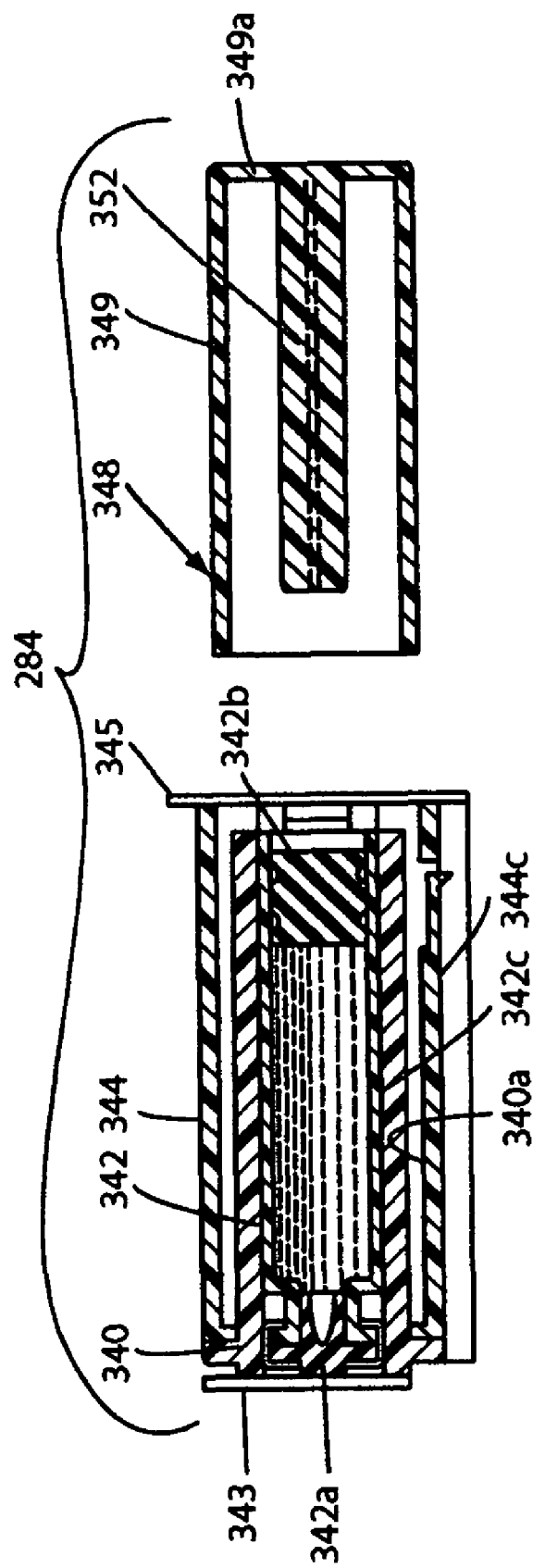
FIG. 65 is a longitudinal, cross-sectional, exploded view of the additive sub-system of this latest form of the apparatus of the invention that is adapted to mate with the dispenser unit illustrated in FIG. 64 of the drawings.
Figure 66:
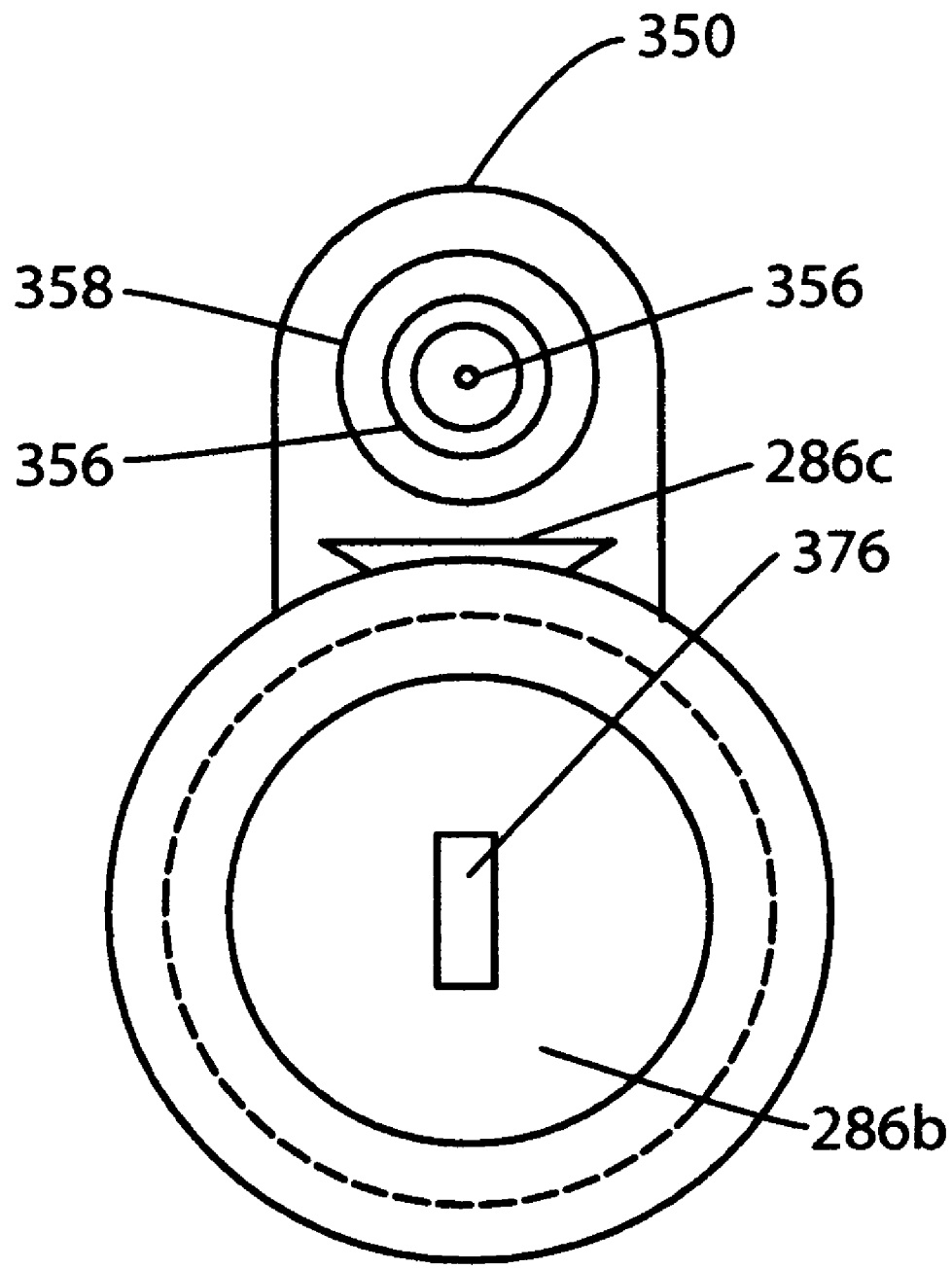
FIG. 66 is a cross-sectional view taken along lines 66-66 of FIG. 64.
Figure 67:
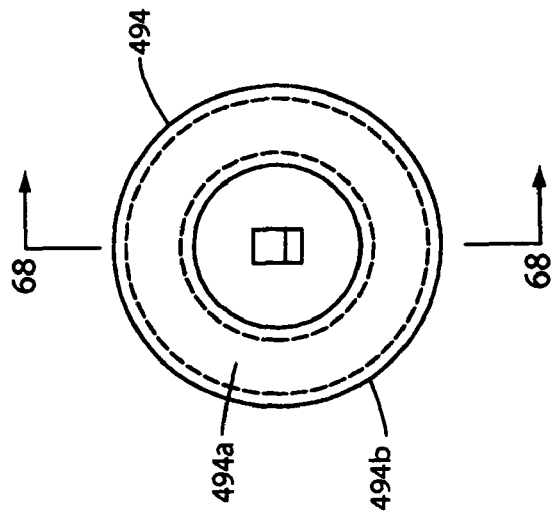
FIG. 67 is a bottom plan view of the carriage assembly of the dispenser unit illustrated in FIG. 64 of the drawings.
Figure 68:
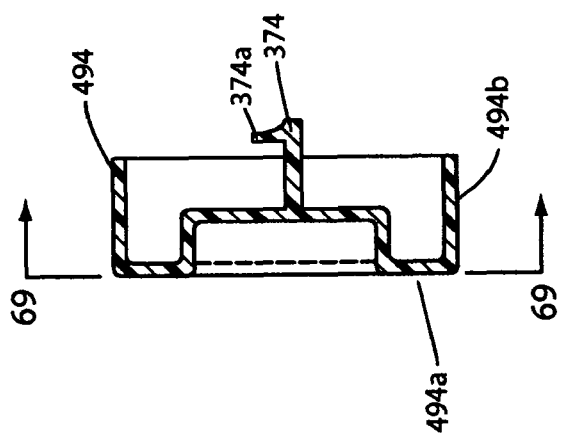
FIG. 68 is a cross-sectional view taken along lines 68-68 of FIG. 67.
Figure 69:
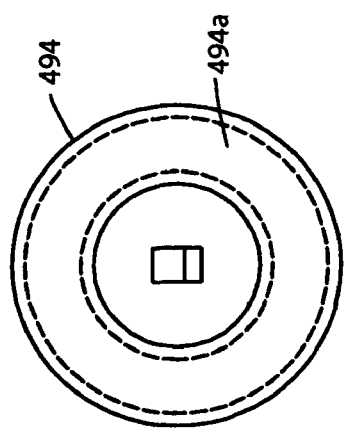
FIG. 69 is a view taken along lines 69-69 of FIG. 68.
Figure 70:
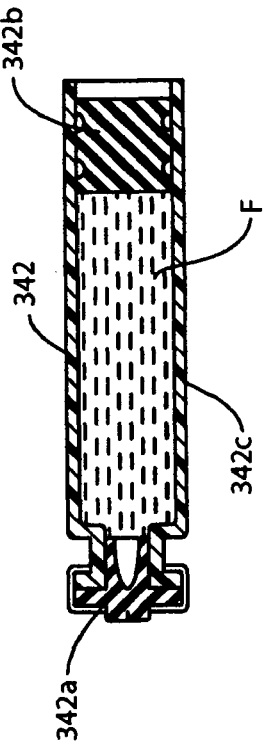
FIG. 70 is a longitudinal, cross-sectional view of the medicament vial component of the additive sub-system illustrated in FIG. 65.

As shown in FIG. 64, the reservoir-defining container 294 is substantially identical to that described in connection with the embodiment of FIGS. 5 through 40 and is carried by a carriage 494 which is of a slightly different construction from that previously described. More particularly, as shown in FIGS. 67, 68 and 69, carriage 494 has a carriage base 494a and a, generally cylindrically shaped sidewall 494b. As before, carriage 494 is releasably locked in its first position by a locking means that is substantially identical in construction and operation to that previously described.

Following the completion of the adding process as described in connection with the embodiment of FIGS. 5 through 40, wherein the fluid medicament "F" contained within vial 342 is added to the reservoir 295, the operating means is used to control the flow of the fluid mixture from the collapsible reservoir toward the rate control means and then onward toward the administration set. More particularly, to accomplish this fluid dispensing step, the indexing button 334 is once again pushed inwardly of cavity 335 to move the locking tab 334a out of engagement with the notch within which it resides and the control knob is rotated from the "ADD" position (FIG. 20) to the "DISP" position. Release of the indexing button will then cause the outwardly biased locking tab 334a to move into engagement with an appropriate locking notch so as to lock the control knob in the "ADD" position.

Figure 73:
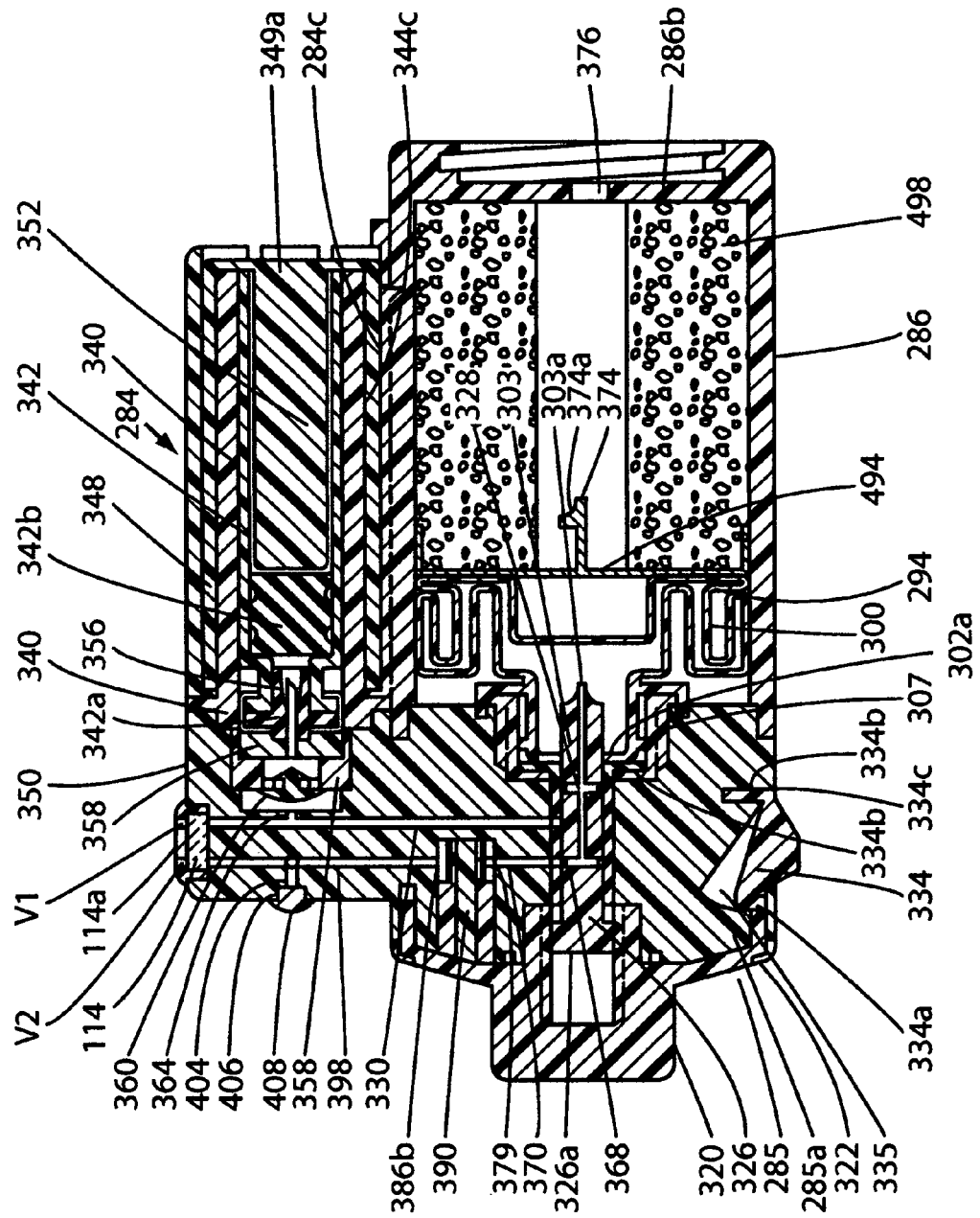
FIG. 73 is a longitudinal, cross-sectional view similar to FIG. 72, but showing the device as it appears after accomplishment of the fluid delivery step.

Further rotation of control knob 320, will also cause penetrating member 303 to move further inwardly from to the position illustrated in FIG. 72, wherein stub passageway 328 formed in penetrating member 303 aligns with a fluid flow passageway 330 formed in control portion 285a to the position illustrated in FIG. 73, wherein stub passageway 368 formed in penetrating member 303 aligns with a fluid flow passageway 370 formed in control portion 285a. With the penetrating member 303 in this advanced position fluid communication between the fluid reservoir 295 and the rate control means of the device is established via fluid flow passageway 303a of penetrating member 303.

Figure 16:
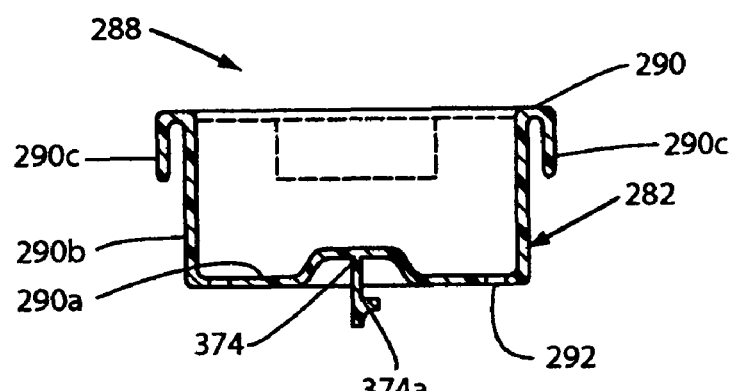
FIG. 16 is a cross-sectional view taken along lines 16-16 of FIG. 15.
Figure 17:
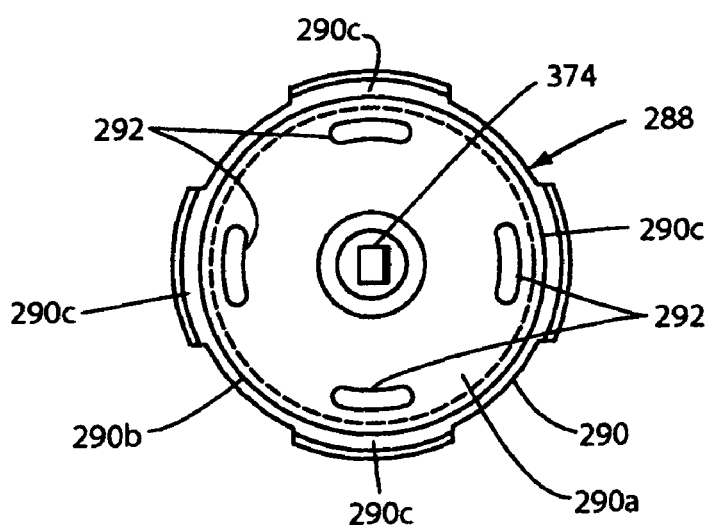
FIG. 17 is a bottom view of the reservoir carriage of the fluid dispensing portion of the device.
Figure 18:
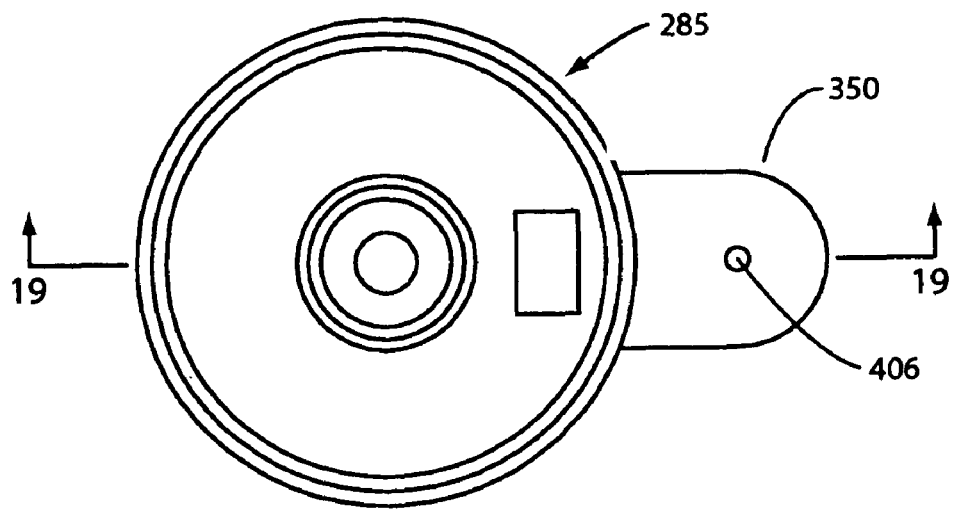
FIG. 18 is a top view of the control housing of the fluid dispenser portion of the device.

To cause the fluid to flow from reservoir 295 toward the flow rate control means, the locking means of the invention must be manipulated in a manner to release the carriage assembly from base wall 286b of reservoir housing 286. In this regard, as best seen in FIGS. 11 and 16, the carriage locking means includes a locking member 374 having a yieldably deformable locking tab 374a which extends through a strategically shaped opening 376 provided in the base wall 286b of reservoir housing (see FIGS. 72 and 73). With this construction, an inward force exerted on the locking member will deform the locking tab 374 in a manner to permit it to pass through the opening 376 and in so doing release the carriage from the base wall 286b. Release of the carriage will permit the differently configured stored energy means to controllably move the carriage 494 from its first position shown in FIG. 64 to its second position shown in FIG. 73. This stored energy means, which is operably associated with carriage 494, is here provided in the form of a compressible, expandable sponge-like configuration, which is generally designated in the drawings by the numeral 498. This unique stored energy source can, by way of non-limiting example, comprise a micro-porous, meso-porous, macro-porous, ordered structure and can be constructed from Polypropylene (PP), Ultra High Molecular Weight Polyethylene (UHMWPE), High Density Polyethylene (HDPE), Polyvinylidene Fluoride (PVDF), Ethyl-vinyl Acetate (EVA), Styrene Acrylonitrile (SAN), Polytetrafluroethylene (PTFE) and porous cellulose acetate. A suitable source of these materials is Porex Technologies of Fairburn, Ga. The stored energy source can also be constructed from various metalized, porous, sponge-like materials.

With the construction described in the preceding paragraph, following operation of the reservoir-accessing means, and when the locking means of the invention is manipulated in the manner previously described to unlock the carriage assembly from base portion 286b of the main housing, compressible, expandable sponge 498 will move from the compressed configuration as shown in FIG. 64 to the expanded configuration shown in FIG. 73 and, in so doing, will controllably move the carriage from its starting position to its fully deployed or extended position shown in FIG. 73.

As the carriage assembly moves toward its deployed position, the collapsible sidewall 300 of the collapsible container 294 will move into the collapsed configuration shown in FIG. 73. As the collapsible container collapses, the medicinal fluid contained within the container will be controllably expelled therefrom.

To further control the flow of medicinal fluid from reservoir toward the administration set 318 of the invention and then on to the patient, flow control means are provided, which fluid flow control means, are identical in construction and operation to that described in connection with the embodiment of FIGS. 5 through 40. More particularly, with the penetrating member 303 in its advanced position as shown in FIG. 73 fluid communication between the fluid reservoir 295 and the rate control means of the device is established via fluid flow passageway 303a of penetrating member 303. From the fluid passageway of penetrating member 303, fluid will flow into a stub passageway 368, into passageway 370 and then into the inlet 379 of the fluid rate control means of the invention, which is identical to that previously described. From the rate control means, the fluid will flow into passageway 398 and then onwardly to the administration set at a controlled rate.

Figure 74:
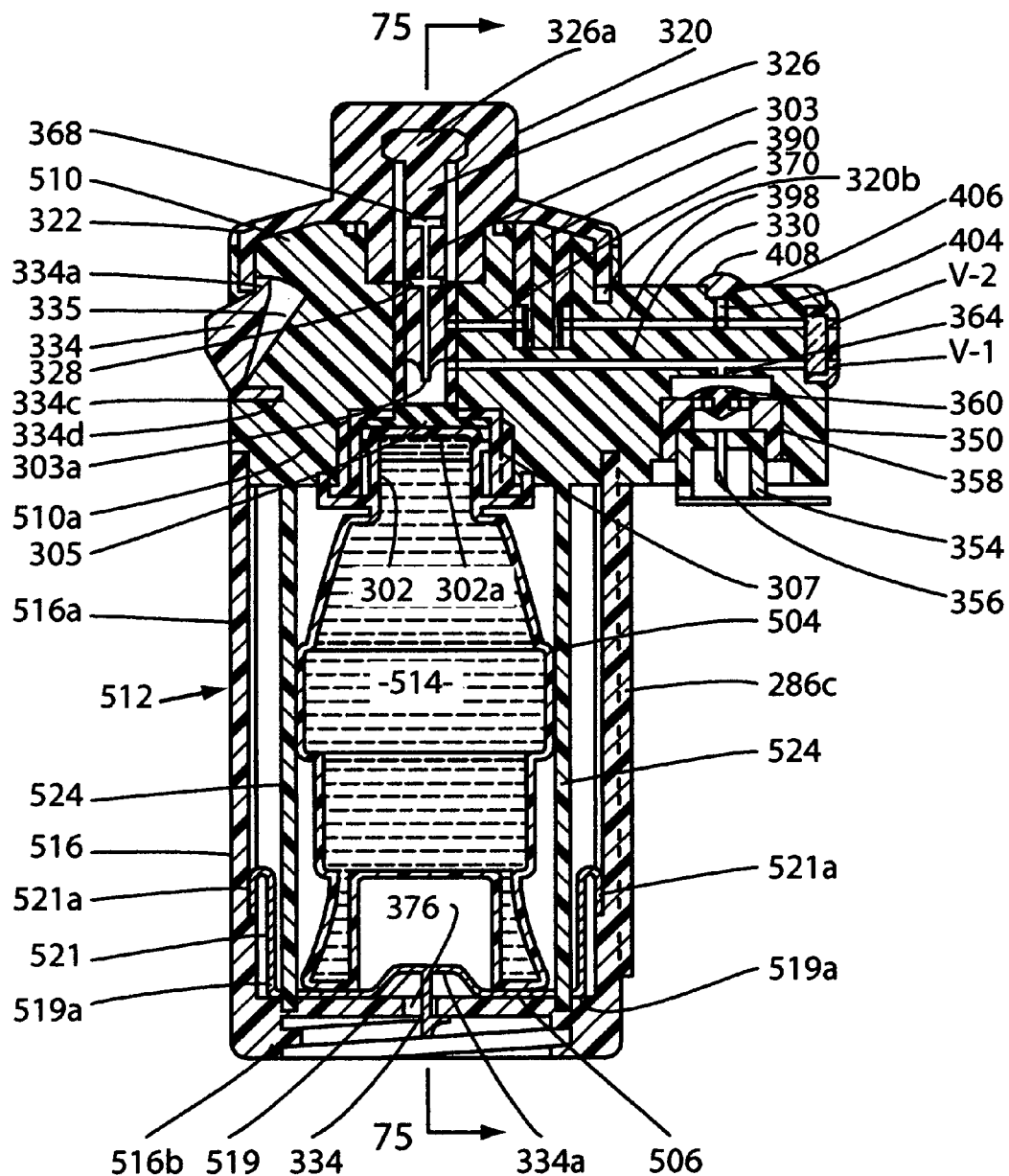
FIG. 74 is a longitudinal, cross-sectional view of still another form of dispenser unit of yet an alternate form of the fluid delivery apparatus of the invention.
Figure 75:
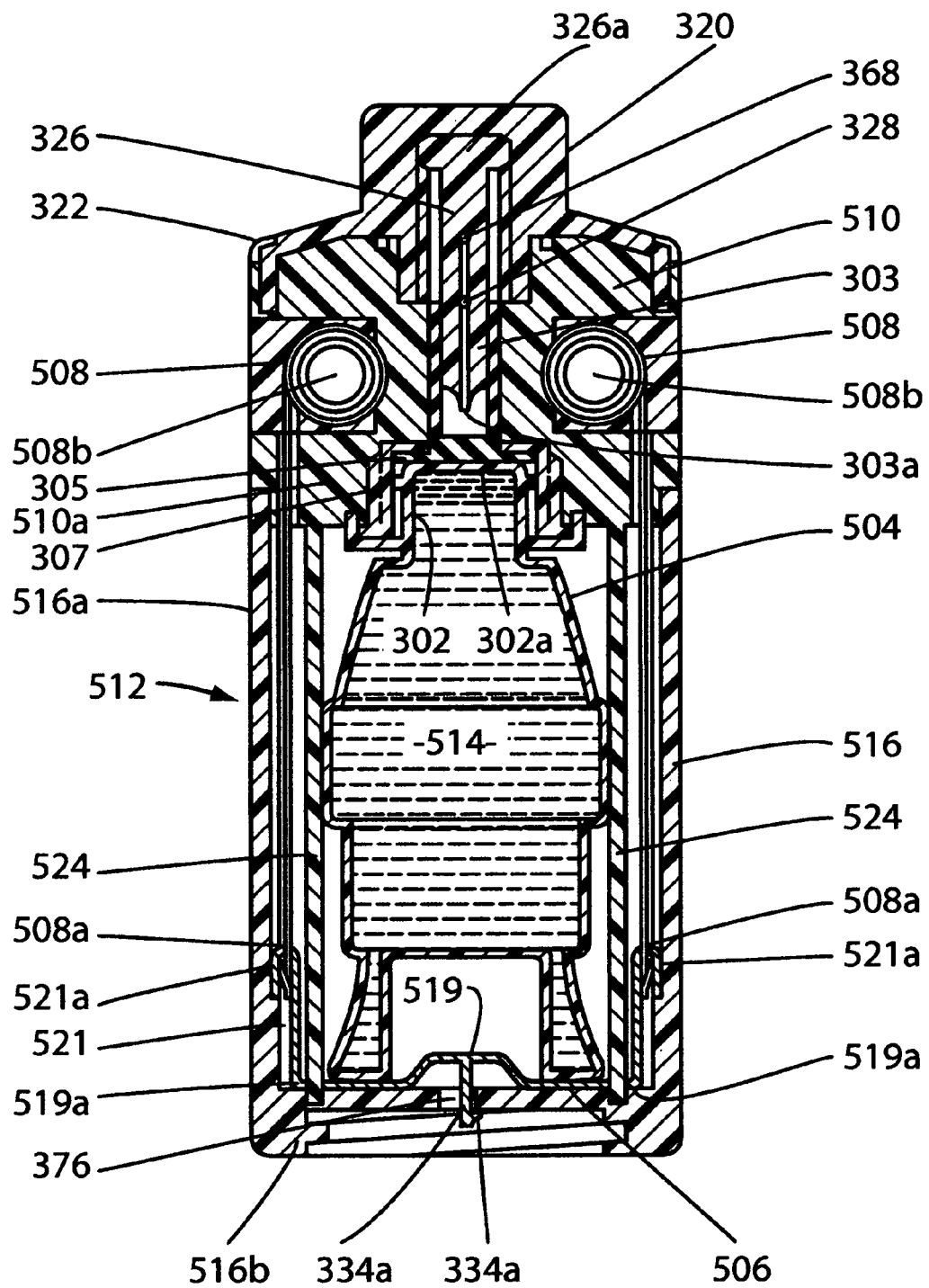
FIG. 75 is a cross-sectional view taken along lines 75-75 of FIG. 74.
Figure 76:
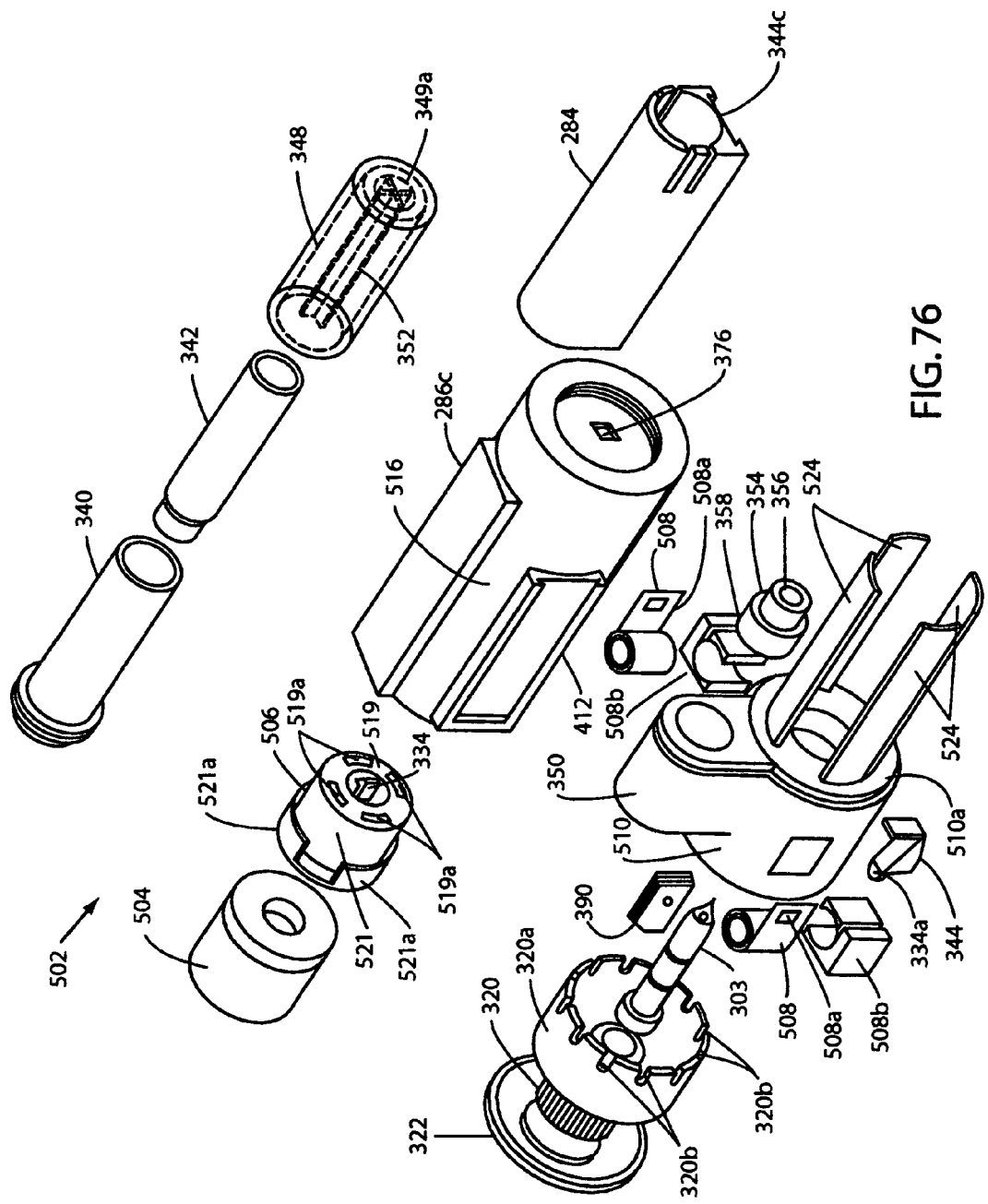
FIG. 76 is a generally perspective, exploded view of the alternate form of dispenser unit shown in FIGS. 74 and 75 and an alternate form of additive sub-system of apparatus that is adapted to be mated with the alternate form of dispenser unit.
Figure 77:
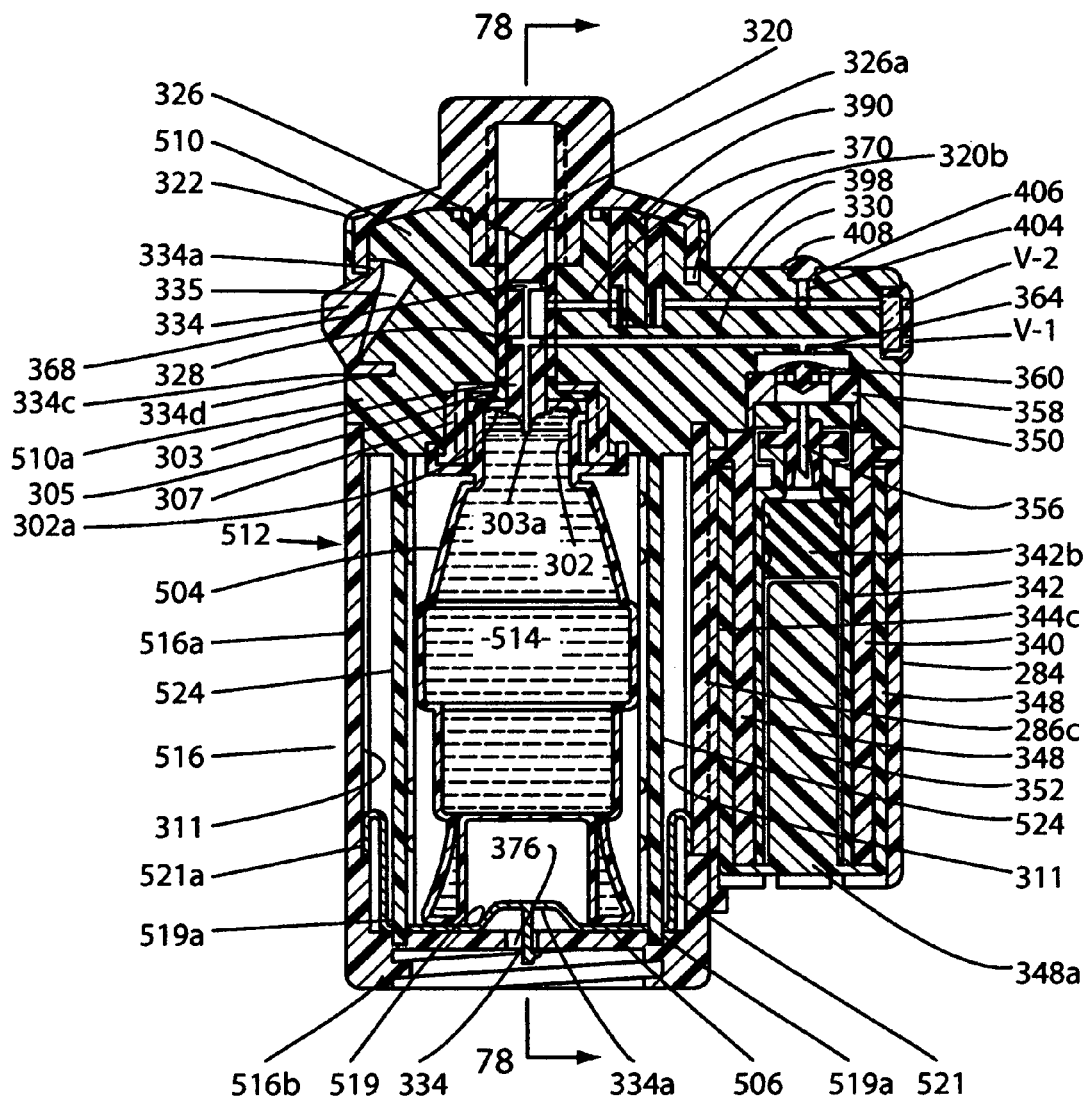
FIG. 77 is a longitudinal, cross-sectional view similar to FIG. 74, but showing the additive sub-system mated with the dispenser unit and showing the operating means having been manipulated in a manner to place the apparatus in condition for the accomplishment of the additive step.
Figure 78:
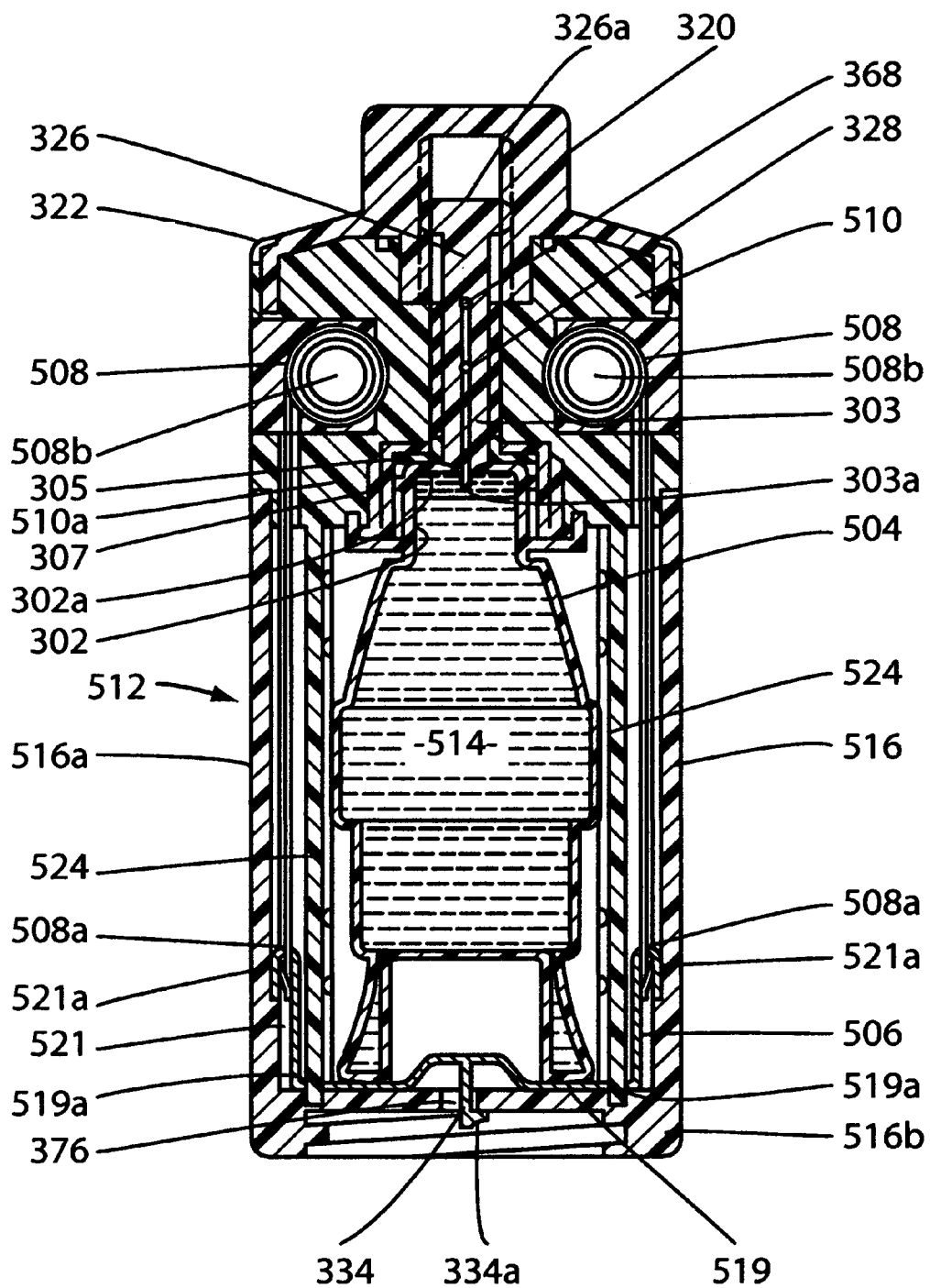
FIG. 78 is a view taken along lines 78-78 of FIG. 77.
Figure 79:
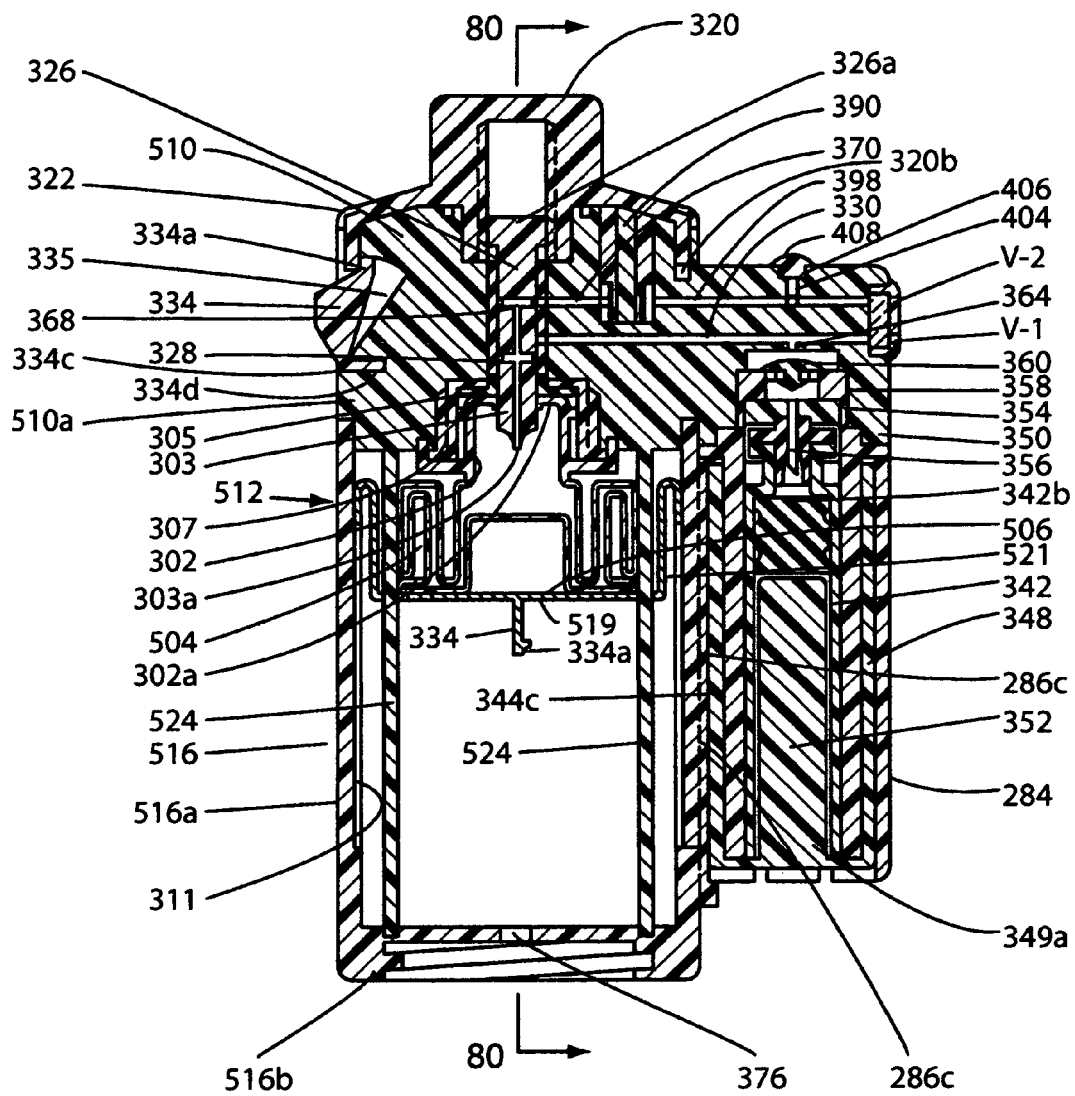
FIG. 79 is a longitudinal cross-sectional view similar to FIG. 77, but showing the device as it appears after accomplishment of the fluid delivery step.

Referring to FIGS. 74 through 80, still another form of the dispensing device of the present invention for dispensing medicaments to a patient is there shown and generally designated by the numeral 502 (FIG. 76). This alternate form of dispensing device is similar in some respects to that shown in FIGS. 5 through 40 and like numerals are used in FIGS. 74 through 80 to identify like components. The major differences between this latest embodiment of the invention and that shown in FIGS. 5 through 40 reside in the totally differently configured stored energy means of the invention. As best seen in FIGS. 74 through 76, the collapsible container 504 and carriage assembly 506 are generally similar in construction to those previously described and the reservoir-adding means for adding medicaments to the fluid contained within the reservoir of the container as well as the operating means are substantially identical in construction and operation to those described in connection with the embodiment of FIGS. 5 through 40. However, the stored energy means, rather than being in the nature of a coil spring, here comprises a pair of spaced-apart, cooperating constant force springs 508 that are carried within the control portion 510 of the dispenser housing 512.

Constant force springs 508, which are a special variety of extension spring, are readily commercially available from several sources including Barnes Group Inc. of Bristol, Conn., Stock Drive Products/Sterling Instrument of Hyde Park, N.Y. and Walker Corporation of Ontario, Canada. These novel springs are basically a high stress, long deflection devices that offer great advantages when used in applications where very low or zero gradient is desired, where space is a factor and where very high reliability is required. Constant force springs, such as springs 508, provide markedly superior constant force loading when compared to conventional helical extension or like springs. Springs 508, after being expanded, tend to uniformly retract and in so doing exert a force on carriage assembly 506 that is mounted within housing 512. Following release of carriage 506 of the carriage assembly, in a manner presently to be described, the carriage will urge the collapsible container 504 to move from the expanded configuration shown in FIG. 74 to the collapsed position shown in FIGS. 79 and 80. As the container 504 collapses the fluid contained within the fluid reservoir 514 will be caused to flow outwardly of the reservoir and toward the flow rate control means of the invention at a substantially constant rate.

As previously mentioned, in this latest form of the invention, the dispenser housing 512 is similar in many respects to the earlier described dispenser housings but is slightly differently configured so as to support the circumferentially spaced constant force springs 508. As illustrated in FIGS. 74, 75 and 76, housing 512 includes a generally cylindrically shaped reservoir housing 516 that is interconnected with the control portion 510 in the manner best seen in FIG. 74 of the drawings. Housing 516, which can be constructed from metal, plastic or any suitable material, includes a generally cylindrically shaped wall portion 516a and a base portion 516b. As indicated in FIG. 75, control portion 510 houses the constant force springs, which are coiled about spool portions 508b. Spool portions 508b are constructed and arranged so that coil springs 508 can extend downwardly within the dispenser housing portion so that the free end thereof can be interconnected with the carriage 506 in the manner shown in FIG. 75.

Figure 80:
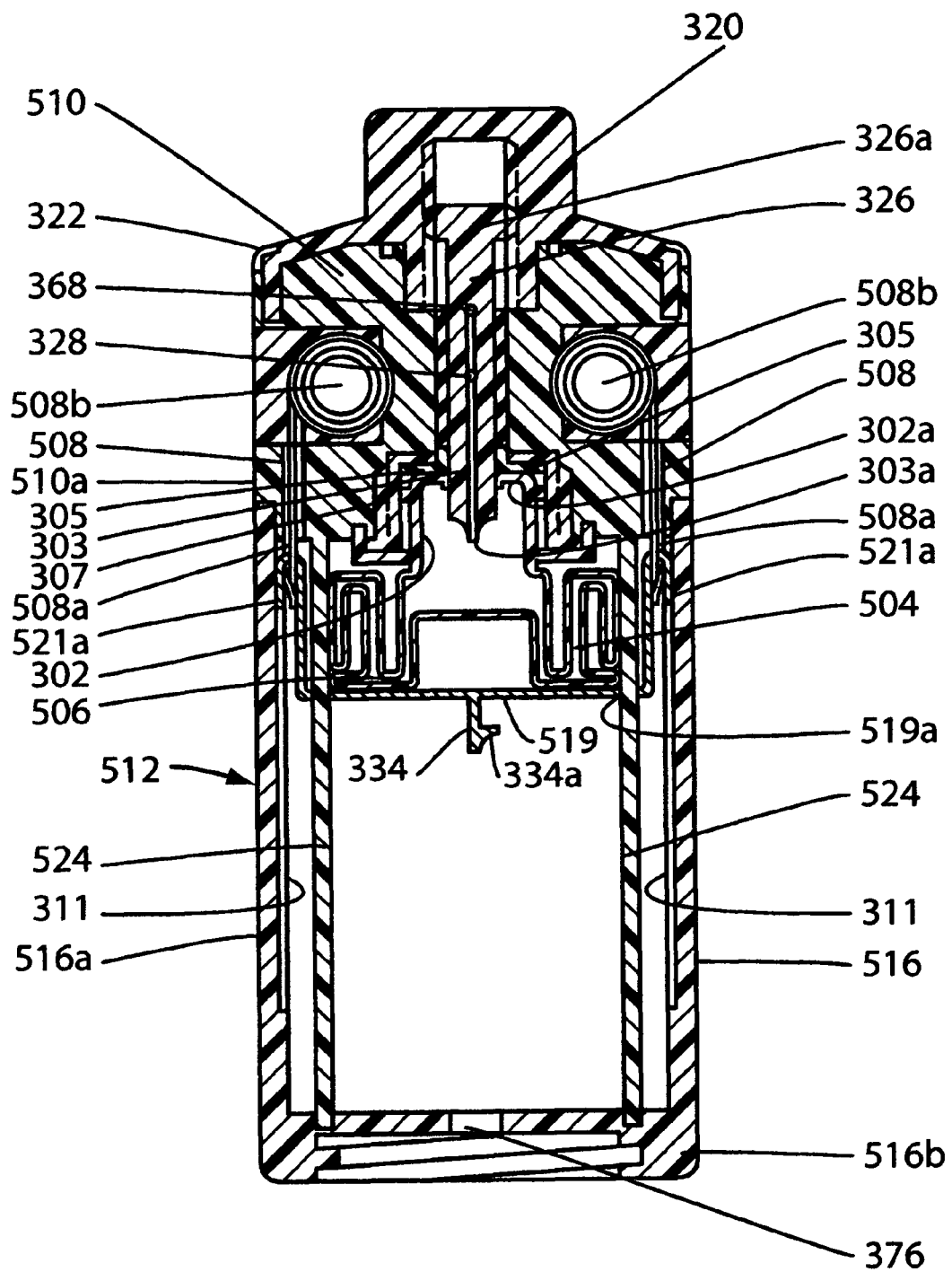
FIG. 80 is a view taken along lines 80-80 of FIG. 79.
Figure 81:
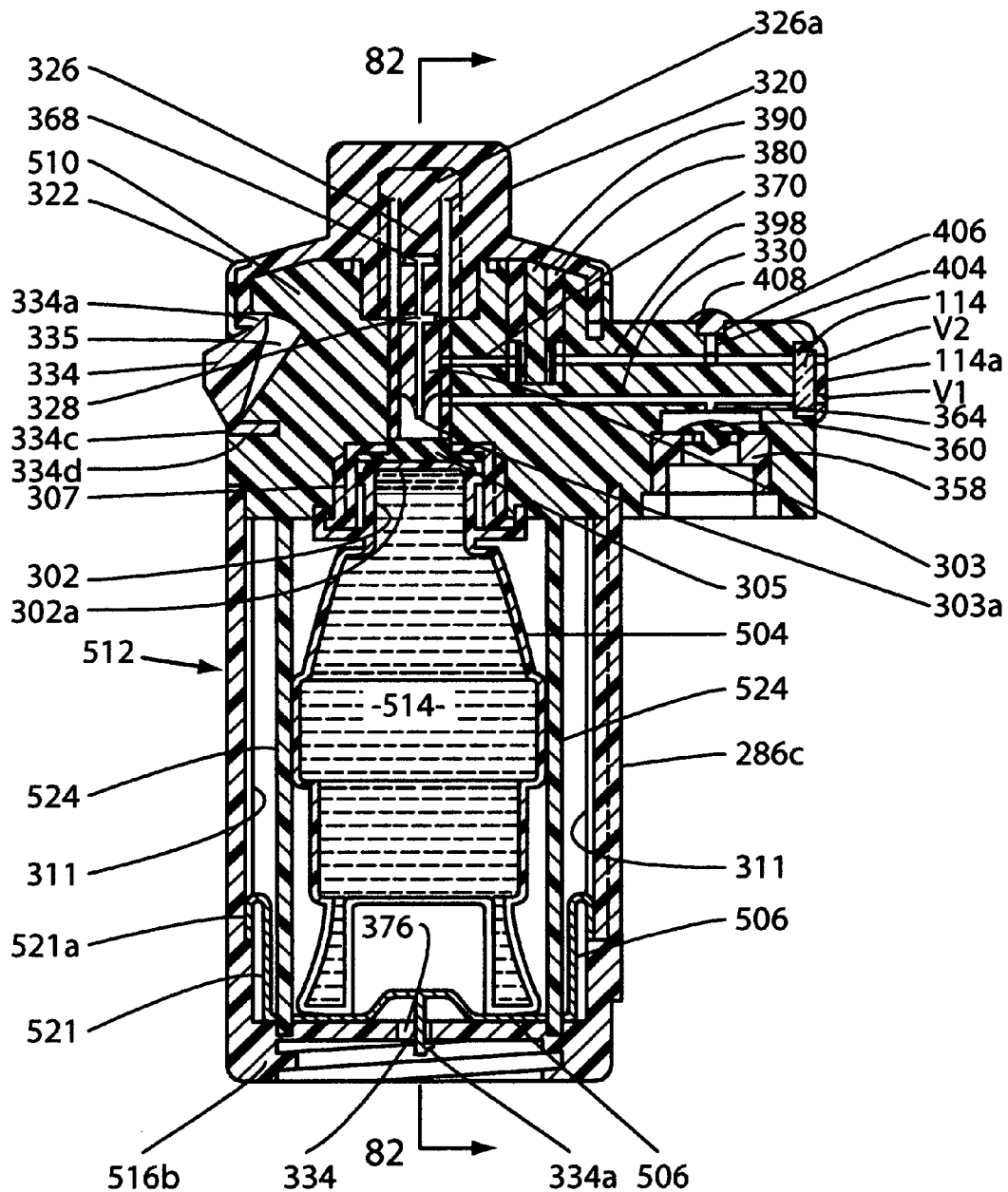
FIG. 81 is a longitudinal, cross-sectional view of yet another form of dispenser unit of still another form of the fluid delivery apparatus of the invention.
Figure 82:
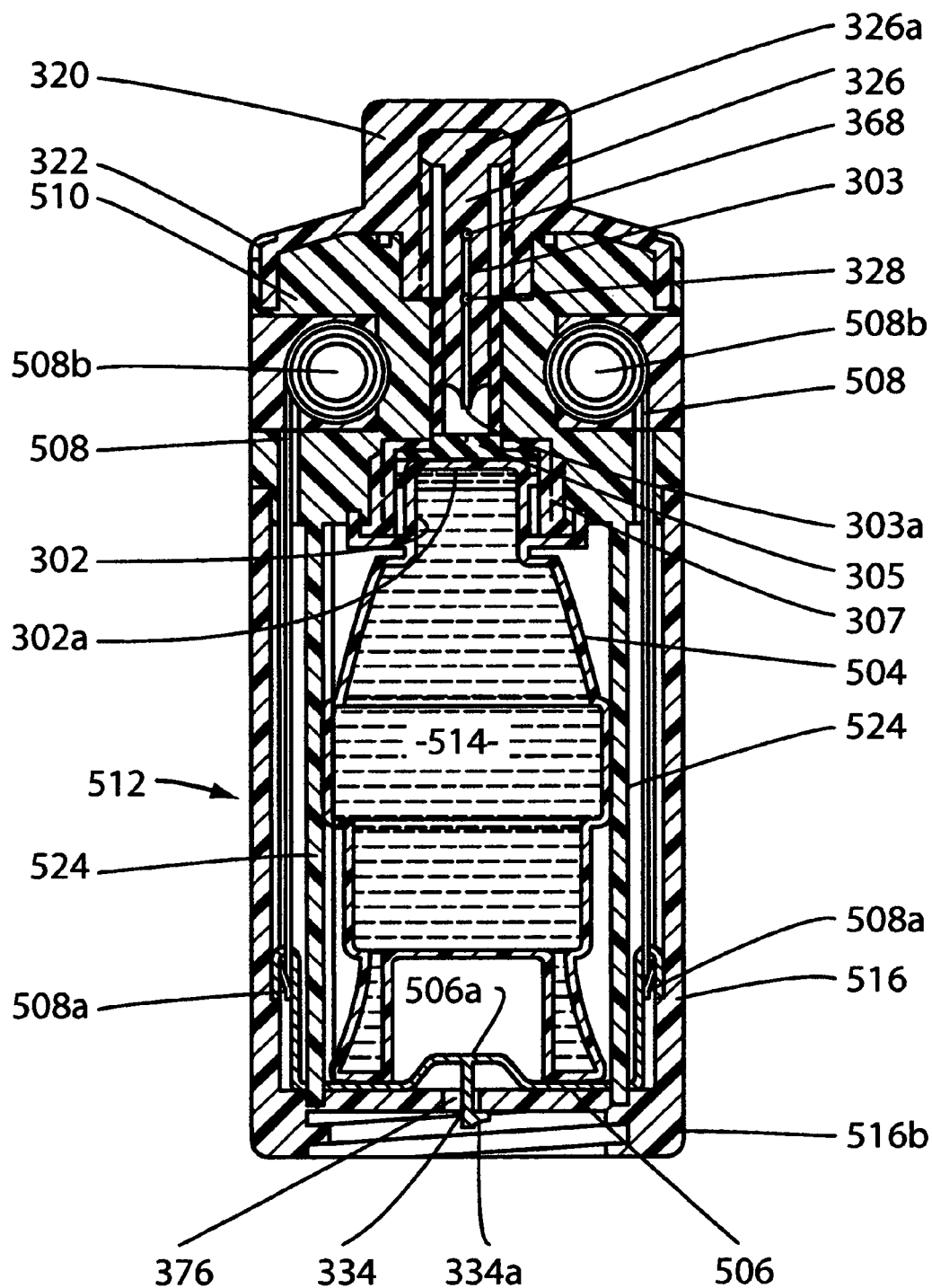
FIG. 82 is a cross-sectional view taken along lines 82-82 of FIG. 81.

Carriage 506, which carries container 504, is movable between a first position shown in FIG. 75 and a second position shown in FIG. 80. As best seen by referring to FIGS. 74, 75 and 76, carriage 506 has a carriage base 519 that is provided with a plurality of circumferentially spaced openings 519a and a generally cylindrically shaped sidewall 521 which terminates in a radially outwardly extending flange 521a. As indicated in the drawings, the free ends 508a of the constant force springs are interconnected with flange 521a. Carriage 506 is releasably locked in its first position by a novel locking means that is of substantially the same construction and operation as that described in connection with the embodiment of FIGS. 5 through 40.

An important feature of this latest form of the invention resides in the provision of novel guide means for guiding travel of carriage assembly 506 between its first and second positions. The guide means here comprises four spaced-apart guide members 524, which are connected to and extend outwardly from body 510a of control portion 510 (FIGS. 75 and 76). As indicated in the drawings, guide members 524 are slidably received within openings 519a provided in carriage base 519 (FIGS. 75 and 76) so that as the carriage assembly travels from its first position toward its second position, guide members 524 precisely guide its travel.

As was described in connection with the embodiment of FIGS. 5 through 40, to accomplish the adding and delivery steps, the dovetail connector segment 286c of the dispenser unit is mated with and urged inwardly of the dovetail receiving groove 344c formed in connector housing 284 (FIG. 76).

Following the completion of the adding process in the manner described in connection with the embodiment of FIGS. 5 through 40, the operating means of the invention is used to control the flow of the fluid mixture from the collapsible reservoir toward the rate control means and then onward toward the administration set of the invention.

In this latest form of the invention, the operating means, the rate control means and the administration set, are all substantially identical to those previously described in connection with the embodiment of FIGS. 5 through 40.

After the reservoir-filling step has been completed, the fluid contained within the reservoir 514 can be dispensed to the patient by once again pivoting the indexing button 334 inwardly to move the locking tab 334*a* out of engagement with the notch in the control knob within which it resides. This done, the control knob is rotated from the "ADD" position (FIG. 20) to the "DISP" position. Release of the indexing button will then cause the outwardly biased locking tab 334*a* to move into engagement with an appropriate locking notch 320*b* so as to lock the control knob in the "DISP" position. This further rotation of control knob 320, will cause penetrating member 303 to move further inwardly to the position illustrated in FIG. 79, wherein the stub passageway 368 formed in penetrating member 303 aligns with a fluid flow passageway 370 formed in control portion 510. With the penetrating member 303 in this advanced position, fluid communication between the fluid reservoir 514 and the rate control means of the device is established via fluid flow passageway 303*a* of penetrating member 303.

To cause the fluid to flow from reservoir 514 toward the flow rate control means, the locking means of the invention must be manipulated in the manner described in connection with the embodiment of FIGS. 5 through 40. Following the release of the locking means, the constant force springs 508 will cause the carriage assembly 506 to move toward its second position causing the sidewall of the container 504 to collapse in the manner illustrated in FIG. 80. As the telescoping sidewall collapses the medicinal fluid mixture contained within the reservoir 514 will be controllably expelled therefrom and will flow toward the fluid passageway 303*a* of penetrating member 303, which has now moved into the position shown in FIG. 79 of the drawings. The fluid will then flow into stub passageway 368 formed in penetrating member 303, into fluid flow passageway 370 and on to the important fluid rate control means of the invention, which is identical in construction and operation to that of the embodiment of FIGS. 5 through 40. From the flow rate control means of the flow control means, the fluid will flow into elongated passageway 398, onward to the administration set 318 and then to the patient. As before, by varying the geometry, including the length, width and depth of the flow control channel of the flow rate control means, the rate of fluid flow to the patient can be readily varied.

Figure 83:
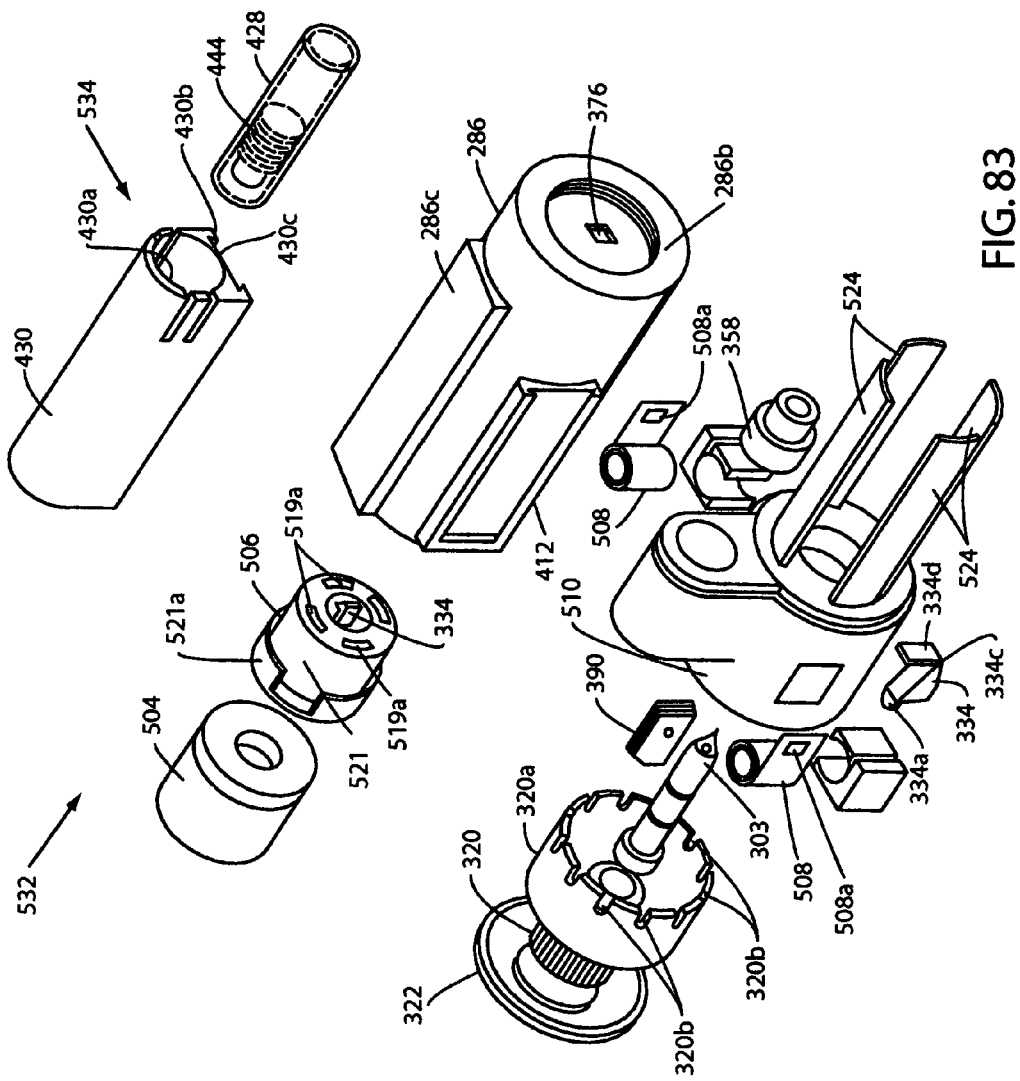
FIG. 83 is a generally perspective, exploded view of the alternate form of dispenser unit shown in FIGS. 81 and 82 and an alternate form of additive sub-system of apparatus that is adapted to be mated with the alternate form of dispenser unit.
Figure 84:
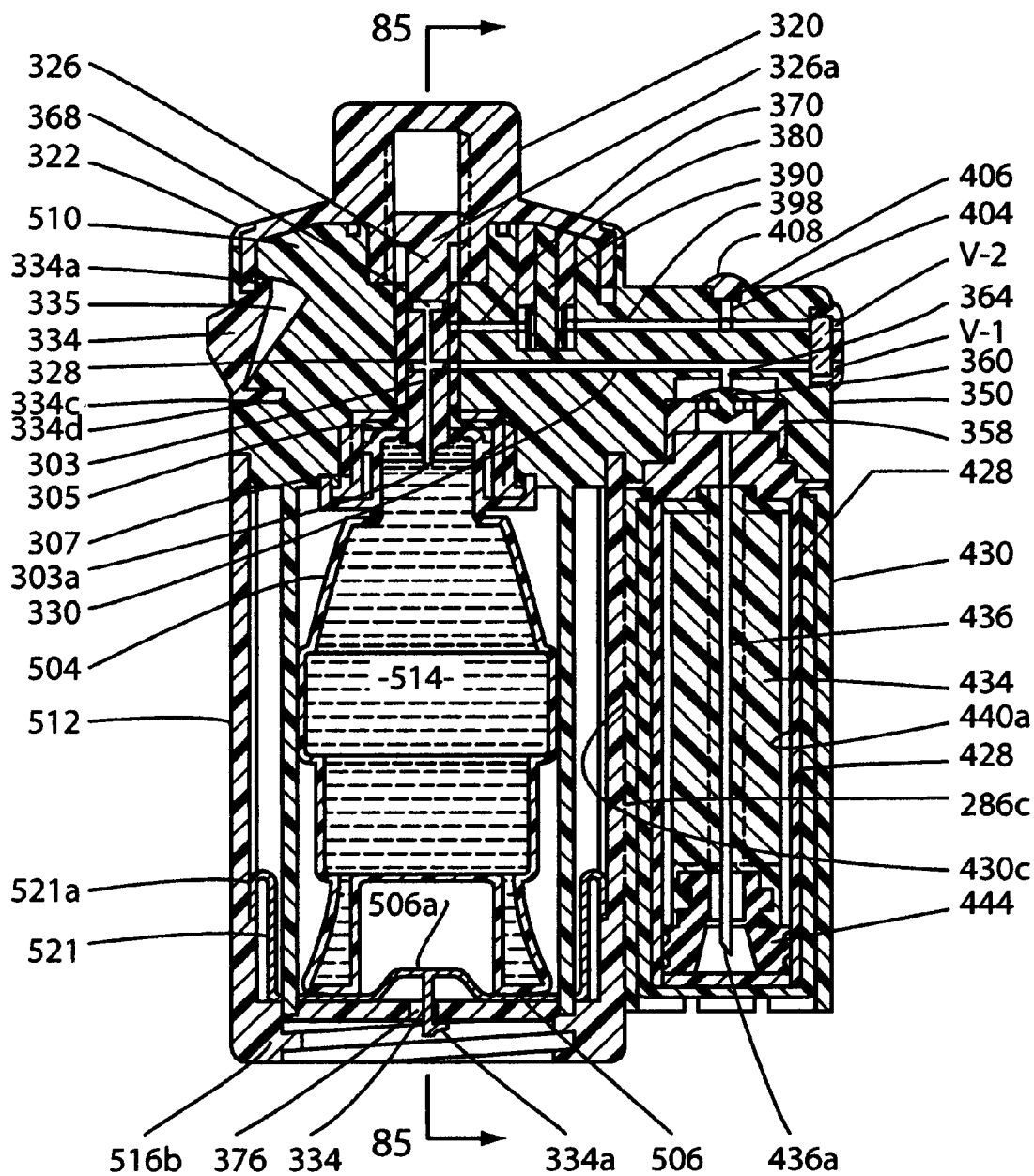
FIG. 84 is a longitudinal, cross-sectional view similar to FIG. 81, but showing additive sub-system mated with the dispenser unit and showing the operating means having been manipulated in a manner to place the apparatus in condition for the accomplishment of the additive step.
Figure 85:
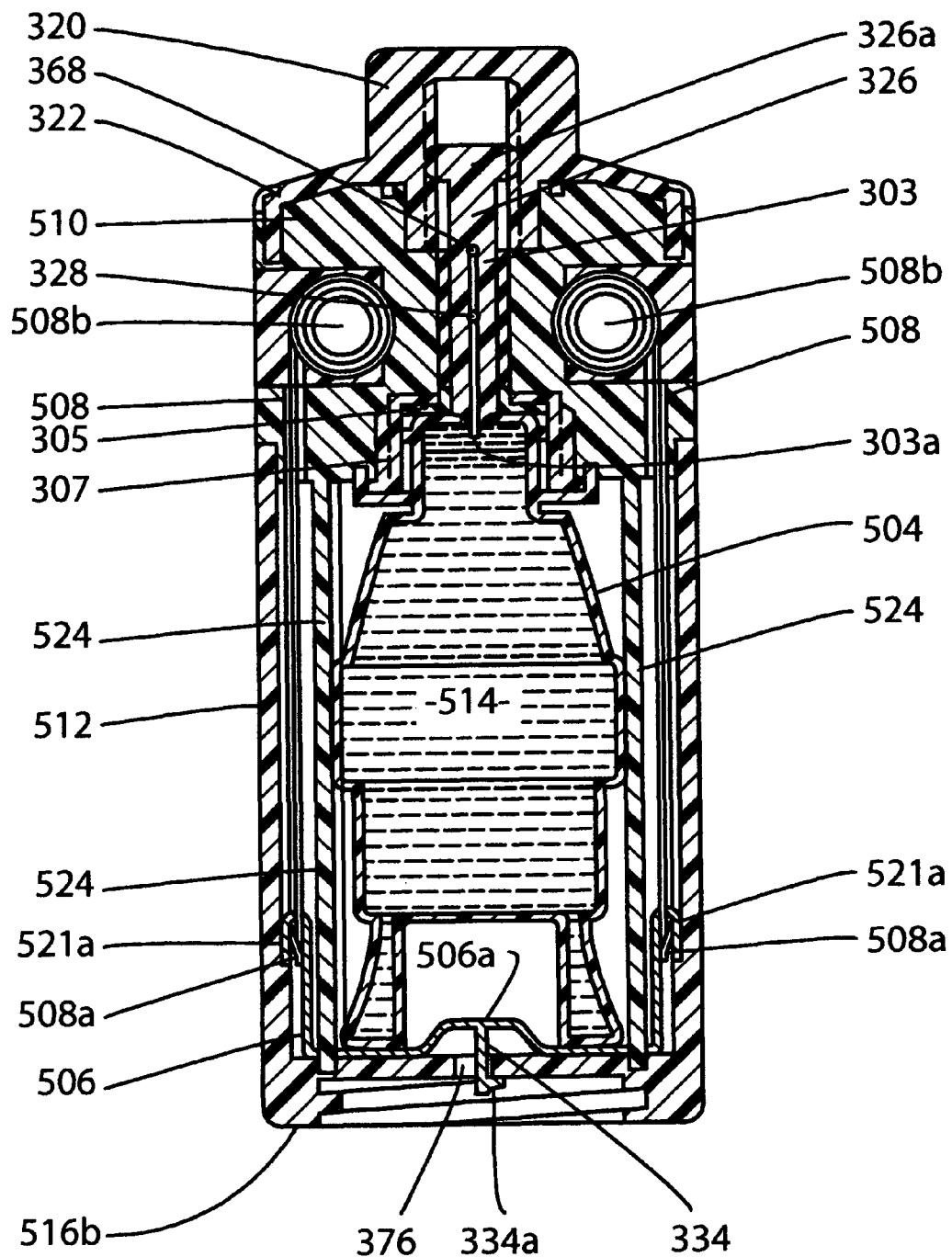
FIG. 85 is a view taken along lines 85-85 of FIG. 84.
Figure 86:
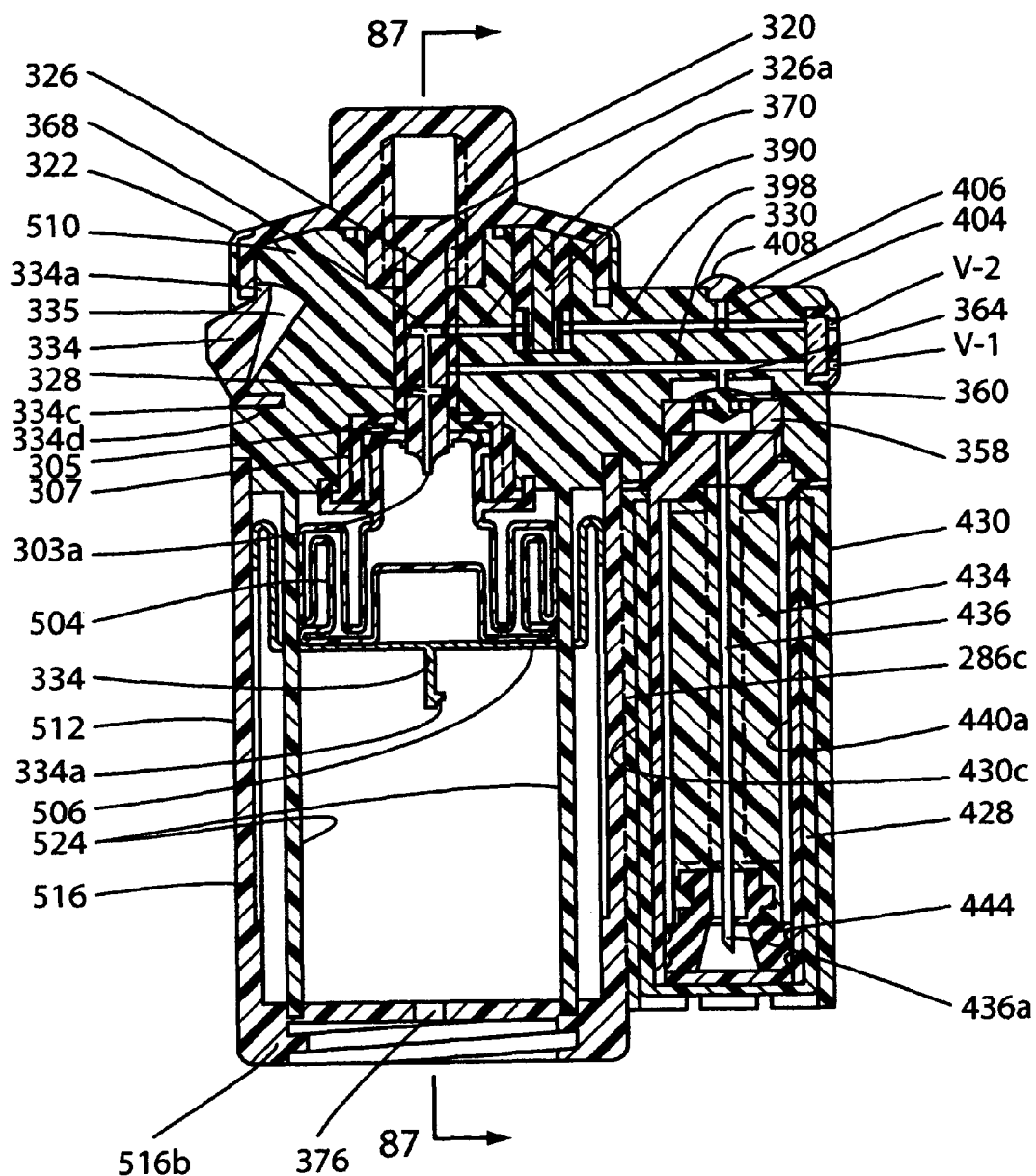
FIG. 86 is a longitudinal, cross-sectional view similar to FIG. 84, but showing the device as it appears after accomplishment of the fluid delivery step.
Figure 87:
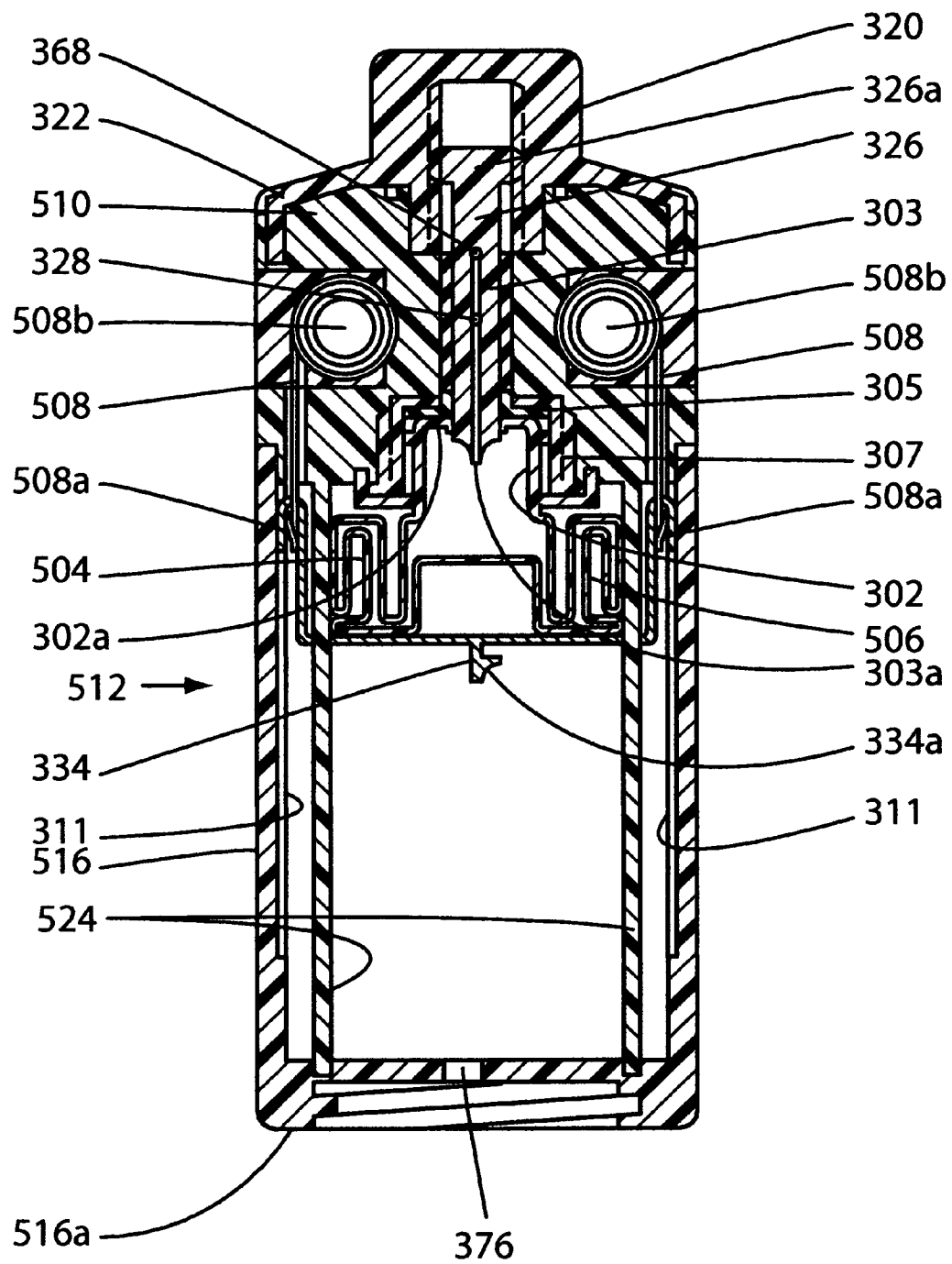
FIG. 87 is a view taken along lines 87-87 of FIG. 86.
Figure 88:
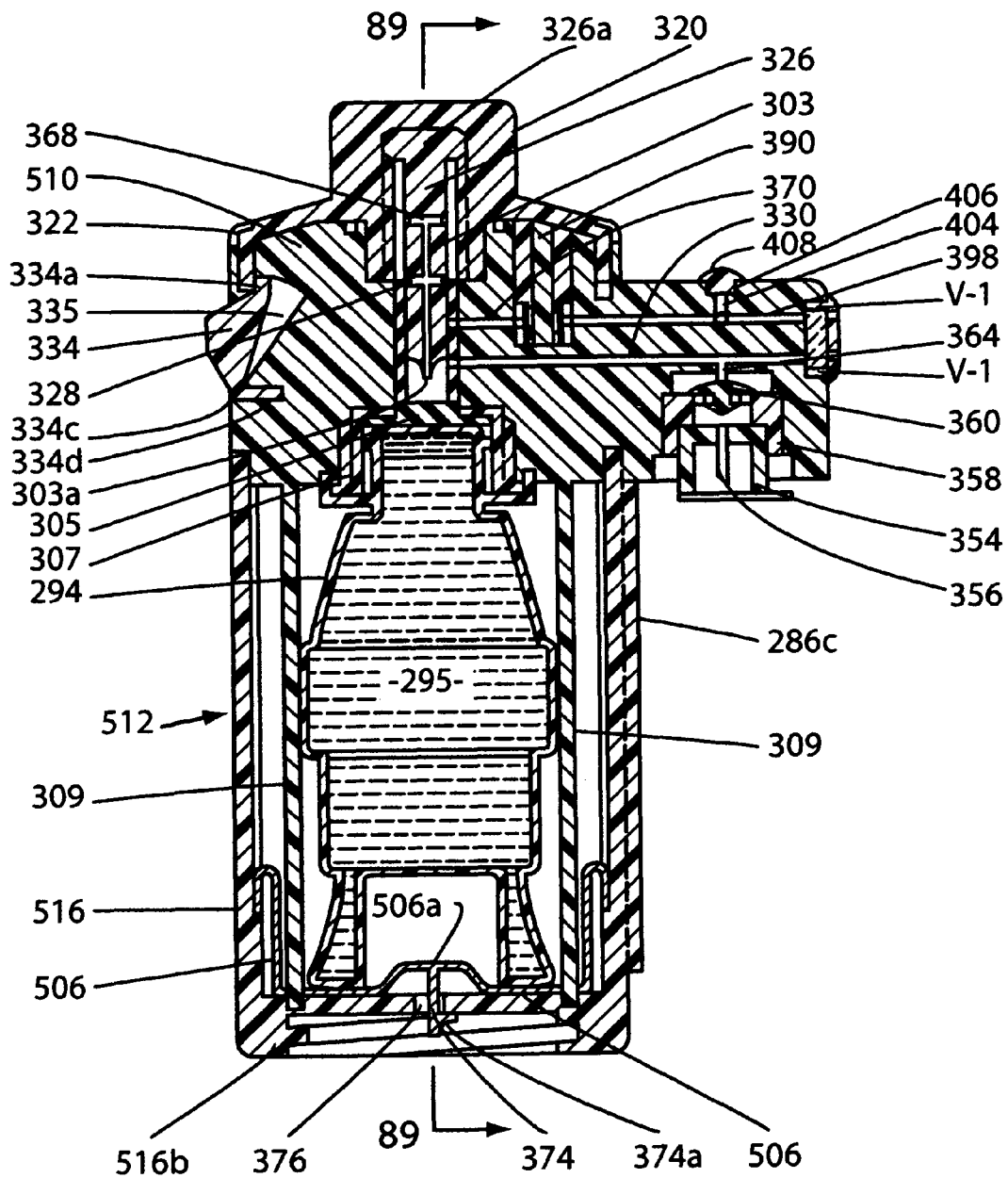
FIG. 88 is a longitudinal, cross-sectional view of yet another form of dispenser unit of still an alternate form of the fluid delivery apparatus of the invention.
Figure 89:
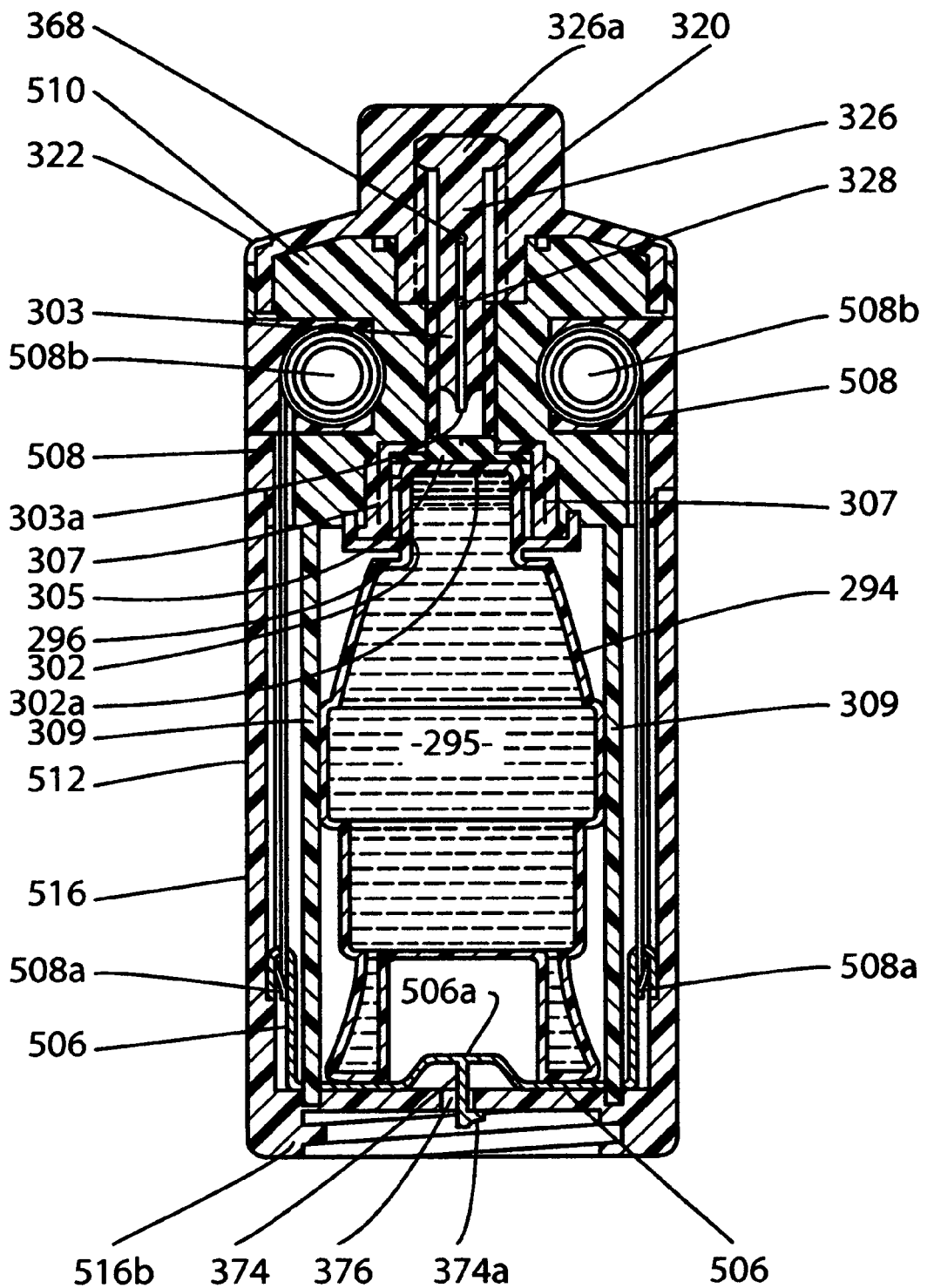
FIG. 89 is a cross-sectional view taken along lines 89-89 of FIG. 88.

Referring to FIGS. 81 through 87, yet another form of the dispensing device of the present invention for dispensing medicaments to a patient is there shown and generally designated by the numeral 532 (FIG. 83). This alternate form of dispensing device is similar in most respects to that shown in FIGS. 74 through 80 and like numerals are used in FIGS. 81 through 87 to identify like components. The major differences between this latest embodiment of the invention and that shown in FIGS. 74 through 80 reside in the differently configured additive sub-system 534. In this regard, additive sub-system 534 of this latest embodiment of the invention is substantially identical to that described in connection with the embodiment illustrated in FIGS. 41 through 48 and comprises a shell vial that is identical to shell vial 428 (FIG. 43).

As indicated in FIGS. 81 through 87, the dispenser housing 512, the collapsible container 504, the carriage assembly 506, the stored energy means and the flow control means are substantially identical in construction and operation to those described in connection with the embodiment of FIGS. 74 through 80.

As in the last described embodiment, the stored energy means here comprises spaced-apart constant force springs 508 that are carried within the control portion 510 of the dispenser housing 512. Following release of carriage 506 of the carriage assembly, in the manner previously described, the carriage will urge the collapsible container 504 to move from the expanded configuration shown in FIG. 81 to the collapsed position shown in FIGS. 86 and 87.

As was described in connection with the embodiment of FIGS. 5 through 40, to accomplish the adding and delivery steps, the dovetail connector segment 286*c* of the dispenser unit is mated with and urged inwardly of the dovetail receiving groove 430*c* formed in connector housing 430 (FIG. 83), which is identical to that earlier described in connection with the embodiment of FIGS. 43 through 50.

Following the completion of the adding process in the manner described in connection with the embodiment of FIGS. 5 through 40, the operating means of the invention is used to control the flow of the fluid mixture from the collapsible reservoir toward the rate control means and then onward toward the administration set of the invention.

In this latest form of the invention, the operating means, as well as the rate control means and the administration set, are substantially identical to those previously described in connection with the embodiment of FIGS. 5 through 40.

After the reservoir-filling step has been completed, the fluid contained within the reservoir 514 can be dispensed to the patient by once again pivoting the indexing button 334 inwardly to move the locking tab 334*a* out of engagement with the control knob notch within which it resides. This done, the control knob is rotated from the "ADD" position (FIG. 20) to the "DISP" position. Release of the indexing button will then cause the outwardly biased locking tab 334*a* to move into engagement with an appropriate locking notch so as to lock the control knob in the "DISP" position. This further rotation of control knob 320, will cause penetrating member 303 to move further inwardly to the position illustrated in FIG. 86, wherein the stub passageway 368 formed in penetrating member 303 aligns with a fluid flow passageway 370 formed in control portion 510. With the penetrating member 303 in this advanced position fluid communication between the fluid reservoir 514 and the rate control means of the device is established via fluid flow passageway 303*a* of penetrating member 303.

To cause the fluid to flow from reservoir 514 toward the flow rate control means, the locking means of the invention must be manipulated in the manner described in connection with the embodiment of FIGS. 5 through 40. Following the release of the locking means, the constant force springs 508 will cause the carriage assembly 506 to move toward its second position causing the telescoping sidewall of the container 504 to collapse in the manner illustrated in FIG. 86. As the telescoping sidewall collapses the medicinal fluid mixture contained within the reservoir 514 will be controllably expelled therefrom and will flow toward the fluid passageway 303*a* of penetrating member 303, which has now moved into the position shown in FIG. 86 of the drawings. The fluid will then flow into stub passageway 368 formed in penetrating member 303, into fluid flow passageway 370 and on to the fluid rate control means of the invention, which is identical in construction and operation to that of the embodiment of FIGS. 5 through 40. From the flow rate control means of the flow control means, the fluid will flow into elongated passageway 398, onward to the administration set 318 and then to the patient.

Figure 90:
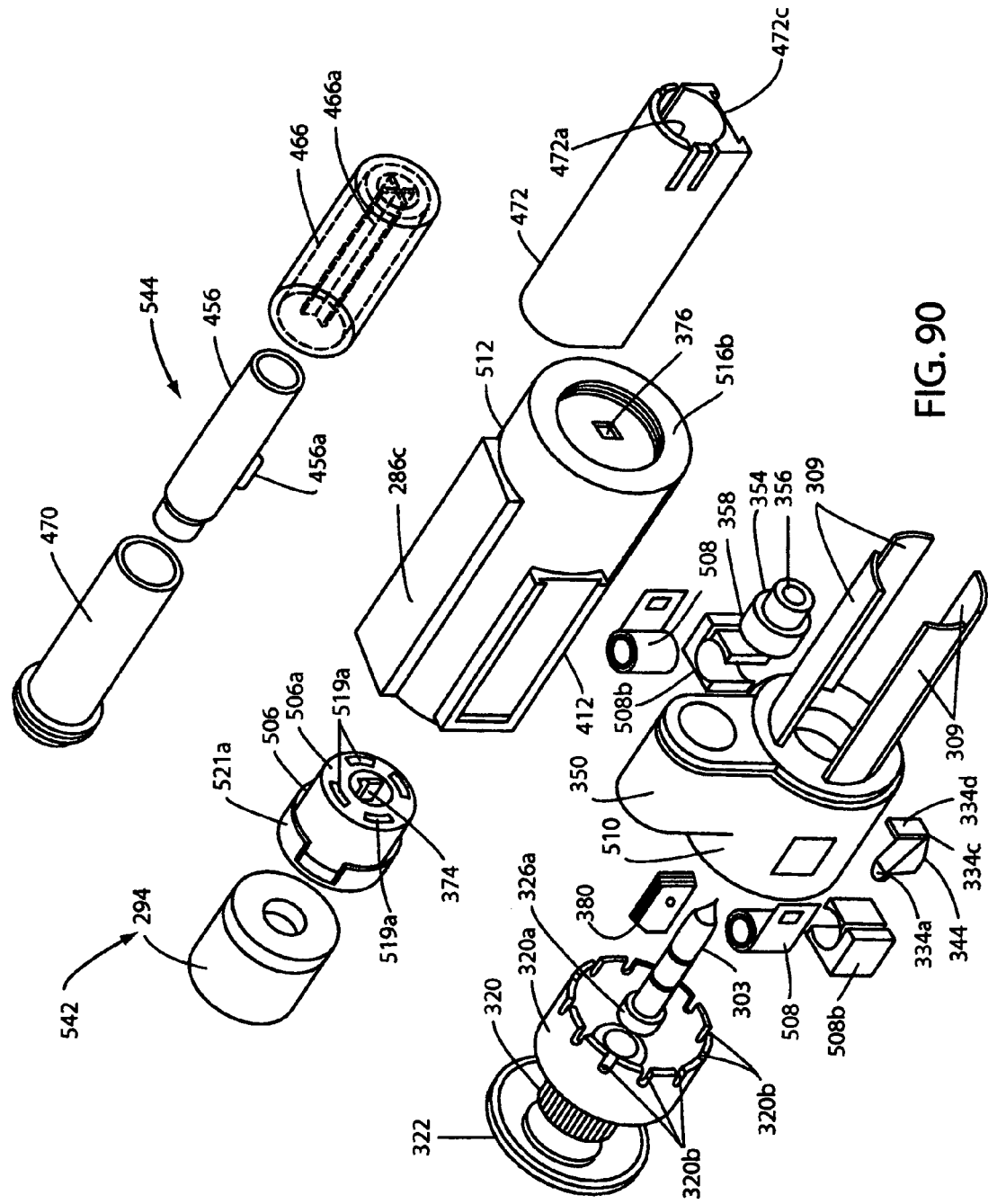
FIG. 90 is a generally perspective, exploded view of the alternate form of dispenser unit shown in FIGS. 88 and 89 and an alternate form of additive sub-system of apparatus that is adapted to be mated with the alternate form of dispenser unit.
Figure 91:
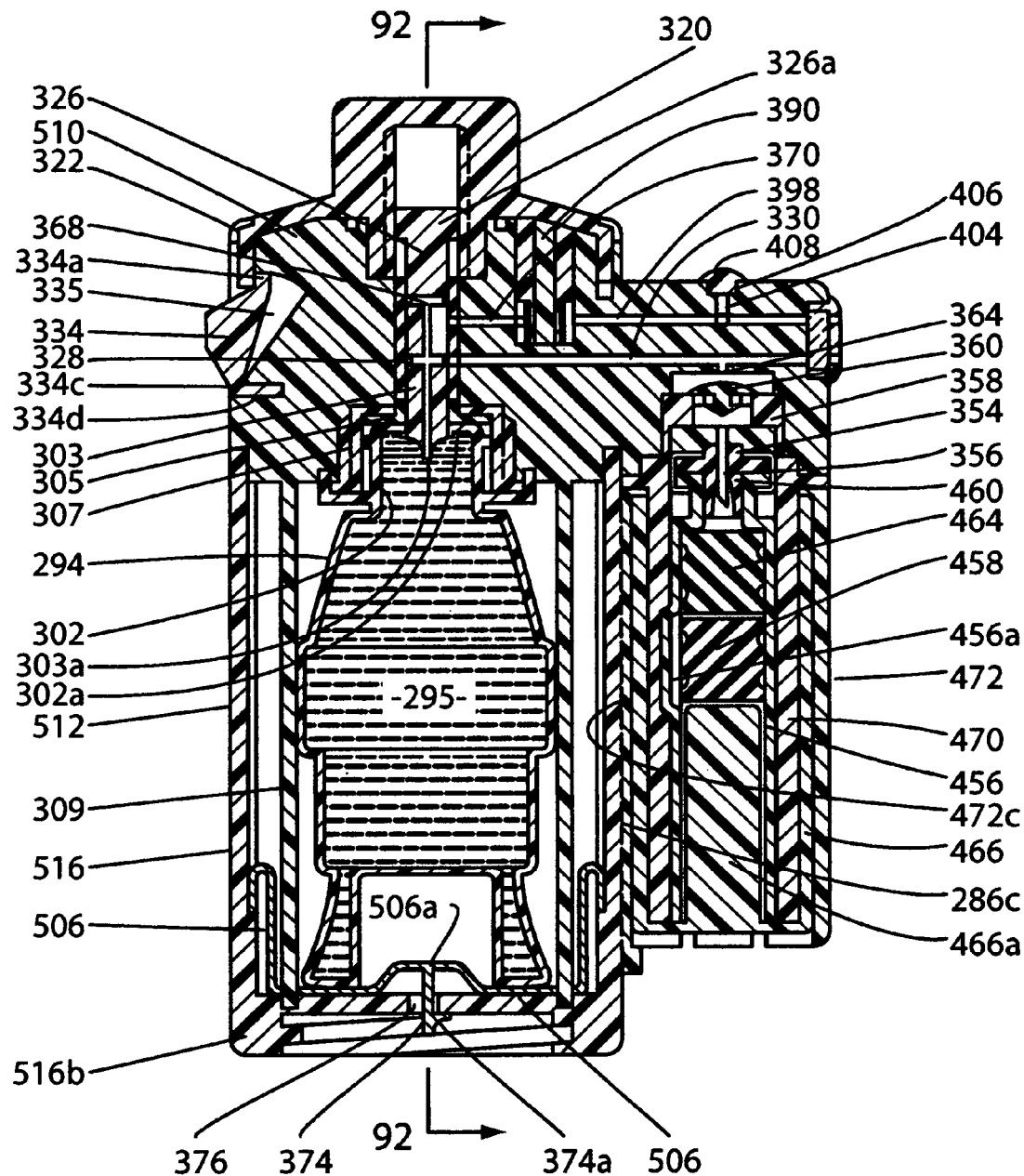
FIG. 91 is a longitudinal, cross-sectional view similar to FIG. 88, but showing the additive sub-system mated with the dispenser unit and showing the operating means having been manipulated in a manner to place the apparatus in condition for the accomplishment of the additive step.
Figure 92:
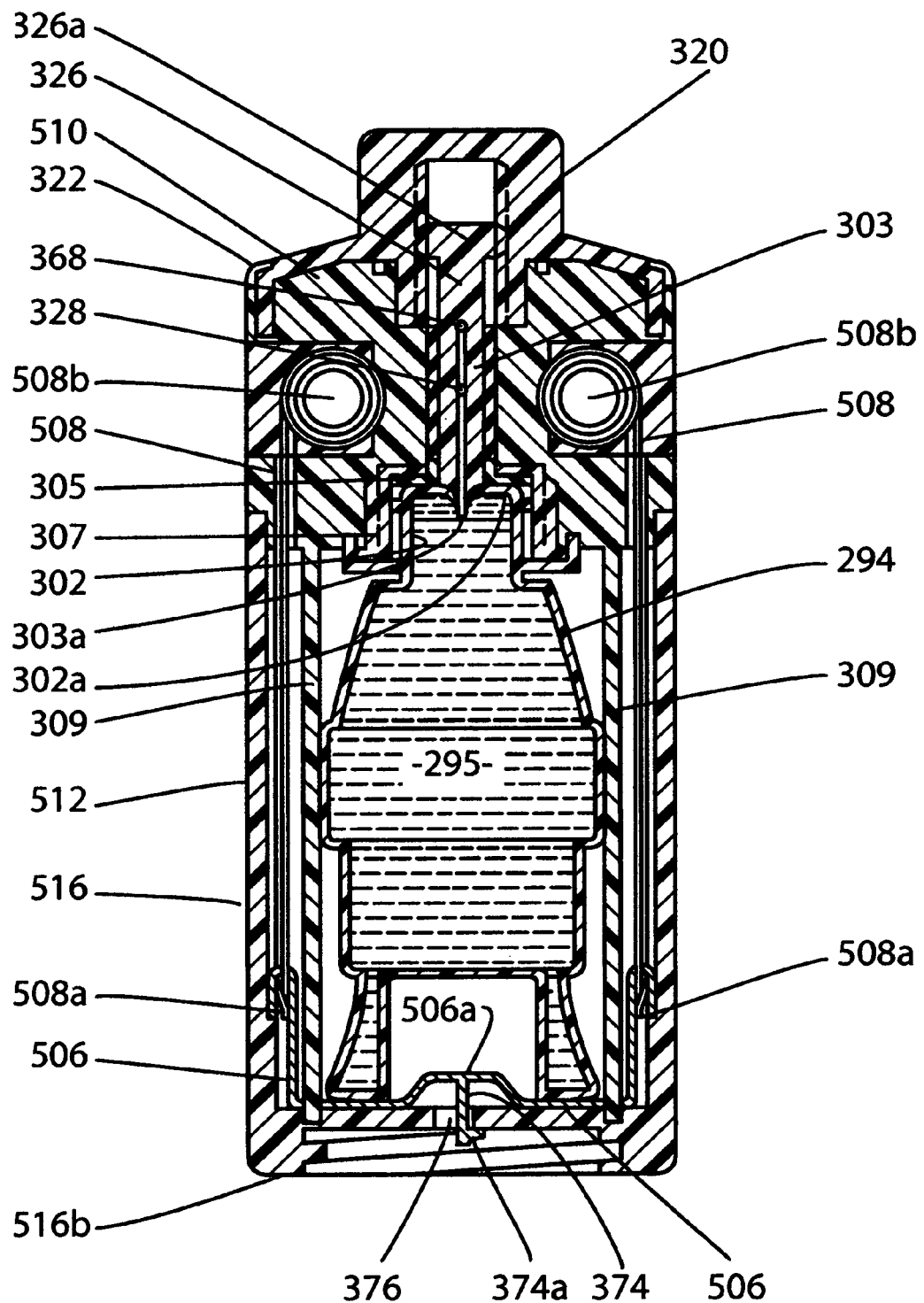
FIG. 92 is a view taken along lines 92-92 of FIG. 91.
Figure 93:
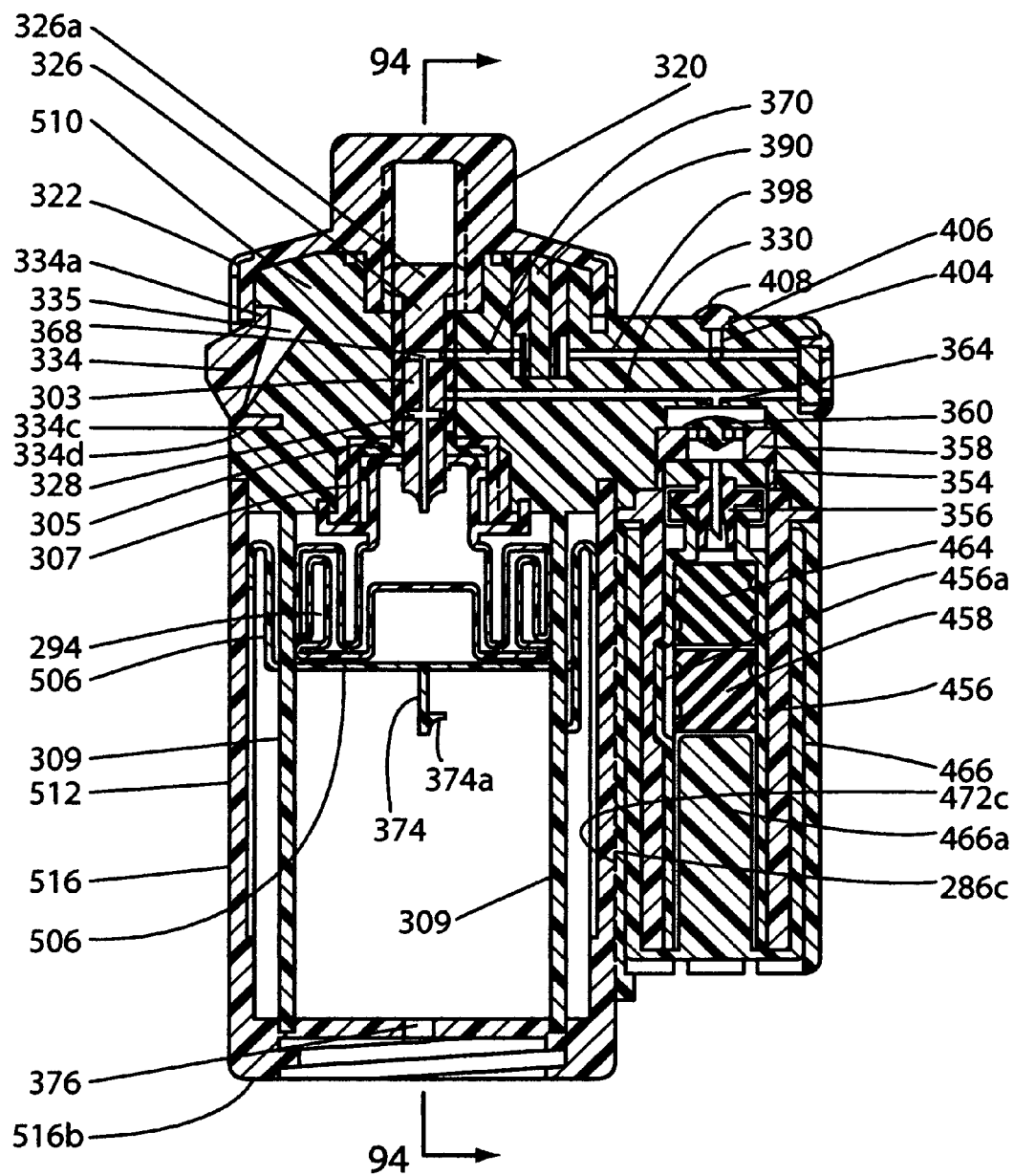
FIG. 93 is a longitudinal, cross-sectional view similar to FIG. 91, but showing the device as it appears after accomplishment of the fluid delivery step.
Figure 94:
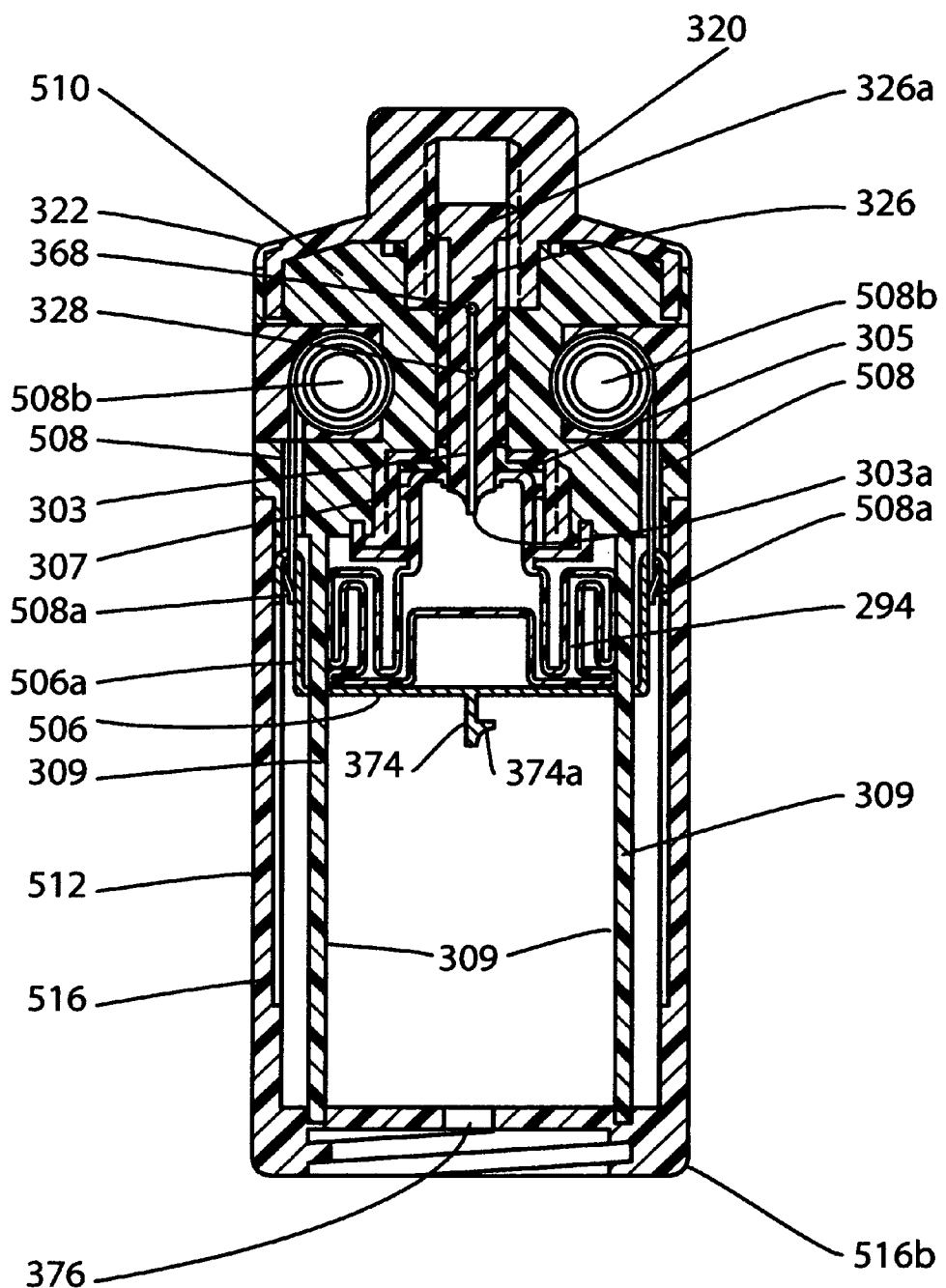
FIG. 94 is a view taken along lines 94-94 of FIG. 93.

Referring to FIGS. 88 through 94, still another form of the dispensing device of the present invention for dispensing medicaments to a patient is there shown and generally designated by the numeral 542 (FIG. 90). This alternate form of dispensing device is similar in most respects to that shown in FIGS. 74 through 87 and like numerals are used in FIGS. 88 through 94 to identify like components. The major differences between this latest embodiment of the invention and that shown in FIGS. 74 through 87 reside in the differently configured additive sub-system 544. In this regard, additive sub-system 544 of this latest embodiment of the invention is substantially identical to that described in connection with the embodiment illustrated in FIGS. 51 through 57 and comprises a vial 456 of special design that uniquely contains a lyophilized drug "D" in a shell vial that is identical to shell vial 428 (FIG. 56).

As indicated in FIGS. 88 through 94, the dispenser housing 512, the collapsible container 294, the carriage assembly 506, the stored energy means and the flow control means are substantially identical in construction and operation to those described in connection with the embodiment of FIGS. 74 through 87.

As in the last described embodiment, the stored energy means here comprises spaced-apart constant force springs 508 that are carried within the control portion 510 of the dispenser housing 512. Following release of carriage 506 of the carriage assembly in the manner previously described, the carriage will urge the collapsible container 294 to move from the expanded configuration shown in FIG. 88 to the collapsed position shown in FIGS. 93 and 94.

As was described in connection with the embodiment of FIGS. 5 through 40, to accomplish the adding and delivery steps, the dovetail connector segment 286c of the dispenser unit is mated with and urged inwardly of the dovetail receiving groove 472c formed in connector housing 472 (FIG. 90), which is identical to that earlier described in connection with the embodiment of FIGS. 43 through 50.

Following the completion of the adding process in the manner described in connection with the embodiment of FIGS. 5 through 40, the operating means of the invention is used to control the flow of the fluid mixture from the collapsible reservoir toward the rate control means and then onward toward the administration set of the invention.

In this latest form of the invention, the operating means, as well as the rate control means and the administration set, are substantially identical to those previously described in connection with the embodiment of FIGS. 5 through 40.

After the reservoir-filling step has been completed, the fluid contained within the reservoir 295 can be dispensed to the patient by once again pivoting the indexing button 334 inwardly to move the locking tab 334a out of engagement with the control knob notch within which it resides. This done, the control knob is rotated from the "ADD" position (FIG. 20) to the "DISP" position. Release of the indexing button will then cause the outwardly biased locking tab 334a to move into engagement with an appropriate locking notch so as to lock the control knob in the "DISP" position. This further rotation of control knob 320, will cause penetrating member 303 to move further inwardly to the position illustrated in FIG. 93, wherein the stub passageway 368 formed in penetrating member 303 aligns with a fluid flow passageway 370 formed in control portion 510. With the penetrating member 303 in this advanced position fluid communication between the fluid reservoir 295 and the rate control means of the device is established via fluid flow passageway 303a of penetrating member 303.

To cause the fluid to flow from reservoir 295 toward the flow rate control means, the locking means of the invention must be manipulated in the manner described in connection with the embodiment of FIGS. 5 through 40. Following the release of the locking means, the constant force springs 508 will cause the carriage assembly 506 to move toward its second position causing the telescoping sidewall of the container 294 to collapse in the manner illustrated in FIG. 93. As the telescoping sidewall collapses the medicinal fluid mixture contained within the reservoir 295 will be controllably expelled therefrom and will flow toward the fluid passageway 303a of penetrating member 303, which has now moved into the position shown in FIG. 93 of the drawings. The fluid will then flow into stub passageway 368 formed in penetrating member 303, into fluid flow passageway 370 and on to the fluid rate control means of the invention, which is identical in construction and operation to that of the embodiment of FIGS. 5 through 40. From the flow rate control means of the flow control means, the fluid will flow into elongated passageway 398, onward to the administration set 318 and then to the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for dispensing medicaments to a patient comprising:
 (a) A fluid dispensing unit comprising:
  (i) a dispenser housing, including a connector portion;
  (ii) a reservoir defining assembly formed in accordance with an aseptic blow-fill-seal manufacturing technique and comprising a collapsible container having a collapsible fluid reservoir carried by said dispenser housing, said collapsible container having a top wall, a bottom wall and a telescoping side wall, said collapsible container having an outlet port and further including a neck portion connected to said top wall, said neck portion being sealed by a closure wall;
  (iii) stored energy means carried by said dispenser housing and operably associated with said collapsible reservoir for collapsing said collapsible reservoir to expel fluid from said outlet port of said collapsible reservoir; and
  (iv) dispensing means connected to said outlet port of said collapsible reservoir for dispensing fluid to the patient; and
 (b) an additive sub-system removably connected to said fluid dispensing unit for adding fluid to said collapsible fluid reservoir of said fluid dispensing unit, said additive sub-system comprising:
  (i) a connector housing removably connected to said connector portion of said dispenser housing of said fluid dispensing unit; and
  (ii) a vial assembly removably receivable within said connector housing, said vial assembly comprising a vial defining a fluid chamber containing a medicament and an elastomeric member movable within said fluid chamber between first and second positions;

(c) fluid flow control means carried by said dispenser housing for controlling fluid flow from said collapsible reservoir toward said dispensing means, said fluid flow control means comprising rate control means for controlling the rate of fluid flow from said collapsible reservoir toward said dispensing means and operating means for controlling fluid flow from said additive subsystem toward said collapsible fluid reservoir, said operating means, comprising reservoir accessing means comprising:
    (i) penetrating means for penetrating said closure wall of said neck portion of said collapsible container; and
    (ii) a control knob rotatably carried by said dispenser housing for causing said penetrating means to penetrate said closure wall.

2. The apparatus as defined in claim 1 in which said stored energy means comprises a spring operably interconnected with said collapsible reservoir.

3. The apparatus as defined in claim 1 in which said stored energy means comprises an expandable sponge operably interconnected with said collapsible reservoir.

4. The apparatus as defined in claim 1 in which said dispensing means comprises an administration set, including an administration line interconnected with said outlet of said collapsible reservoir.

5. The apparatus as defined in claim 1, further including a carriage assembly interconnected with said dispenser housing for movement between a first position and a second position, said collapsible fluid reservoir being carried by said carriage assembly.

6. The apparatus as defined in claim 1 in which said vial of said vial assembly of said additive sub-system contains a diluent and a lyophilized drug.

7. An apparatus for dispensing medicaments to a patient comprising:
  (a) A fluid dispensing unit comprising:
    (i) a dispenser housing, including a connector portion;
    (ii) a carriage assembly connected to said dispenser housing for movement between a first position and a second position;
    (iii) guide means connected to said dispenser housing for guiding travel of said carriage assembly between said first position and said second position:
    (iv) a reservoir defining assembly formed in accordance with an aseptic blow-fill-seal manufacturing technique and comprising a collapsible container having a collapsible fluid reservoir carried by said carriage assembly, said collapsible container having a top wall, a bottom wall, a side wall and an outlet port said collapsible container further including a neck portion connected to said top wall, said neck portion being closed by a closure wall;
    (v) stored energy means carried by said dispenser housing and operably associated with said carriage assembly for moving said carriage assembly toward said second position;
    (vi) an administration set connected to said dispenser housing, said administration set including an administration line interconnected with said outlet of said collapsible reservoir; and
    (vii) fluid flow control means carried by said dispenser housing for controlling fluid flow from said collapsible reservoir toward said administration set, said fluid flow control means comprising rate control means for controlling the rate of fluid flow from said collapsible reservoir toward said dispensing means and operating means for controlling fluid flow from said additive subsystem toward said collapsible fluid reservoir, said operating means comprising reservoir accessing means comprising:
      a. penetrating means for penetrating said closure wall of said neck portion of said collapsible container; and
      b. a control knob rotatably carried by said dispenser housing for causing said penetrating means to penetrate said closure wall;
  (b) an additive sub-system removably connected to said fluid dispensing unit for adding fluid to said collapsible fluid reservoir of said fluid dispensing unit, said additive sub-system comprising:
    (i) a connector housing removably connected to said connector portion of said dispenser housing of said fluid dispensing unit; and
    (ii) a vial assembly removably receivable within said connector housing, said vial assembly comprising a vial defining a fluid chamber containing a medicament and an elastomeric member movable within said fluid chamber between first and second positions.

8. The apparatus as defined in claim 7 in which said stored energy means comprises a pair of spaced-apart constant force springs operably interconnected with said carriage assembly.

9. The apparatus as defined in claim 7 in which said vial of said vial assembly of said additive sub-system contains a diluent and a lyophilized drug.

10. The dispensing device as defined in claim 7 in which said rate control means comprises a rate control plate having a plurality of fluid flow channels interconnected with said outlet of said collapsible reservoir.

11. The apparatus as defined in claim 7 in which said outlet port of said reservoir is closed by a pierceable septum and in which said reservoir-accessing means comprises a penetrating member for penetrating said pierceable septum.

12. An apparatus for dispensing medicaments to a patient comprising:
  (a) A fluid dispensing unit comprising:
    (i) a dispenser housing, including a connector portion;
    (ii) a carriage assembly connected to said dispenser housing for movement between a first position and a second position;
    (iii) a reservoir defining assembly comprising a collapsible container having a collapsible fluid reservoir carried by said carriage assembly, said collapsible container having a top wall, a bottom wall, a telescoping side wall, and an outlet port, said collapsible container further including a neck portion connected to said top wall and a closure wall connected to and spanning said neck portion;
    (iv) stored energy means carried by said dispenser housing and operably associated with said carriage assembly for moving said carriage assembly toward said second position, said stored energy means comprising a spring; and
    (v) fluid flow control means carried by said dispenser housing for controlling fluid flow from said collapsible reservoir toward said administration set, said fluid flow control means comprising rate control means for controlling the rate of fluid flow from said collapsible reservoir toward said dispensing means, said rate control means comprising a rate control plate having a plurality of fluid flow channels interconnected with said collapsible reservoir and operating means for controlling fluid flow from said additive subsystem toward said collapsible fluid reservoir, said operating means comprising reservoir accessing means comprising:
   a. penetrating means for penetrating said closure wall of said neck portion of said collapsible container; and
   b. a control knob rotatably carried by said dispenser housing for causing said penetrating means to penetrate said closure wall; and
(b) an additive sub-system removably connected to said fluid dispensing unit for adding fluid to said collapsible fluid reservoir of said fluid dispensing unit, said additive sub-system comprising:
   (i) a connector housing removably connected to said connector portion of said dispenser housing of said fluid dispensing unit; and
   (ii) a vial assembly removably receivable within said connector housing, said vial assembly comprising a vial defining a fluid chamber containing a medicament and an elastomeric member movable within said fluid chamber between first and second positions.

13. The apparatus as defined in claim 12 in which said stored energy means comprises a coil spring.

14. The apparatus as defined in claim 12 in which said stored energy means comprises a pair of spaced-apart constant force springs operably interconnected with said carriage assembly.

15. The apparatus as defined in claim 12 in which said vial of said vial assembly of said additive sub-system contains a diluent and a lyophilized drug.

16. The apparatus as defined in claim 12 in which said outlet port of said reservoir is closed by a pierceable septum and in which said reservoir-accessing means comprises a penetrating member for penetrating said pierceable septum.

\* \* \* \* \*